US008557232B2

(12) United States Patent
Gillies et al.

(10) Patent No.: US 8,557,232 B2
(45) Date of Patent: Oct. 15, 2013

(54) STABILIZATION OF FC-INTERFERON-BETA FUSION PROTEINS

(75) Inventors: Stephen D. Gillies, Carlisle, MA (US); Nigel John Watkins, Cambridgeshire (GB); Matthew Paul Baker, Cambridge (GB); Kin-Ming Lo, Lexington, MA (US); Steven C. Degon, Hampton, NH (US)

(73) Assignee: Merck Patent GmbH, Darmstadt (DE)

( * ) Notice: Subject to any disclaimer, the term of this patent is extended or adjusted under 35 U.S.C. 154(b) by 403 days.

(21) Appl. No.: 12/395,165

(22) Filed: Feb. 27, 2009

(65) Prior Publication Data

US 2009/0191154 A1 Jul. 30, 2009

Related U.S. Application Data

(62) Division of application No. 11/167,767, filed on Jun. 27, 2005, now Pat. No. 7,670,595.

(60) Provisional application No. 60/583,389, filed on Jun. 28, 2004.

(51) Int. Cl.

| | |
|---|---|
| ***A61K 38/21*** | (2006.01) |
| ***A61K 38/00*** | (2006.01) |
| ***A61K 39/00*** | (2006.01) |
| ***C07K 14/565*** | (2006.01) |

(52) U.S. Cl.
USPC ......... 424/85.6; 424/134.1; 514/1.1; 530/351

(58) Field of Classification Search
None
See application file for complete search history.

(56) References Cited

U.S. PATENT DOCUMENTS

| | | | |
|---|---|---|---|
| 4,469,797 | A | 9/1984 | Albarella |
| 4,737,462 | A | 4/1988 | Mark et al. |
| 5,019,368 | A | 5/1991 | Epstein et al. |
| 5,349,053 | A | 9/1994 | Landolfi |
| 5,480,981 | A | 1/1996 | Goodwin et al. |
| 5,541,087 | A | 7/1996 | Lo et al. |
| 5,601,819 | A | 2/1997 | Wong et al. |
| 5,609,846 | A | 3/1997 | Goldenberg |
| 5,614,184 | A | 3/1997 | Sytkowski et al. |
| 5,645,835 | A | 7/1997 | Fell, Jr. et al. |
| 5,650,150 | A | 7/1997 | Gillies |
| 5,679,543 | A | 10/1997 | Lawlis |
| 5,709,859 | A | 1/1998 | Aruffo et al. |
| 5,723,125 | A | 3/1998 | Chang et al. |
| 5,726,044 | A | 3/1998 | Lo et al. |
| 5,728,552 | A | 3/1998 | Fujisawa et al. |
| 5,770,195 | A | 6/1998 | Hudziak et al. |
| 5,795,779 | A | 8/1998 | McCormick et al. |
| 5,827,516 | A | 10/1998 | Urban et al. |
| 5,827,703 | A | 10/1998 | Debs et al. |
| 5,843,423 | A | 12/1998 | Lyman et al. |
| 5,908,626 | A | 6/1999 | Chang et al. |
| 6,086,875 | A | 7/2000 | Blumberg et al. |
| 6,100,387 | A | 8/2000 | Herrmann et al. |
| 6,169,070 | B1 | 1/2001 | Chen et al. |
| 6,335,176 | B1 | 1/2002 | Inglese et al. |
| 6,444,792 | B1 | 9/2002 | Gray et al. |
| 6,475,717 | B1 | 11/2002 | Enssle et al. |
| 6,485,726 | B1 | 11/2002 | Blumberg et al. |
| 6,500,641 | B1 | 12/2002 | Chen et al. |
| 6,551,592 | B2 | 4/2003 | Lindhofer et al. |
| 6,617,135 | B1 | 9/2003 | Gillies et al. |
| 6,620,413 | B1 | 9/2003 | DeSauvage et al. |
| 6,627,615 | B1 | 9/2003 | Debs et al. |
| 6,646,113 | B1 | 11/2003 | Dreyfuss et al. |
| 6,750,329 | B1 | 6/2004 | Rosenblum et al. |
| 6,838,260 | B2 | 1/2005 | Gillies et al. |
| 6,969,517 | B2 | 11/2005 | Gillies et al. |
| 6,992,174 | B2 | 1/2006 | Gillies et al. |
| 7,067,110 | B1 | 6/2006 | Gillies et al. |
| 7,091,321 | B2 | 8/2006 | Gillies et al. |
| 7,141,651 | B2 | 11/2006 | Gillies et al. |
| 7,148,321 | B2 | 12/2006 | Gillies et al. |
| 7,169,904 | B2 | 1/2007 | Gillies et al. |
| 7,186,804 | B2 | 3/2007 | Gillies et al. |
| 7,211,253 | B1 | 5/2007 | Way |
| 7,226,998 | B2 | 6/2007 | Gillies et al. |
| 7,323,549 | B2 | 1/2008 | Lauder et al. |
| 7,381,795 | B2 | 6/2008 | Carr et al. |

(Continued)

FOREIGN PATENT DOCUMENTS

| | | |
|---|---|---|
| AU | 21725/88 | 3/1989 |
| EP | 0 237 019 A2 | 9/1987 |

(Continued)

OTHER PUBLICATIONS

Benacerraf et al., (1959), "The Clearance of Antigen Antibody Complexes from the Blood by the Reticulo-Endothelial System," *J. Immunol.*, 82:131-7.

Beutler et al., (1988), "Tumor Necrosis, Cachexia, Shock, and Inflammation: A Common Mediator," *Annual Rev. Biochem.*, 57:505-518.

Bitonti et al. (2004), "Pulmonary Delivery of an Erythropoietin Fc Fusion Protein in Non-Human Primates Through an Immunoglobulin Transport Pathway," *Proc. Natl. Acad. Sci. USA*, 101(26):9763-9768.

(Continued)

*Primary Examiner* — Robert Landsman
*Assistant Examiner* — Bruce D Hissong
(74) *Attorney, Agent, or Firm* — Goodwin Procter LLP

(57) ABSTRACT

Disclosed are Fc-interferon-beta (Fc-IFN-β) fusion proteins and nucleic acid molecules encoding them. The Fc-IFN-β fusion proteins include variants of the interferon-beta (IFN-β) protein that are altered to achieve enhanced biological activity, prolonged circulating half-life and greater solubility. Also disclosed are methods of producing the fusion proteins and methods of using the fusion proteins and/or nucleic acid molecules for treating diseases and conditions alleviated by the administration of interferon-beta.

14 Claims, 24 Drawing Sheets

(56) References Cited

U.S. PATENT DOCUMENTS

| | | | |
|---|---|---|---|
| 7,432,357 | B2 | 10/2008 | Gillies |
| 7,459,538 | B2 | 12/2008 | Gillies et al. |
| 7,462,350 | B2 | 12/2008 | Gillies et al. |
| 7,465,447 | B2 | 12/2008 | Gillies et al. |
| 7,507,406 | B2 | 3/2009 | Gillies et al. |
| 7,517,526 | B2 | 4/2009 | Gillies et al. |
| 2001/0053539 | A1 | 12/2001 | Lauffer et al. |
| 2002/0037558 | A1 | 3/2002 | Lo et al. |
| 2002/0081664 | A1 | 6/2002 | Lo et al. |
| 2002/0142374 | A1 | 10/2002 | Gallo et al. |
| 2002/0146388 | A1 | 10/2002 | Gillies |
| 2002/0147311 | A1 | 10/2002 | Gillies et al. |
| 2002/0192222 | A1 | 12/2002 | Blumberg et al. |
| 2002/0193570 | A1 | 12/2002 | Gillies et al. |
| 2003/0003529 | A1 | 1/2003 | Bayer |
| 2003/0012789 | A1 | 1/2003 | Blumberg et al. |
| 2003/0044423 | A1 | 3/2003 | Gillies et al. |
| 2003/0049227 | A1 | 3/2003 | Gillies et al. |
| 2003/0105294 | A1 | 6/2003 | Gillies et al. |
| 2003/0139365 | A1 | 7/2003 | Lo et al. |
| 2003/0139575 | A1 | 7/2003 | Gillies |
| 2003/0157054 | A1 | 8/2003 | Gillies et al. |
| 2003/0166163 | A1 | 9/2003 | Gillies |
| 2003/0166877 | A1 | 9/2003 | Gillies et al. |
| 2004/0013640 | A1 | 1/2004 | Zardi et al. |
| 2004/0033210 | A1 | 2/2004 | Gillies |
| 2004/0043457 | A1 | 3/2004 | Schumacher et al. |
| 2004/0053366 | A1 | 3/2004 | Lo et al. |
| 2004/0072299 | A1 | 4/2004 | Gillies et al. |
| 2004/0082039 | A1 | 4/2004 | Gillies et al. |
| 2004/0180035 | A1 | 9/2004 | Gillies et al. |
| 2004/0180386 | A1 | 9/2004 | Carr et al. |
| 2004/0203100 | A1 | 10/2004 | Gillies et al. |
| 2005/0042729 | A1 | 2/2005 | Gillies et al. |
| 2005/0054052 | A1 | 3/2005 | Carr et al. |
| 2005/0069521 | A1 | 3/2005 | Gillies et al. |
| 2005/0137384 | A1 | 6/2005 | Gillies et al. |
| 2005/0164352 | A1 | 7/2005 | Lauder et al. |
| 2005/0192211 | A1 | 9/2005 | Lauder et al. |
| 2005/0202021 | A1 | 9/2005 | Gillies |
| 2005/0202538 | A1 | 9/2005 | Gillies et al. |
| 2005/0244418 | A1 | 11/2005 | Gillies et al. |
| 2005/0261229 | A1 | 11/2005 | Gillies et al. |
| 2006/0025573 | A1 | 2/2006 | Gillies et al. |
| 2006/0034836 | A1 | 2/2006 | Gillies et al. |
| 2006/0141581 | A1 | 6/2006 | Gillies et al. |
| 2006/0194952 | A1 | 8/2006 | Gillies et al. |
| 2006/0228332 | A1 | 10/2006 | Gillies et al. |
| 2006/0263856 | A1 | 11/2006 | Gillies et al. |
| 2007/0036752 | A1 | 2/2007 | Gillies et al. |
| 2007/0059282 | A1 | 3/2007 | Gillies et al. |
| 2007/0104689 | A1 | 5/2007 | Gillies et al. |
| 2007/0154453 | A1 | 7/2007 | Webster et al. |
| 2007/0154473 | A1 | 7/2007 | Super et al. |
| 2007/0178098 | A1 | 8/2007 | Way et al. |
| 2007/0258944 | A1 | 11/2007 | Gillies et al. |
| 2007/0287170 | A1 | 12/2007 | Davis et al. |
| 2008/0025947 | A1 | 1/2008 | Gillies et al. |
| 2008/0311655 | A1 | 12/2008 | Gillies et al. |
| 2009/0010875 | A1 | 1/2009 | Lauder et al. |
| 2009/0043076 | A1* | 2/2009 | Carr et al. .................... 530/351 |
| 2009/0088561 | A1 | 4/2009 | Gillies et al. |
| 2009/0092607 | A1 | 4/2009 | Gillies et al. |
| 2009/0098609 | A1 | 4/2009 | Gillies et al. |

FOREIGN PATENT DOCUMENTS

| | | | |
|---|---|---|---|
| EP | 0 294 703 | A2 | 12/1988 |
| EP | 0 308 936 | B1 | 3/1989 |
| EP | 0 314 317 | B1 | 5/1989 |
| EP | 0 318 554 | B1 | 6/1989 |
| EP | 0 326 120 | B1 | 8/1989 |
| EP | 0 350 230 | A2 | 1/1990 |
| EP | 0 375 562 | B1 | 6/1990 |
| EP | 0 396 387 | A2 | 11/1990 |
| EP | 0 439 095 | A2 | 7/1991 |
| EP | 0 511 747 | A1 | 11/1992 |
| EP | 0 601 043 | B1 | 6/1994 |
| EP | 0 428 596 | B1 | 4/1996 |
| EP | 0 706 799 | A2 | 4/1996 |
| EP | 1 088 888 | A1 | 4/2001 |
| JP | 63-267278 | | 11/1988 |
| JP | 63-267296 | | 11/1988 |
| WO | WO 86/01533 | | 3/1986 |
| WO | WO 88/00052 | | 1/1988 |
| WO | WO 89/02922 | | 4/1989 |
| WO | WO 91/00360 | | 1/1991 |
| WO | WO 91/08298 | | 6/1991 |
| WO | WO 91/13166 | | 9/1991 |
| WO | WO 91/14438 | | 10/1991 |
| WO | WO 92/02240 | | 2/1992 |
| WO | WO 92/08495 | | 5/1992 |
| WO | WO 92/08801 | | 5/1992 |
| WO | WO 92/10755 | | 6/1992 |
| WO | WO 92/16562 | | 10/1992 |
| WO | WO 93/03157 | | 2/1993 |
| WO | WO 94/25609 | | 11/1994 |
| WO | WO 95/05468 | | 2/1995 |
| WO | WO 95/21258 | | 8/1995 |
| WO | WO 95/31483 | | 11/1995 |
| WO | WO 96/04388 | | 2/1996 |
| WO | WO 96/08570 | | 3/1996 |
| WO | WO 96/18412 | | 6/1996 |
| WO | WO 96/40792 | | 12/1996 |
| WO | WO 97/00317 | | 1/1997 |
| WO | WO 97/00319 | | 1/1997 |
| WO | WO 97/24137 | | 7/1997 |
| WO | WO 97/24440 | | 7/1997 |
| WO | WO 97/30089 | | 8/1997 |
| WO | WO 97/33617 | | 9/1997 |
| WO | WO 97/33619 | | 9/1997 |
| WO | WO 97/34631 | | 9/1997 |
| WO | WO 97/43316 | | 11/1997 |
| WO | WO 98/00127 | | 1/1998 |
| WO | WO 98/28427 | | 7/1998 |
| WO | WO 98/30706 | | 7/1998 |
| WO | WO 98/46257 | | 10/1998 |
| WO | WO 98/52976 | | 11/1998 |
| WO | WO 99/02709 | | 1/1999 |
| WO | WO 99/03887 | | 1/1999 |
| WO | WO 99/29732 | | 6/1999 |
| WO | WO 99/43713 | | 9/1999 |
| WO | WO 99/52562 | | 10/1999 |
| WO | WO 99/53958 | | 10/1999 |
| WO | WO 00/11033 | | 3/2000 |
| WO | WO 00/23472 | | 4/2000 |
| WO | WO 00/34317 | | 6/2000 |
| WO | WO 00/40615 | | 7/2000 |
| WO | WO 00/69913 | | 11/2000 |
| WO | WO 01/07081 | | 2/2001 |
| WO | WO 01/10912 | | 2/2001 |
| WO | WO 01/36489 | | 5/2001 |
| WO | WO 01/58957 | | 8/2001 |
| WO | WO 01/03737 | | 1/2002 |
| WO | WO 02/02143 | | 1/2002 |
| WO | WO 02/066514 | | 8/2002 |
| WO | WO 02/072605 | | 9/2002 |
| WO | WO 02/074783 | | 9/2002 |
| WO | WO 02/079232 | | 10/2002 |
| WO | WO 02/079415 | | 10/2002 |
| WO | WO 02/090566 | | 11/2002 |
| WO | WO 03/015697 | | 2/2003 |
| WO | WO 03/048334 | | 6/2003 |
| WO | WO 03/077834 | | 9/2003 |

OTHER PUBLICATIONS

Bitonti et al., (2002), "Transepithelial Absorption of an Erythropoietin-Fc Fusion Protein After Delivery to the Central Airways," *Respiratory Drug Delivery*, 8:309-312.

Bjorn et al., (1985), "Evaluation of Monoclonal Antibodies for the Development of Breast Cancer Immunotoxins," *Cancer Research*, 45:1214-1221.

(56) References Cited

OTHER PUBLICATIONS

Boulianne et al., (1984), "Production of Functional Chimaeric Mouse/Human Antibody," *Nature*, 312:643-6.
Bubenik et al., (1995), "Interleukin-2 Gene Therapy of Residual EL-4 Leukaemia Potentiates the Effect of Cyclophosphamide Pretreatment," *J. Cancer Res. Clin. Oncol.*, 121:39-43.
Burgess et al., (1990), "Possible Dissociation of the Heparin-Binding and Mitogenic Activities of Heparin-Binding (Acidic Fibroblast) Growth Factor-1 from Its Receptor-Binding Activities by Site-Directed Mutagenesis of a Single Lysine Residue," *Journal of Cell Biology*, 111:2129-2138.
Capon et al., (1989), "Designing CD4 Immunoadhesins for AIDS Therapy," *Nature*, 337:525-531.
Caton et al., (1986), "Structural and Functional Implications of a Restricted Antibody Response to a Defined Antigenic Region on the Influenza Virus Hemagglutinin," *The EMBO Journal*, 5(7):1577-1587.
Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," J. Immunol., 148:92-98.
Chaudhary et al., (1988), "Selective Killing of HIV-Infected Cells by Recombinant Human CD4-*Pseudomonas* Exotoxin Hybrid Protein," *Nature*, 335:370-372.
Chaudhary et al., (1989), "A Recombinant Immunotoxin Consisting of Two Antibody Variable Domains Fused to *Pseudomonas* Exotoxin," *Nature*, 339:394-397.
Cheon et al., (1994), "High-Affinity Binding Sites for Related Fibroblast Growth Factor Ligands Reside Within Different Receptor Immunoglobulin-Like Domains," *Proc. Natl. Acad. Sci. USA*, 91: 989-993.
Cohen et al., (1998), "An Artificial Cell-Cycle Inhibitor Isolated from a Combinatorial Library," *Proc. Natl. Acad. Sci. USA*, 95:14272-7.
Connor et al., (2004), "Ex vivo Evaluation of Anti-EpCAM Immunocytokine huKS-IL2 in Ovarian Cancer," *J. Immunotherapy*, 27:211-219.
Cruse et al., (eds.), (1995), Illustrated Dictionary of Immunology, pp. 156-158, CRC Press, NY.
Davis et al., (2003), "Immunocytokines: Amplification of Anti-Cancer Immunity," *Cancer Immunol. Immunother.*, 52:297-308.
Dolman et al., (1998), "Suppression of Human Prostate Carcinoma Metastases in Severe Combined Immunodeficient Mice by Interleukin 2 Immunocytokine Therapy," *Clin. Cancer Research.*, 4(10):2551-2557.
Fell et al., (1991), "Genetic Construction and Characterization of a Fusion Protein Consisting of a Chimeric F(ab') with Specificity for Carcinomas and Human IL-2," *J. Immunology*, 146(7):2446-2452.
Fell et al., (1992), "Chimeric L6 Anti-Tumor Antibody: Genomic Construction, Expression, and Characterization of the Antigen Binding Site," *J. Biological Chemistry*, 267:15552-15558.
Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.
Gan et al., (1999), "Specific Enzyme-Linked Immunosorbent Assays for Quantitation of Antibody-Cytokine Fusion Proteins," *Clinical and Diagnostic Laboratory Immunology*, 6(2):236-42.
Gasson et al., (1984), "Purified Human Granulocyte Macrophage Colony-Stimulating Factor: Direct Action on Neutrophils," *Science*, 226:1339-1342.
Gillies et al., (1989), "Expression of Human Anti-Tetanus Toxoid Antibody in Transfected Murine Myeloma Cells," *Bio/Technology*, 7:799-804.
Gillies et al., (1989), "High-Level Expression of Chimeric Antibodies Using Adapted cDNA Variable Region Cassettes," *J. Immunol. Methods*, 125:191-202.
Gillies et al., (1990), "Antigen Binding and Biological Activities of Engineered Mutant Chimeric Antibodies with Human Tumor Specificities," *Hum. Antibod. Hybridomas*, 1(1):47-54.
Gillies et al., (1991), "Expression of Genetically Engineered Immunoconjugates of Lymphotoxin and a Chimeric Anti-Ganglioside GD2 Antibody," *Hybridoma.*, 10(3):347-56.
Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.
Gillies et al., (1992), "Antibody-Targeted Interleukin 2 Stimulates T-Cell Killing of Autologous Tumor Cells," *Proc. Natl. Acad. Sci. USA*, 89:1428-1432.
Gillies et al., (1993), "Biological Activity and in Vivo Clearance of Antitumor Antibody/Cytokine Fusion Proteins," *Bioconjugate Chem.*, 4(3):230-235.
Gillies et al., (1998), "Antibody-IL-12 Fusion Proteins are Effective in SCID Mouse Models of Prostate and Colon Carcinoma Metastases," *J. Immunology*, 160:6195-6203.
Gillies et al., (1999), "Improving the Efficacy of Antibody-Interleukin 2 Fusion Proteins by Reducing Their Interaction with Fc Receptors," *Cancer Research*, 59:2159-2166.
Gillies et al., (2002), "Bi-Functional Cytokine Fusion Proteins for Gene Therapy and Antibody-Targeted Treatment of Cancer," *Cancer Immunol. Immunother.*, 51(8):449-60.
Gillies et al., (2002), "Improved Circulating Half-Life and Efficacy of an Antibody-Interleukin 2 Immunocytokine Based on Reduced Intracellular Proteolysis," *Clin. Cancer Research*, 8(1):210-216.
Goeddel et al., (1986), "Tumor Necrosis Factors: Gene Structure and Biological Activities," *Cold Spring Harb. Symp. Quant. Biol.*, 51:597-609.
Gren et al., (1983), "A New Type of Leukocytic Interferon," English Translation of *Dokl. Akad. Nauk. SSSR.*, 269(4):986-990.
Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73(8):2081-2085.
Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest.*, 82:1956-1962.
Guyre et al., (1997), "Increased Potency of Fc-Receptor-Targeted Antigens," *Cancer Immunol. Immunother.*, 45:146-148.
Halin et al., (2002), "Enhancement of the Antitumor Activity of Interleukin-12 by Targeted Delivery to Neovasculature," *Nature Biotechnology*, 20:264-269.
Hank et al., (1996), "Activation of Human Effector Cells by a Tumor Reactive Recombinant Anti-Ganglioside GD2 Interleukin-2 Fusion Protein (ch14.18-IL2)," *Clin Cancer Research*, 2(12):1951-1959.
Hank et al., (2003), "Determination of Peak Serum Levels and Immune Response to the Humanized Anti-Ganglioside Antibody-Interleukin-2 Immunocytokine," in *Methods in Molecular Medicine, 85: Novel Anticancer Drug Protocols*, Buolamwini et al., (eds.), pp. 123-131, Humana Press Inc., Totowana, NJ.
Harris et al., (1993), "Therapeutic Antibodies—The Coming of Age," *Trends in Biotechnology*, 11:42-44.
Harris, (1995), "Processing of C-Terminal Lysine and Arginine Residues of Proteins Isolated from Mammalian Cell Culture," *J. Chromatography A*, 705:129-134.
Harvill et al., (1995), "An IgG3-IL2 Fusion Protein Activates Complement, Binds FcγRl, Generates LAK Activity and Shows Enhanced Binding to the High Affinity IL-2R," *Immunotechnology*, 1:95-105.
Harvill et al., (1996), "In Vivo Properties of an IgG3-IL-2 Fusion Protein: A General Strategy for Immune Potentiation," *J. Immunology*, 157(7):3165-3170.
He et al., (1998), "Humanization and Pharmacokinetics of a Monoclonal Antibody with Specificity for Both E- and P-Selectin," *J. Immunology*, 160:1029-1035.
Henkart, (1985), "Mechanism of Lymphocyte-Mediated Cytotoxicity," *Ann. Rev. Immunol.*, 3:31-58.
Herrmann et al., (1989), "Hematopoietic Responses With Advanced Malignancy Treated With Recombinant Human Granulocyte-Macrophage Colony-Stimulating Factor," *Journal of Clinical Oncology*, 7(2):159-167.

(56) References Cited

OTHER PUBLICATIONS

Hezareh et al., (2001), "Effector Function Activities of a Panel of Mutants of a Broadly Neutralizing Antibody against Human Immunodeficiency Virus Type 1," *J. Virology*, 75(24):12161-12168.
Holden et al., (2001), "Augmentation of Antitumor Activity of an Antibody-Interleukin 2 Immunocytokine with Chemotherapeutic Agents," *Clinical Cancer Research*, 7:2862-2869.
Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675 (XP-002195344).
Hoogenboom et al., (1991), "Construction and Expression of Antibody-Tumor Necrosis Factor Fusion Proteins," *Molecular Immunology*, 28(9):1027-1037.
Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," *Biochim. Biophys. Acta*, 1096(4):345-354 (Abstract).
Hornick et al., (1999), "Pretreatment with a Monoclonal Antibody/Interleukin-2 Fusion Protein Directed Against DNA Enhances the Delivery of Therapeutic Molecules to Solid Tumors," *Clin. Cancer Research*, 5:51-60.
Hurn et al., (1980), "Production of Reagent Antibodies," *Methods in Enzymology*, 70: 104-142.
Imboden et al., (2001), "The Level of MHC Class I Expression on Murine Adenocarcinoma Can Change the Antitumor Effector Mechanism of Immunocytokine Therapy," *Cancer Research*, 61(4):1500-7.
Jones et al., (2004), "The Development of a Modified Human IFN-α2b Linked to the Fc Portion of Human IgG1 as a Novel Potential Therapeutic for the Treatment of Hepatitis C Virus Infection," *J. Interferon and Cytokine Res*., 24:560-572.
Jung et al., (1986), "Activation of Human Peripheral Blood Mononuclear Cells by Anti-T3: Killing of Tumor Target Cells Coated with Anti-Target-Anti-T3 Conjugates," *Proc. Natl. Acad. Sci. USA*, 83:4479-4483.
Kappel et al., (1992), "Regulating Gene Expression in Transgenic Animals," *Current Opinion in Biotechnology*, 3:548-553.
Karpovsky et al., (1984), "Production of Target-Specific Effector Cells using Hetero-Cross Linked Aggregate Containing Anti-Target Cell and AntiFcγ Receptor Antibodies," *Journal of Experimental Medicine*, 1609(6):1686-1701.
Karpusas et al., (1997), "The Crystal Structure of Human Interferon β at 2.2-A Resolution," *Proc. Natl. Acad. Sci. USA*, 94:11813-11818.
Kendra et al., (1999), "Pharmacokinetics and Stability of the ch14.18-Interleukin-2 Fusion Protein in Mice," *Cancer Immunol. Immunother*., 48:219-229.
Kim et al., (1999), "Cytokine Molecular Adjuvants Modulate Immune Responses Induced by DNA Vaccine Constructs for HIV-1 and SIV," *Journal of Interferon and Cytokine Research*, 19:77-84.
King et al., (2004), "Phase I Clinical Trial of the Immunocytokine EMD 273063 in Melanoma Patients," *J. Clin. Oncol*., 22(22):4463-73.
Ko et al., (2004), "Safety, Pharmacokinetics, and Biological Pharmacodynamics of the Immunocytokine EMD 273066 (huKS-IL2)," *J. Immunotherapy*, 27:232-239.
Kranz et al., (1984), "Attachment of an Anti-Receptor Antibody to Non-Target Cells Renders Them Susceptible to Lysis by a Clone of Cytotoxic T Lymphocytes," *Proc. Natl. Acad. Sci. USA*, 81:7922-7926.
Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.
Lawn et al., (1981), "DNA Sequence of a Major Human Leukocyte Interferon Gene," *Proc. Natl. Acad. Sci. USA*, 78:5435-9.
Lazar et al., (1988), "Transforming Growth Factor α: Mutation of Aspartic Acid 47 and Leucine 48 Results in Different Biological Activities," *Molecular and Cellular Biology*, 8(3):1247-1252.
LeBerthon et al., (1991), "Enhanced Tumor Uptake of Macromolecules Induced by a Novel Vasoactive Interleukin 2 Immunoconjugate," *Cancer Research*, 51:2694-2698.
Linsley et al., (1991), "CTLA-4 is a Second Receptor for B Cell Activation Antigen B7," *J. Exp. Med*., 174(3):561-569.
Liu et al., (1985), "Heteroantibody Duplexes Target Cells for Lysis by Cytotoxic T Lymphocytes," *Proc. Natl. Acad. Sci. USA*, 82:8648-8652.
Liu et al., (1988), "Hormone Conjugated with Antibody to CD3 Mediates Cytotoxic T Cell Lysis of Human Melanoma Cells," *Science*, 239:395-398.
Lo et al. (2005), "Engineering a Pharmacologically Superior Form of Leptin for the Treatment of Obesity," *Protein Engineering, Design & Selection*, 18(1):1-10.
Lo et al., (1992), "Expression and Secretion of an Assembled Tetrameric CH2-Deleted Antibody in *E. coli*.," *Hum. Antibod. Hybridomas*, 3:123-128.
Lo et al., (1998), "High Level Expression and Secretion of Fc-X Fusion Proteins in Mammalian Cells," *Protein Engineering*, 11(6):495-500.
Lode et al., (1997), "Targeted Interleukin-2 Therapy for Spontaneous Neuroblastoma Metastases to Bone Marrow," *J. Natl. Cancer Inst*., 89(21):1586-94.
Lode et al., (1998), "Immunocytokines: A Promising Approach to Cancer Immunotherapy," *Pharmacol. Ther*., 80(3):277-292.
Lode et al., (1998), "Natural Killer Cell-Mediated Eradication of Neuroblastoma Metastases to Bone Marrow by Targeted Interleukin-2 Therapy," *Blood*, 91(5):1706-1715.
Lode et al., (1999), "Tumor-Targeted IL-2 Amplifies T Cell-Mediated Immune Response Induced by Gene Therapy with Single-Chain IL-12," *Proc. Natl. Acad. Sci. USA*, 96:8591-8596.
Lode et al., (2000), "Amplification of T Cell Mediated Immune Responses by Antibody-Cytokine Fusion Proteins," *Immunological Investigations*, 29(2):117-120.
Lode et al., (2000), "Melanoma Immunotherapy by Targeted IL-2 Depends on CD4(+) T-Cell Help Mediated by CD40/CD40L Interaction," *J. Clin. Invest*., 105(11):1623-30.
Lode et al., (2000), "What to Do With Targeted IL-2," *Drugs of Today*, 36(5):321-336.
MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother*., 19(4):309-316.
Mark et al., (1992), "Expression and Characterization of Hepatocyte Growth Factor Receptor-IgG Fusion Proteins," *Journal of Biological Chemistry*, 267(36):26166-26171.
Martin et al., (2001), "Crystal Structure at 2.8 Å of an FcRn/Heterodimeric Fc Complex: Mechanism of pH-Dependent Binding," *Mol. Cell*., 7(4):867-77.
McMahan et al., (1991), "A Novel IL-1 Receptor, Cloned From B-Cells by Mammalian Expression is Expressed in Many Cell Types," *EMBO J*., 10:2821-32.
Medesan et al., (1997), "Delineation of the Amino Acid Residues Involved in Transcytosis and Catabolism of Mouse IgG1," *J. Immunology*, 158(5):2211-2217.
Metelitsa et al., (2002), "Antidisialoganglioside/Granulocyte Macrophage-Colony-Stimulating Factor Fusion Protein Facilitates Neutrophil Antibody-Dependent Cellular Cytotoxicity and Depends on FcγRII (CD32) and Mac-1 (CD11b/CD18) for Enhanced Effector Cell Adhesion and Azurophil Granule Exocytosis," *Blood*, 99(11):4166-73.
Miyake et al., (1988), "Synthesis of Recombinant Human Single-Chain Urokinase-Type Plasminogen Activator Variants Resistant to Plasmin and Thrombin," *J. Biochem*., 104:643-647.
Morrison et al., (1984), "Chimeric Human Antibody Molecules: Mouse Antigen-Binding Domains with Human Constant Region Domains," *Proc. Natl. Acad. Sci. USA*, 81:6851-5.
Mueller et al., (1990), "Enhancement of Antibody-Dependent Cytotoxicity With a Chimeric Anti-GD2 Antibody," *J. Immunology*, 144(4):1382-1386.

(56) References Cited

OTHER PUBLICATIONS

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA.*, 87:5702-5705.
Mueller et al., (1997), "Humanized Porcine VCAM-Specific Monoclonal Antibodies with Chimeric IgG2/G4 Constant Regions Block Human Leukocyte Binding to Porcine Endothelial Cells," *Molecular Immunology*, 34(6):441-452.
Murphy et al., (1986), "Genetic Construction, Expression, and Melanoma-Selective Cytotoxicity of a Diphtheria Toxin-Related α-Melanocyte-Stimulating Hormone Fusion Protein," *Proc. Natl. Acad. Sci. USA*, 83:8258-8262.
Murphy, (1988), "Diphtheria-Related Peptide Hormone Gene Fusions: A Molecular Gene Approach to Chimeric Toxin Development," in *Immunotoxins*, pp. 123-140, Frankel (ed.), Kluwer Acad. Pub.
Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.
Naramura et al., (1994), "Mechanisms of Cellular Cytotoxicity Mediated by a Recombinant Antibody-IL2 Fusion Protein Against Human Melanoma Cells," *Immunology Letters*, 39:91-99.
Nastala et al., (1994), "Recombinant IL-12 Administration Induces Tumor Regression in Association with IFN-γ Production," *J. Immunol.*, 153:1697-706.
Neal et al., (2003), "NXS2 Murine Neuroblastomas Express Increased Levels of MHC Class I Antigens upon Recurrence Following NK-Dependent Immunotherapy," *Cancer Immunol. Immunother.*, 53:41-52.
Neal et al., (2004), "Enhanced Activity of Hu14.18-IL2 Immunocytokine against Murine NXS2 Neuroblastoma when Combined with Interleukin-2 Therapy," *Clin. Cancer. Res.*, 10:4839-4847.
Nedwin et al., (1985), "Human Lymphotoxin and Tumor Necrosis Factor Genes: Structure, Homology and Chromosomal Localization," *Nucleic Acids Research*, 13(17):6361-6373.
Nelles et al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.
Neuberger et al., (1984), "Recombinant Antibodies Possessing Novel Effector Functions," *Nature*, 312:604-608.
Ngo et al., (1994), "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.
Niethammer et al., (2001) "Targeted Interleukin 2 Therapy Enhances Protective Immunity Induced by an Autologous Oral DNA Vaccine against Murine Melanoma," *Cancer Research*, 61(16):6178-84.
Pancook et al., (1996), "Eradication of Established Hepatic Human Neuroblastoma Metastases in Mice with Severe Combined Immunodeficiency by Antibody-Targeted Interleukin-2," *Cancer Immunol. Immunother.*, 42(2):88-92.
Pedley et al. (1999), "Enhancement of Antibody-Directed Enzyme Prodrug Therapy in Colorectal Xenografts by an Antivascular Agent," *Cancer Res.*, 59:3998-4003.
Perez et al., (1986), "Specific Targeting of Human Peripheral Blood T Cells by Heteroaggregates Containing Anti-T3 Crosslinked to Anti-Target Cell Antibodies," *J. Exp. Med.*, 163:166-178.
Poon et al., (1995), "Structure and Function of Several Anti-Dansyl Chimeric Antibodies Formed by Domain Interchanges Between Human IgM and Mouse IgG2b," *J. Biol. Chem.*, 270:8571-7.
Radhakrishnan et al., (1996), "Zinc Mediated Dimer of Human Interferon-$\alpha_{2b}$ Revealed by X-Ray Crystallography," *Structure* 4(12):1453-63.
Reisfeld et al., (1996), "Antibody-Interleukin 2 Fusion Proteins: A New Approach to Cancer Therapy," *J. Clin. Lab. Anal.*, 10:160-166.
Reisfeld et al., (1996), "Involvement of B Lymphocytes in the Growth Inhibition of Human Pulmonary Melanoma Metastases in Athymic *nu/nu* Mice by an Antibody-Lymphotoxin Fusion Protein," *Cancer Research*, 56(8):1707-1712.
Reisfeld et al., (1996), "Recombinant Antibody Fusion Proteins for Cancer Immunotherapy," *Current Topics in Microbiology and Immunology*, 213:27-53.
Reisfeld et al., (1997), "Immunocytokines: A New Approach to Immunotherapy of Melanoma," *Melanoma Research*, 7(Supp2):S99-S106.
Rosenberg, (1988), "Immunotherapy of Cancer Using Interleukin 2: Current Status and Future Prospects," *Immunology Today*, 9(2):58-62.
Ruehlmann et al., (2001), "MIG (CXCL9) Chemokine Gene Therapy Combines with Antibody-Cytokine Fusion Protein to Suppress Growth and Dissemination of Murine Colon Carcinoma," *Cancer Research*, 61(23):8498-503.
Runkel et al., (1998), "Structural and Functional Differences Between Glycosylated and Non-Glycosylated Forms of Human Interferon-β (IFN-β)," *Pharmaceutical Res.*, 15:641-649.
Sabzevari et al., (1994), "A Recombinant Antibody-Interleukin 2 Fusion Protein Suppresses Growth of Hepatic Human Severe Combined Immunodeficiency Mice," *Proc. Natl. Acad. Sci. USA*, 91(20):9626-30.
Sakano et al., (1980), "Two Types of Somatic Recombination are Necessary for the Generation of Complete Immunoglobin Heavy-Chain Genes," *Nature*, 286:676-683.
Schnee et al., (1987), "Construction and Expression of a Recombinant Antibody-Targeted Plasminogen Activator," *Proc. Natl. Acad. Sci. USA*, 84:6904-6908.
Senior et al., (2000), "Cleavage of a Recombinant Human Immunoglobulin A2 (igA2)-IgA1 Hybrid Antibody by Certain Bacterial IgA1 Proteases," *Infect. Immun.*, 68(2):463-9.
Senter et al., (1988), "Anti-Tumor Effects of Antibody-Alkaline Phosphatase Conjugates in Combination with Etoposide Phosphate," *Proc. Natl. Acad. Sci. USA*, 85(13):4842-4846.
Shin et al., (1990), "Expression and Characterization of an Antibody Binding Specificity Joined to Insulin-Like Growth Factor 1: Potential Applications for Cellular Targeting," *Proc. Natl. Acad. Sci. USA*, 87:5322-5326.
Shinkawa et al., (2003), "The Absence of Fucose But Not the Presence of Galactose or Bisecting N-Acetylglucosamine of Human IgG1 Complex-Type Oligosaccharides Shows the Critical Role of Enhancing Antibody-Dependent Cellular Cytotoxicity," *J. Biol. Chem.*, 278:3466-3473.
Spiekermann et al., (2002), "Receptor-Mediated Immunoglobulin G Transport Across Mucosal Barriers in Adult Life: Functional Expression of FcRn in the Mammalian Lung," *J. Exp. Med.*, 196:303-310.
Stevenson et al., (1997), "Conjugation of Human Fcγ in Closed-Hinge or Open-Hinge Configuration to Fab'γ and Analogous Ligands," *J. Immunology*, 158:2242-2250.
Takai, (2002), "Roles of Fc Receptors in Autoimmunity," *Nat. Rev. Immunol.*, 2(8):580-92.
Taniguchi et al., (1980), "Expression of the Human Fibroblast Interferon Gene in *Escherichia coli," Proc. Natl. Acad. Sci. USA*, 77:5230-5233.
Tao et al., (1989), "Studies of Aglycosylated Chimeric Mouse IgG: Role of Carbohydrate in the Structure and Effector Functions Mediated by the Human IgG Constant Region," *J. Immunology*, 143(8):2595-2601.
Tao et al., (1993), "Structural Features of Human Immunoglobulin G that Determine Isotype-Differences in Complement Activation," *J. Exp. Med.*, 178(2):661-667.
Thommesen et al., (2000), "Lysine 322 in the Human IgG3 CH2 Domain is Crucial for Antibody Dependent Complement Activation," *Mol. Immunol.*, 37(16):995-1004.
Till et al., (1988), "An Assay that Predicts the Ability of Monoclonal Antibodies to Form Potent Ricin A Chain-Containing Immunotoxins," *Cancer Research*, 48(5):1119-1123.
Till et al., (1988), "HIV-Infected Cells are Killed by rCD4-Ricin A Chain," *Science*, 242:1166-1168.
Verhoeyen et al., (1988), "Reshaping Human Antibodies: Grafting an Antilysozyme Activity," *Science*, 239:1534-36.
Ward et al., (1995), "The Effector Functions of Immunoglobulins: Implications for Therapy," *Therapeutic. Immunology*, 2:77-94.

(56) References Cited

OTHER PUBLICATIONS

Williams et al., (1986), "Production of Antibody-Tagged Enzymes by Myeloma Cells: Application to DNA Polymerase I Klenow Fragment," *Gene*, 43:319-324.
Woof et al., (1986), "Localisation of the Monocyte-Binding Region on Human Immunoglobulin G," *Mol. Immunol.*, 23:319-30.
Wooley et al., (1993), "Influence of a Recombinant Human Soluble Tumor Necrosis Factor Receptor Fc Fusion Protein on Type II Collagen-Induced Arthritis in Mice," *J. Immunology*, 151:6602-6607.
Xiang et al., (1997), "Elimination of Established Murine Colon Carcinoma Metastases by Antibody-Interleukin 2 Fusion Protein Therapy," *Cancer Research*, 57:4948-4955.
Xu et al., (1994), "Residue at Position 331 in the IgG1 and IgG4 CH2 Domains Contributes to Their Differential Ability to Bind and Activate Complement," *J. Biol. Chem.*, 269(5):3469-3474.
Zheng et al., (1995), "Administration of Noncytolytic IL-10/Fc in Murine Models of Lipopolysaccharide-Induced Septic Shock and Allogeneic Islet Transplantation," *Journal of Immunol.*, 154:5590-5600.
Zhu et al., (2001), "MHC Class I-Related Neonatal Fc Receptor for IgG is Functionally Expressed in Monocytes, Intestinal Macrophages and Dendritic Cells," *J. Immunol.*, 166:3266-3276.
Zuckier et al., (1998), "Chimeric Human-Mouse IgG Antibodies with Shuffled Constant Region Exons Demonstrate that Multiple Domains Contribute to in Vivo Half-Life," *Cancer Res.*, 58(17):3905-8.
Lode et al., (1999), "Synergy Between an Antiangiogenic Integrin $\alpha_V$ Antagonist and an Antibody-Cytokine Fusion Protein Eradicates Spontaneous Tumor Metastases," *Proc. Natl. Acad. Sci. USA*, 96:1591-1596.
Cole et al., (1997), "Human IgG2 Variants of Chimeric Anti-CD3 are Non-Mitogenic to T-Cells," *J. Immunol.*, 159(7):3613-21.
Day et al., (1992), "Engineered Disulfide Bond Greatly Increases Specific Activity of Recombinant Murine Interferon-Beta," *J. Interferon Res.*, 12(2):139-143.
Runkel et al., (2000), "Systematic Mutational Mapping of Sites on Human Interferon-Beta-1a that are Important for Receptor Binding and Functional Activity," *Biochemistry*, 39(10):2538-2551.
Stewart et al., (1987), "Chemical Mutagenesis of Human Interferon-Beta: Construction, Expression in *E. coli*, and Biological Activity of Sodium Bisulfite-Induced Mutations," *DNA*, 6(2):119-128.
International Search Report for International Application No. PCT/EP2005/006925, mailed Dec. 19, 2005 (5 pages).
Written Opinion of the International Searching Authority for International Application No. PCT/EP2005/006925, mailed Dec. 19, 2005 (5 pages).
Stickler et al., (2004), "The HLA-DR2 Haplotype is Associated with an Increased Proliferative Response to the Immunodominant CD4 + T-Cell Epitope in Human Interferon-$\gamma$," *Genes and Immunity* 5:1-7.
Mickle et al., (2000), "Genotype-Phenotype Relationships in Cystic Fibrosis," *Med. Clin. North. Am.* 84: 597-607.

* cited by examiner

Mature human IFN-β:

```
MSYNLLGFLQ RSSNFQCQKL LWQLNGRLEY CLKDRMNFDI PEEIKQLQQF      50

QKEDAALTIY EMLQNIFAIF RQDSSSTGWN ETIVENLLAN VYHQINHLKT      100

VLEEKLEKED FTRGKLMSSL HLKRYYGRIL HYLKAKEYSH CAWTIVRVEI      150

LRNFYFINRL TGYLRN 166

(SEQ ID NO:2)
```

FIG. 3

Mature human IFN-β(C17S):

```
MSYNLLGFLQ RSSNFQSQKL LWQLNGRLEY CLKDRMNFDI PEEIKQLQQF      50

QKEDAALTIY EMLQNIFAIF RQDSSSTGWN ETIVENLLAN VYHQINHLKT      100

VLEEKLEKED FTRGKLMSSL HLKRYYGRIL HYLKAKEYSH CAWTIVRVEI      150

LRNFYFINRL TGYLRN 166

(SEQ ID NO:3)
```

FIG. 4

Human Fcγ4h-IFN-β(C17S), γ4 isotype and modified γ1 hinge:

```
EPKSSDKTHT CPPCPAPEFL GGPSVFLFPP KPKDTLMISR TPEVTCVVVD       50

VSQEDPEVQF NWYVDGVEVH NAKTKPREEQ FNSTYRVVSV LTVLHQDWLN      100

GKEYKCKVSN KGLPSSIEKT ISKAKGQPRE PQVYTLPPSQ EEMTKNQVSL      150

TCLVKGFYPS DIAVEWESNG QPENNYKTTP PVLDSDGSFF LYSKLTVDKS      200

RWQQGNIFSC SVMHEALHNH YTQKSLSLSP GMSYNLLGFL QRSSNFQSQK      250

LLWQLNGRLE YCLKDRMNFD IPEEIKQLQQ FQKEDAALTI YEMLQNIFAI      300

FRQDSSSTGW NETIVENLLA NVYHQINHLK TVLEEKLEKE DFTRGKLMSS      350

LHLKRYYGRI LHYLKAKEYS HCAWTIVRVE ILRNFYFINR LTGYLRN   397

(SEQ ID NO:4)
```

FIG. 5

Human Fc-(linker)-IFN-β, starting with the CH3 domain of the Fcγ4 isotype:

```
GQPREPQVYT LPPSQEEMTK NQVSLTCLVK GFYPSDIAVE WESNGQPENN      50
YKTTPPVLDS DGSFFLYSKL TVDKSRWQQG NIFSCSVMHE ALHNHYTQKS     100
LSLSPGAGGG GSGGGGSGGG SGMSYNLLGF LQRSSNFQCQ KLLWQLNGRL     150
EYCLKDRMNF DIPEEIKQLQ QFQKEDAALT IYEMLQNIFA IFRQDSSSTG     200
WNETIVENLL ANVYHQINHL KTVLEEKLEK EDFTRGKLMS SLHLKRYYGR     250
ILHYLKAKEY SHCAWTIVRV EILRNFYFIN RLTGYLRN 288
(SEQ ID NO:5)
```

FIG. 6

Human Fc-(linker)-IFN-β(C17S), starting with the CH3 domain of the Fcγ4 isotype:

```
GQPREPQVYT LPPSQEEMTK NQVSLTCLVK GFYPSDIAVE WESNGQPENN    50
YKTTPPVLDS DGSFFLYSKL TVDKSRWQQG NIFSCSVMHE ALHNHYTQKS    100
LSLSPGAGGG GSGGGGSGGG SGMSYNLLGF LQRSSNFQSQ KLLWQLNGRL    150
EYCLKDRMNF DIPEEIKQLQ QFQKEDAALT IYEMLQNIFA IFRQDSSSTG    200
WNETIVENLL ANVYHQINHL KTVLEEKLEK EDFTRGKLMS SLHLKRYYGR    250
ILHYLKAKEY SHCAWTIVRV EILRNFYFIN RLTGYLRN 288
(SEQ ID NO:6)
```

FIG. 7

Human Fc-(linker)-IFN-β(C17S, L57A, H131A, H140T), starting with the CH3 domain of the Fcγ4 isotype:

```
GQPREPQVYT LPPSQEEMTK NQVSLTCLVK GFYPSDIAVE WESNGQPENN      50
YKTTPPVLDS DGSFFLYSKL TVDKSRWQQG NIFSCSVMHE ALHNHYTQKS      100
LSLSPGAGGG GSGGGGSGGG SGMSYNLLGF LQRSSNFQSQ KLLWQLNGRL      150
EYCLKDRMNF DIPEEIKQLQ QFQKEDAAAT IYEMLQNIFA IFRQDSSSTG      200
WNETIVENLL ANVYHQINHL KTVLEEKLEK EDFTRGKLMS SLHLKRYYGR      250
ILAYLKAKEY STCAWTIVRV EILRNFYFIN RLTGYLRN 298
```

(SEQ ID NO:7)

FIG. 8

Human Fc-(linker)-IFN-β(C17S, L57A, H131A, H140A), starting with the CH3 domain of Fcγ4 isotype:

```
GQPREPQVYT LPPSQEEMTK NQVSLTCLVK GFYPSDIAVE WESNGQPENN      50
YKTTPPVLDS DGSFFLYSKL TVDKSRWQQG NIFSCSVMHE ALHNHYTQKS      100
LSLSPGAGGG GSGGGGSGGG SGMSYNLLGF LQRSSNFQSQ KLLWQLNGRL      150
EYCLKDRMNF DIPEEIKQLQ QFQKEDAAAT IYEMLQNIFA IFRQDSSSTG      200
WNETIVENLL ANVYHQINHL KTVLEEKLEK EDFTRGKLMS SLHLKRYYGR      250
ILAYLKAKEY SACAWTIVRV EILRNFYFIN RLTGYLRN 298
```

(SEQ ID NO:8)

FIG. 9

Human Fc-(linker)-IFN-β(C17S, F50A, H131A, H140A), starting with the CH3 domain of the Fcγ4 isotype:

```
YKTTPPVLDS DGSFFLYSKL TVDKSRWQQG NIFSCSVMHE ALHNHYTQKS      50
YKTTPPVLDS DGSFFLYSKL TVDKSRWQQG NVFSCSVMHE ALHNHYTQKS      100
LSLSPGAGGG GSGGGGSGGG SGMSYNLLGF LQRSSNFQSQ KLLWQLNGRL      150
EYCLKDRMNF DIPEEIKQLQ QAQKEDAALT IYEMLQNIFA IFRQDSSSTG      200
WNETIVENLL ANVYHQINHL KTVLEEKLEK EDFTRGKLMS SLHLKRYYGR      250
ILAYLKAKEY SACAWTIVRV EILRNFYFIN RLTGYLRN 298
(SEQ ID NO:9)
```

FIG. 10

Human Fc-(linker)-IFN-β(C17S, F50A, H131A, H140T), starting with the CH3 domain of the Fcγ4 isotype:

```
GQPREPQVYT LPPSQEEMTK NQVSLTCLVK GFYPSDIAVE WESNGQPENN     50
YKTTPPVLDS DGSFFLYSKL TVDKSRWQQG NIFSCSVMHE ALHNHYTQKS     100
LSLSPGAGGG GSGGGGSGGG SGMSYNLLGF LQRSSNFQSQ KLLWQLNGRL     150
EYCLKDRMNF DIPEEIKQLQ QAQKEDAALT IYEMLQNIFA IFRQDSSSTG     200
WNETIVENLL ANVYHQINHL KTVLEEKLEK EDFTRGKLMS SLHLKRYYGR     250
ILAYLKAKEY STCAWTIVRV EILRNFYFIN RLTGYLRN 298
(SEQ ID NO:10)
```

FIG. 11

Mature mouse IFN-β:

INYKQLQLQE RTNIRKCQEL LEQLNGKINL TYRADFKIPM EMTEKMQKSY 50

TAFAIQEMLQ NVFLVFRNNF SSTGWNETIV VRLLDELHQQ TVFLKTVLEE 100

KQEERLTWEM SSTALHLKSY YWRVQRYLKL MKYNSYAWMV VRAEIFRNFL 150

IIRRLTRNFQ N 161

(SEQ ID NO:11)

FIG. 12

Mature mouse IFN-β(C17S):

INYKQLQLQE RTNIRKSQEL LEQLNGKINL TYRADFKIPM EMTEKMQKSY 50

TAFAIQEMLQ NVFLVFRNNF SSTGWNETIV VRLLDELHQQ TVFLKTVLEE 100

KQEERLTWEM SSTALHLKSY YWRVQRYLKL MKYNSYAWMV VRAEIFRNFL 150

IIRRLTRNFQ N 161

(SEQ ID NO:12)

FIG. 13

Human Fcγ4h-IFN-β(C17S) (γ4 isotype with modified γ1 hinge) nucleic acid sequence, starting from hinge:

GAGCCCAAATCTTCTGACAAAACTCACACATGCCCACCGTGCCCAGGTAAGCCAGCCCAGGCCTCGCCCTCCAGCTCA
AGGCGGGACAGGTGCCCTAGAGTAGCCTGCATCCAGGGACAGGCCCCAGCCGGGTGCTGACGCATCCACCTCCATCTC
TTCCTCAGCACCTGAGTTCCTGGGGGGACCATCAGTCTTCCTGTTCCCCCCAAAACCCAAGGACACTCTCATGATCTC
CCGGACCCCTGAGGTCACGTGCGTGGTGGTGGACGTGAGCCAGGAAGACCCCGAGGTCCAGTTCAACTGGTACGTGGA
TGGCGTGGAGGTGCATAATGCCAAGACAAAGCCGCGGGAGGAGCAGTTCAACAGCACGTACCGTGTGGTCAGCGTCCT
CACCGTCCTGCACCAGGACTGGCTGAACGGCAAGGAGTACAAGTGCAAGGTCTCCAACAAAGGCCTCCCGTCCTCCAT
CGAGAAAACCATCTCCAAAGCCAAAGGTGGGACCCACGGGGTGCGAGGGCCACATGGACAGAGGTCAGCTCGGCCCAC
CCTCTGCCCTGGGAGTGACCGCTGTGCCAACCTCTGTCCCTACAGGGCAGCCCCGAGAGCCACAGGTGTACACCCTGC
CCCCATCCCAGGAGGAGATGACCAAGAACCAGGTCAGCCTGACCTGCCTGGTCAAAGGCTTCTACCCCAGCGACATCG
CCGTGGAGTGGGAGAGCAATGGGCAGCCGGAGAACAACTACAAGACCACGCCTCCCGTGCTGGACTCCGACGGCTCCT
TCTTCCTCTACAGCAAGCTCACCGTGGACAAGAGCAGGTGGCAGCAGGGGAACATCTTCTCATGCTCCGTGATGCATG
AGGCTCTGCACAACCACTACACGCAGAAGAGCCTCTCCCTGTCCCCGGGTATGAGCTACAACTTGCTTGGATTCCTAC
AAAGAAGCAGCAATTTTCAGAGTCAGAAGCTCCTGTGGCAATTGAATGGGAGGCTTGAATATTGCCTCAAGGACAGGA
TGAACTTTGACATCCCTGAGGAGATTAAGCAGCTGCAGCAGTTCCAGAAGGAGGACGCCGCATTGACCATCTATGAGA
TGCTCCAGAACATCTTTGCTATTTTCAGACAAGATTCATCTAGCACTGGCTGGAATGAGACTATTGTTGAGAACCTCC
TGGCTAATGTCTATCATCAGATAAACCATCTGAAGACAGTCCTGGAAGAAAAACTGGAGAAAGAAGATTTCACCAGGG
GAAAACTCATGAGCAGTCTGCACCTGAAAAGATATTATGGGAGGATTCTGCATTACCTGAAGGCCAAGGAGTACAGTC
ACTGTGCCTGGACCATAGTCAGAGTGGAAATCCTAAGGAACTTTTACTTCATTAACAGACTTACAGGTTACCTCCGAA
ACTGA (SEQ ID NO:13)

FIG. 14

Linearized Nucleic Acid Sequence of pdCs Vector Containing huFcγ4h-linker-IFN-β(C17S) (γ4 isotype with modified γ1 hinge):

GTCGACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATGACGT
ATGTTCCCATAGTAACGCCAATAGGGACTTTCCATTGACGTCAATGGGTGGAGTATTTACGGTAAACTGCCCACTTGG
CAGTACATCAAGTGTATCATATGCCAAGTACGCCCCCTATTGACGTCAATGACGGTAAATGGCCCGCCTGGCATTATG
CCCAGTACATGACCTTATGGGACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAAGTCTCCACCCCATTGACGTCA
ATGGGAGTTTGTTTTGGCACCAAAATCAACGGGACTTTCCAAAATGTCGTAACAACTCCGCCCCATTGACGCAAATGG
GCGGTAGGCGTGTACGGTGGGAGGTCTATATAAGCAGAGCTCTCTGGCTAACTACAGAACCCACTGCTTACTGGCTTA
TCGAAATTAATACGACTCACTATAGGGAGACCCTCTAGACCACCATGGAGTTGCCTGTTAGGCTGTTGGTGCTGATGT
TCTGGATTCCTGGTGAGGAGAGAGGGAAGTGAGGGAGGAGAATGGACAGGGAGCAGGAGCACTGAATCCCATTGCTCA
TTCCATGTATCTGGCATGGGTGAGAAGATGGGTCTTATCCTCCAGCATGGGGCCTCTGGGGTGAATACTTGTTAGAGG
GAGGTTCCAGATGGGAACATGTGCTATAATGAAGATTATGAAATGGAGCCTGGGATGGTCTAAGTAATGCCTTAGAAG
TGACTAGACACTTGCAATTCACTTTTTTTGGTAAGAAGAGATTTTTAGGCTATAAAAAAATGTTATGTAAAAATAAAC
GATCACAGTTGAAATAAAAAAAAAATATAAGGATGTTCATGAATTTTGTGTATAACTATGTATTTCTCTCTCATTGTT
TCAGCTTCCTTAAGCGAGCCCAAATCTTCTGACAAAACTCACACATGCCCACCGTGCCCAGGTAAGCCAGCCCAGGCC
TCGCCCTCCAGCTCAAGGCGGGACAGGTGCCCTAGAGTAGCCTGCATCCAGGGACAGGCCCCAGCCGGGTGCTGACGC
ATCCACCTCCATCTCTTCCTCAGCACCTGAGTTCCTGGGGGGACCATCAGTCTTCCTGTTCCCCCCAAAACCCAAGGA
CACTCTCATGATCTCCCGGACCCCTGAGGTCACGTGCGTGGTGGTGGACGTGAGCCAGGAAGACCCCGAGGTCCAGTT
CAACTGGTACGTGGATGGCGTGGAGGTGCATAATGCCAAGACAAAGCCGCGGGAGGAGCAGTTCAACAGCACGTACCG
TGTGGTCAGCGTCCTCACCGTCCTGCACCAGGACTGGCTGAACGGCAAGGAGTACAAGTGCAAGGTCTCCAACAAAGG
CCTCCCGTCCTCCATCGAGAAAACCATCTCCAAAGCCAAAGGTGGGACCCACGGGGTGCGAGGGCCACATGGACAGAG
GTCAGCTCGGCCCACCCTCTGCCCTGGGAGTGACCGCTGTGCCAACCTCTGTCCCTACAGGGCAGCCCCGAGAGCCAC
AGGTGTACACCCTGCCCCCATCCCAGGAGGAGATGACCAAGAACCAGGTCAGCCTGACCTGCCTGGTCAAAGGCTTCT
ACCCCAGCGACATCGCCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAGCAGGGGAACATCTTCTCAT
GCTCCGTGATGCATGAGGCTCTGCACAACCACTACACGCAGAAGAGCCTCTCCCTGTCCCCGGGTGCAGGGGGCGGGG
GCAGCGGGGGCGGAGGATCCGGCGGGGGCTCGGGTATGAGCTACAACTTGCTTGGATTCCTACAAAGAAGCAGCAATT

FIG. 15-1

TTCAGAGTCAGAAGCTCCTGTGGCAATTGAATGGGAGGCTTGAATATTGCCTCAAGGACAGGATGAACTTTGACATCC
CTGAGGAGATTAAGCAGCTGCAGCAGTTCCAGAAGGAGGACGCCGCATTGACCATCTATGAGATGCTCCAGAACATCT
TTGCTATTTTCAGACAAGATTCATCTAGCACTGGCTGGAATGAGACTATTGTTGAGAACCTCCTGGCTAATGTCTATC
ATCAGATAAACCATCTGAAGACAGTCCTGGAAGAAAAACTGGAGAAAGAAGATTTCACCAGGGGAAAACTCATGAGCA
GTCTGCACCTGAAAAGATATTATGGGAGGATTCTGCATTACCTGAAGGCCAAGGAGTACAGTCACTGTGCCTGGACCA
TAGTCAGAGTGGAAATCCTAAGGAACTTTTACTTCATTAACAGACTTACAGGTTACCTCCGAAACTGACTCGAGGGAT
CCAGACATGATAAGATACATTGATGAGTTTGGACAAACCACAACTAGAATGCAGTGAAAAAAATGCTTTATTTGTGAA
ATTTGTGATGCTATTGCTTTATTTGTAACCATTAGAAGCTGCAATAAACAAGTTAACAACAACAATTGCATTCATTTT
ATGTTTCAGGTTCAGGGGGAGGTGTGGGAGGTTTTTTAAAGCAAGTAAAACCTCTACAAATGTGGTATGGCTGATTAT
GATCCTGCCTCGCGCGTTTCGGTGATGACGGTGAAAACCTCTGACACATGCAGCTCCCGGAGACGGTCACAGCTTGTC
TGTAAGCGGATGCCGGGAGCAGACAAGCCCGTCAGGGCGCGTCAGCGGGTGTTGGCGGGTGTCGGGGCGCAGCCATGA
CCCAGTCACGTAGCGATAGCGGAGTGTATACTGGCTTAACTATGCGGCATCAGAGCAGATTGTACTGAGAGTGCACCA
TATGCGGTGTGAAATACCGCACAGATGCGTAAGGAGAAAATACCGCATCAGGCGCTCTTCCGCTTCCTCGCTCACTGA
CTCGCTGCGCTCGGTCGTTCGGCTGCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCAATGCTCACGCTGTAGGTATCTCAGTTCGGTGTAGGT
CGTTCGCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAGAAGGACAGTATTTGGTATCTGCGCTCT
GCTGAAGCCAGTTACCTTCGGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTTTTCTACGGGGTCTGA
CGCTCAGTGGAACGAAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCCCCGTCGTGTAGATAACTACGAT
ACGGGAGGGCTTACCATCTGGCCCCAGTGCTGCAATGATACCGCGAGACCCACGCTCACCGGCTCCAGATTTATCAGC
AATAAACCAGCCAGCCGGAAGGGCCGAGCGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACGTTGTTGCCATTGCTGCAGGCATCGTGGT
GTCACGCTCGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTGGTGAGTACTCAACCAA
GTCATTCTGAGAATAGTGTATGCGGCGACCGAGTTGCTCTTGCCCGGCGTCAACACGGGATAATACCGCGCCACATAG
CAGAACTTTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGTGAGCAAA

FIG. 15-2

AACAGGAAGGCAAAATGCCGCAAAAAAGGGAATAAGGGCGACACGGAAATGTTGAATACTCATACTCTTCCTTTTTCA
ATATTATTGAAGCATTTATCAGGGTTATTGTCTCATGAGCGGATACATATTTGAATGTATTTAGAAAAATAAACAAAT
AGGGGTTCCGCGCACATTTCCCCGAAAAGTGCCACCTGACGTCTAAGAAACCATTATTATCATGACATTAACCTATAA
AAATAGGCGTATCACGAGGCCCTTTCGTCTTCAAGAATTCCGATCCAGACATGATAAGATACATTGATGAGTTTGGAC
AAACCACAACTAGAATGCAGTGAAAAAAATGCTTTATTTGTGAAATTTGTGATGCTATTGCTTTATTTGTAACCATTA
GAAGCTGCAATAAACAAGTTAACAACAACAATTGCATTCATTTTATGTTTCAGGTTCAGGGGGAGGTGTGGGAGGTTT
TTTAAAGCAAGTAAAACCTCTACAAATGTGGTATGGCTGATTATGATCTAAAGCCAGCAAAAGTCCCATGGTCTTATA
AAAATGCATAGCTTTCGGAGGGGAGCAGAGAACTTGAAAGCATCTTCCTGTTAGTCTTTCTTCTCGTAGACCTTAAAT
TCATACTTGATTCCTTTTTCCTCCTGGACCTCAGAGAGGACGCCTGGGTATTCTGGGAGAAGTTTATATTTCCCCAAA
TCAATTTCTGGGAAAAACGTGTCACTTTCAAATTCCTGCATGATCCTTGTCACAAAGAGTCTGAGGTGGCCTGGTTGA
TTCATGGCTTCCTGGTAAACAGAACTGCCTCCGACTATCCAAACCATGTCTACTTTACTTGCCAATTCCGGTTGTTCA
ATAAGTCTTAAGGCATCATCCAAACTTTTGGCAAGAAAATGAGCTCCTCGTGGTGGTTCTTTGAGTTCTCTACTGAGA
ACTATATTAATTCTGTCCTTTAAAGGTCGATTCTTCTCAGGAATGGAGAACCAGGTTTTCCTACCCATAATCACCAGA
TTCTGTTTACCTTCCACTGAAGAGGTTGTGGTCATTCTTTGGAAGTACTTGAACTCGTTCCTGAGCGGAGGCCAGGGT
CGGTCTCCGTTCTTGCCAATCCCCATATTTTGGGACACGGCGACGATGCAGTTCAATGGTCGAACCATGAGGGCACCA
AGCTAGCTTTTTGCAAAAGCCTAGGCCTCCAAAAAAGCCTCCTCACTACTTCTGGAATAGCTCAGAGGCCGAGGCGGC
CTCGGCCTCTGCATAAATAAAAAAAATTAGTCAGCCATGGGGCGGAGAATGGGCGGAACTGGGCGGAGTTAGGGGCGG
GATGGGCGGAGTTAGGGGCGGGACTATGGTTGCTGACTAATTGAGATGCATGCTTTGCATACTTCTGCCTGCTGGGGA
GCCTGGGGACTTTCCACACCTGGTTGCTGACTAATTGAGATGCATGCTTTGCATACTTCTGCCTGCTGGGGAGCCTGG
GGACTTTCCACACCCTAACTGACACACATTCCACA (SEQ ID NO:14)

FIG. 15-3

Human Fcg4h-linker-IFN-β(C17S) (γ4 isotype with modified γ1 hinge) nucleic acid sequence, starting from hinge:

GAGCCCAAATCTTCTGACAAAACTCACACATGCCCACCGTGCCCAGGTAAGCCAGCCCAGGCCTCGCCCTCCAGCTCA
AGGCGGGACAGGTGCCCTAGAGTAGCCTGCATCCAGGGACAGGCCCCAGCCGGGTGCTGACGCATCCACCTCCATCTC
TTCCTCAGCACCTGAGTTCCTGGGGGGACCATCAGTCTTCCTGTTCCCCCCAAAACCCAAGGACACTCTCATGATCTC
CCGGACCCCTGAGGTCACGTGCGTGGTGGTGGACGTGAGCCAGGAAGACCCCGAGGTCCAGTTCAACTGGTACGTGGA
TGGCGTGGAGGTGCATAATGCCAAGACAAAGCCGCGGGAGGAGCAGTTCAACAGCACGTACCGTGTGGTCAGCGTCCT
CACCGTCCTGCACCAGGACTGGCTGAACGGCAAGGAGTACAAGTGCAAGGTCTCCAACAAAGGCCTCCCGTCCTCCAT
CGAGAAAACCATCTCCAAAGCCAAAGGTGGGACCCACGGGGTGCGAGGGCCACATGGACAGAGGTCAGCTCGGCCCAC
CCTCTGCCCTGGGAGTGACCGCTGTGCCAACCTCTGTCCCTACAGGGCAGCCCCGAGAGCCACAGGTGTACACCCTGC
CCCCATCCCAGGAGGAGATGACCAAGAACCAGGTCAGCCTGACCTGCCTGGTCAAAGGCTTCTACCCCAGCGACATCG
CCGTGGAGTGGGAGAGCAATGGGCAGCCGGAGAACAACTACAAGACCACGCCTCCCGTGCTGGACTCCGACGGCTCCT
TCTTCCTCTACAGCAAGCTCACCGTGGACAAGAGCAGGTGGCAGCAGGGGAACATCTTCTCATGCTCCGTGATGCATG
AGGCTCTGCACAACCACTACACGCAGAAGAGCCTCTCCCTGTCCCCGGGTGCAGGGGGCGGGGGCAGCGGGGGCGGAG
GATCCGGCGGGGGCTCGGGTATGAGCTACAACTTGCTTGGATTCCTACAAAGAAGCAGCAATTTTCAGAGTCAGAAGC
TCCTGTGGCAATTGAATGGGAGGCTTGAATATTGCCTCAAGGACAGGATGAACTTTGACATCCCTGAGGAGATTAAGC
AGCTGCAGCAGTTCCAGAAGGAGGACGCCGCATTGACCATCTATGAGATGCTCCAGAACATCTTTGCTATTTTCAGAC
AAGATTCATCTAGCACTGGCTGGAATGAGACTATTGTTGAGAACCTCCTGGCTAATGTCTATCATCAGATAAACCATC
TGAAGACAGTCCTGGAAGAAAAACTGGAGAAAGAAGATTTCACCAGGGGAAAACTCATGAGCAGTCTGCACCTGAAAA
GATATTATGGGAGGATTCTGCATTACCTGAAGGCCAAGGAGTACAGTCACTGTGCCTGGACCATAGTCAGAGTGGAAA
TCCTAAGGAACTTTTACTTCATTAACAGACTTACAGGTTACCTCCGAAACTGA (SEQ ID NO:15)

FIG. 16

Linearized Nucleic Acid Sequence of pdCs Vector Containing huFcγ4h-linker-IFN-β (C17S L57A H131A H140A) (γ4 isotype with modified γ1 hinge):

GTCGACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATGACGT
ATGTTCCCATAGTAACGCCAATAGGGACTTTCCATTGACGTCAATGGGTGGAGTATTTACGGTAAACTGCCCACTTGG
CAGTACATCAAGTGTATCATATGCCAAGTACGCCCCCTATTGACGTCAATGACGGTAAATGGCCCGCCTGGCATTATG
CCCAGTACATGACCTTATGGGACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAAGTCTCCACCCCATTGACGTCA
ATGGGAGTTTGTTTTGGCACCAAAATCAACGGGACTTTCCAAAATGTCGTAACAACTCCGCCCCATTGACGCAAATGG
GCGGTAGGCGTGTACGGTGGGAGGTCTATATAAGCAGAGCTCTCTGGCTAACTACAGAACCCACTGCTTACTGGCTTA
TCGAAATTAATACGACTCACTATAGGGAGACCCTCTAGACCACCATGGAGTTGCCTGTTAGGCTGTTGGTGCTGATGT
TCTGGATTCCTGGTGAGGAGAGAGGGAAGTGAGGGAGGAGAATGGACAGGGAGCAGGAGCACTGAATCCCATTGCTCA
TTCCATGTATCTGGCATGGGTGAGAAGATGGGTCTTATCCTCCAGCATGGGGCCTCTGGGGTGAATACTTGTTAGAGG
GAGGTTCCAGATGGGAACATGTGCTATAATGAAGATTATGAAATGGAGCCTGGGATGGTCTAAGTAATGCCTTAGAAG
TGACTAGACACTTGCAATTCACTTTTTTTGGTAAGAAGAGATTTTTAGGCTATAAAAAAATGTTATGTAAAAATAAAC
GATCACAGTTGAAATAAAAAAAAAATATAAGGATGTTCATGAATTTTGTGTATAACTATGTATTTCTCTCTCATTGTT
TCAGCTTCCTTAAGCGAGCCCAAATCTTCTGACAAAACTCACACATGCCCACCGTGCCCAGGTAAGCCAGCCCAGGCC
TCGCCCTCCAGCTCAAGGCGGGACAGGTGCCCTAGAGTAGCCTGCATCCAGGGACAGGCCCCAGCCGGGTGCTGACGC
ATCCACCTCCATCTCTTCCTCAGCACCTGAGTTCCTGGGGGGACCATCAGTCTTCCTGTTCCCCCCAAAACCCAAGGA
CACTCTCATGATCTCCCGGACCCCTGAGGTCACGTGCGTGGTGGTGGACGTGAGCCAGGAAGACCCCGAGGTCCAGTT
CAACTGGTACGTGGATGGCGTGGAGGTGCATAATGCCAAGACAAAGCCGCGGGAGGAGCAGTTCAACAGCACGTACCG
TGTGGTCAGCGTCCTCACCGTCCTGCACCAGGACTGGCTGAACGGCAAGGAGTACAAGTGCAAGGTCTCCAACAAAGG
CCTCCCGTCCTCCATCGAGAAAACCATCTCCAAAGCCAAAGGTGGGACCCACGGGGTGCGAGGGCCACATGGACAGAG
GTCAGCTCGGCCCACCCTCTGCCCTGGGAGTGACCGCTGTGCCAACCTCTGTCCCTACAGGGCAGCCCCGAGAGCCAC
AGGTGTACACCCTGCCCCCATCCCAGGAGGAGATGACCAAGAACCAGGTCAGCCTGACCTGCCTGGTCAAAGGCTTCT
ACCCCAGCGACATCGCCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAGCAGGGGAACATCTTCTCAT
GCTCCGTGATGCATGAGGCTCTGCACAACCACTACACGCAGAAGAGCCTCTCCCTGTCCCCGGGTGCAGGGGGCGGGG
GCAGCGGGGGCGGAGGATCCGGCGGGGGCTCGGGTATGAGCTACAACTTGCTTGGATTCCTACAAAGAAGCAGCAATT
TTCAGAGTCAGAAGCTCCTGTGGCAATTGAATGGGAGGCTTGAATATTGCCTCAAGGACAGGATGAACTTTGACATCC
CTGAGGAGATTAAGCAGCTGCAGCAGTTCCAGAAGGAGGACGCCGCAGCCACCATCTATGAGATGCTCCAGAACATCT
TTGCTATTTTCAGACAAGATTCATCTAGCACTGGCTGGAATGAGACTATTGTTGAGAACCTCCTGGCTAATGTCTATC
ATCAGATAAACCATCTGAAGACAGTCCTGGAAGAAAAACTGGAGAAAGAAGATTTCACCAGGGGAAAACTCATGAGCA

FIG. 17-1

GTCTGCACCTGAAAAGATATTATGGGAGGATTCTGGCCTACCTGAAGGCCAAGGAGTACAGTGCCTGTGCCTGGACCA
TAGTCAGAGTGGAAATCCTAAGGAACTTTTACTTCATTAACAGACTTACAGGTTACCTCCGAAACTGACTCGAGGGAT
CCAGACATGATAAGATACATTGATGAGTTTGGACAAACCACAACTAGAATGCAGTGAAAAAAATGCTTTATTTGTGAA
ATTTGTGATGCTATTGCTTTATTTGTAACCATTAGAAGCTGCAATAAACAAGTTAACAACAACAATTGCATTCATTTT
ATGTTTCAGGTTCAGGGGGAGGTGTGGGAGGTTTTTTAAAGCAAGTAAAACCTCTACAAATGTGGTATGGCTGATTAT
GATCCTGCCTCGCGCGTTTCGGTGATGACGGTGAAAACCTCTGACACATGCAGCTCCCGGAGACGGTCACAGCTTGTC
TGTAAGCGGATGCCGGGAGCAGACAAGCCCGTCAGGGCGCGTCAGCGGGTGTTGGCGGGTGTCGGGGCGCAGCCATGA
CCCAGTCACGTAGCGATAGCGGAGTGTATACTGGCTTAACTATGCGGCATCAGAGCAGATTGTACTGAGAGTGCACCA
TATGCGGTGTGAAATACCGCACAGATGCGTAAGGAGAAAATACCGCATCAGGCGCTCTTCCGCTTCCTCGCTCACTGA
CTCGCTGCGCTCGGTCGTTCGGCTGCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCAATGCTCACGCTGTAGGTATCTCAGTTCGGTGTAGGT
CGTTCGCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAGAAGGACAGTATTTGGTATCTGCGCTCT
GCTGAAGCCAGTTACCTTCGGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTTTTCTACGGGGTCTGA
CGCTCAGTGGAACGAAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCCCCGTCGTGTAGATAACTACGAT
ACGGGAGGGCTTACCATCTGGCCCCAGTGCTGCAATGATACCGCGAGACCCACGCTCACCGGCTCCAGATTTATCAGC
AATAAACCAGCCAGCCGGAAGGGCCGAGCGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACGTTGTTGCCATTGCTGCAGGCATCGTGGT
GTCACGCTCGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTGGTGAGTACTCAACCAA
GTCATTCTGAGAATAGTGTATGCGGCGACCGAGTTGCTCTTGCCCGGCGTCAACACGGGATAATACCGCGCCACATAG
CAGAACTTTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGTGAGCAAA
AACAGGAAGGCAAAATGCCGCAAAAAAGGGAATAAGGGCGACACGGAAATGTTGAATACTCATACTCTTCCTTTTTCA
ATATTATTGAAGCATTTATCAGGGTTATTGTCTCATGAGCGGATACATATTTGAATGTATTTAGAAAAATAAACAAAT
AGGGGTTCCGCGCACATTTCCCCGAAAAGTGCCACCTGACGTCTAAGAAACCATTATTATCATGACATTAACCTATAA
AAATAGGCGTATCACGAGGCCCTTTCGTCTTCAAGAATTCCGATCCAGACATGATAAGATACATTGATGAGTTTGGAC

FIG. 17-2

AAACCACAACTAGAATGCAGTGAAAAAAATGCTTTATTTGTGAAATTTGTGATGCTATTGCTTTATTTGTAACCATTA
GAAGCTGCAATAAACAAGTTAACAACAACAATTGCATTCATTTTATGTTTCAGGTTCAGGGGGAGGTGTGGGAGGTTT
TTTAAAGCAAGTAAAACCTCTACAAATGTGGTATGGCTGATTATGATCTAAAGCCAGCAAAAGTCCCATGGTCTTATA
AAAATGCATAGCTTTCGGAGGGGAGCAGAGAACTTGAAAGCATCTTCCTGTTAGTCTTTCTTCTCGTAGACCTTAAAT
TCATACTTGATTCCTTTTTCCTCCTGGACCTCAGAGAGGACGCCTGGGTATTCTGGGAGAAGTTTATATTTCCCCAAA
TCAATTTCTGGGAAAAACGTGTCACTTTCAAATTCCTGCATGATCCTTGTCACAAAGAGTCTGAGGTGGCCTGGTTGA
TTCATGGCTTCCTGGTAAACAGAACTGCCTCCGACTATCCAAACCATGTCTACTTTACTTGCCAATTCCGGTTGTTCA
ATAAGTCTTAAGGCATCATCCAAACTTTTGGCAAGAAAATGAGCTCCTCGTGGTGGTTCTTTGAGTTCTCTACTGAGA
ACTATATTAATTCTGTCCTTTAAAGGTCGATTCTTCTCAGGAATGGAGAACCAGGTTTTCCTACCCATAATCACCAGA
TTCTGTTTACCTTCCACTGAAGAGGTTGTGGTCATTCTTTGGAAGTACTTGAACTCGTTCCTGAGCGGAGGCCAGGGT
CGGTCTCCGTTCTTGCCAATCCCCATATTTTGGGACACGGCGACGATGCAGTTCAATGGTCGAACCATGAGGGCACCA
AGCTAGCTTTTTGCAAAAGCCTAGGCCTCCAAAAAAGCCTCCTCACTACTTCTGGAATAGCTCAGAGGCCGAGGCGGC
CTCGGCCTCTGCATAAATAAAAAAAATTAGTCAGCCATGGGGCGGAGAATGGGCGGAACTGGGCGGAGTTAGGGGCGG
GATGGGCGGAGTTAGGGGCGGGACTATGGTTGCTGACTAATTGAGATGCATGCTTTGCATACTTCTGCCTGCTGGGGA
GCCTGGGGACTTTCCACACCTGGTTGCTGACTAATTGAGATGCATGCTTTGCATACTTCTGCCTGCTGGGGAGCCTGG
GGACTTTCCACACCCTAACTGACACACATTCCACA (SEQ ID NO:16)

FIG. 17-3

Nucleic Acid Sequence of huFcγ4h-linker-IFN-β (C17S L57A H131A H140A) (γ4 isotype with modified γ1 hinge), starting from the hinge:

GAGCCCAAATCTTCTGACAAAACTCACACATGCCCACCGTGCCCAGGTAAGCCAGCCCAGGCCTCGCCCTCCAGCTCA
AGGCGGGACAGGTGCCCTAGAGTAGCCTGCATCCAGGGACAGGCCCCAGCCGGGTGCTGACGCATCCACCTCCATCTC
TTCCTCAGCACCTGAGTTCCTGGGGGGACCATCAGTCTTCCTGTTCCCCCCAAAACCCAAGGACACTCTCATGATCTC
CCGGACCCCTGAGGTCACGTGCGTGGTGGTGGACGTGAGCCAGGAAGACCCCGAGGTCCAGTTCAACTGGTACGTGGA
TGGCGTGGAGGTGCATAATGCCAAGACAAAGCCGCGGGAGGAGCAGTTCAACAGCACGTACCGTGTGGTCAGCGTCCT
CACCGTCCTGCACCAGGACTGGCTGAACGGCAAGGAGTACAAGTGCAAGGTCTCCAACAAAGGCCTCCCGTCCTCCAT
CGAGAAAACCATCTCCAAAGCCAAAGGTGGGACCCACGGGGTGCGAGGGCCACATGGACAGAGGTCAGCTCGGCCCAC
CCTCTGCCCTGGGAGTGACCGCTGTGCCAACCTCTGTCCCTACAGGGCAGCCCCGAGAGCCACAGGTGTACACCCTGC
CCCCATCCCAGGAGGAGATGACCAAGAACCAGGTCAGCCTGACCTGCCTGGTCAAAGGCTTCTACCCCAGCGACATCG
CCGTGGAGTGGGAGAGCAATGGGCAGCCGGAGAACAACTACAAGACCACGCCTCCCGTGCTGGACTCCGACGGCTCCT
TCTTCCTCTACAGCAAGCTCACCGTGGACAAGAGCAGGTGGCAGCAGGGGAACATCTTCTCATGCTCCGTGATGCATG
AGGCTCTGCACAACCACTACACGCAGAAGAGCCTCTCCCTGTCCCCGGGTGCAGGGGGCGGGGGCAGCGGGGGCGGAG
GATCCGGCGGGGGCTCGGGTATGAGCTACAACTTGCTTGGATTCCTACAAAGAAGCAGCAATTTTCAGAGTCAGAAGC
TCCTGTGGCAATTGAATGGGAGGCTTGAATATTGCCTCAAGGACAGGATGAACTTTGACATCCCTGAGGAGATTAAGC
AGCTGCAGCAGTTCCAGAAGGAGGACGCCGCAGCCACCATCTATGAGATGCTCCAGAACATCTTTGCTATTTTCAGAC
AAGATTCATCTAGCACTGGCTGGAATGAGACTATTGTTGAGAACCTCCTGGCTAATGTCTATCATCAGATAAACCATC
TGAAGACAGTCCTGGAAGAAAAACTGGAGAAAGAAGATTTCACCAGGGGAAAACTCATGAGCAGTCTGCACCTGAAAA
GATATTATGGGAGGATTCTGGCCTACCTGAAGGCCAAGGAGTACAGTGCCTGTGCCTGGACCATAGTCAGAGTGGAAA
TCCTAAGGAACTTTTACTTCATTAACAGACTTACAGGTTACCTCCGAAACTGA (SEQ ID NO:17)

FIG. 18

Linearized Nucleic Acid Sequence of pdCs Vector Containing huFcγ4h-linker-IFN-β(C17S F50H H131A H140A) (γ4 isotype with modified γ1 hinge):

GTCGACATTGATTATTGACTAGTTATTAATAGTAATCAATTACGGGGTCATTAGTTCATAGCCCATATATGGAGTTCC
GCGTTACATAACTTACGGTAAATGGCCCGCCTGGCTGACCGCCCAACGACCCCCGCCCATTGACGTCAATAATGACGT
ATGTTCCCATAGTAACGCCAATAGGGACTTTCCATTGACGTCAATGGGTGGAGTATTTACGGTAAACTGCCCACTTGG
CAGTACATCAAGTGTATCATATGCCAAGTACGCCCCCTATTGACGTCAATGACGGTAAATGGCCCGCCTGGCATTATG
CCCAGTACATGACCTTATGGGACTTTCCTACTTGGCAGTACATCTACGTATTAGTCATCGCTATTACCATGGTGATGC
GGTTTTGGCAGTACATCAATGGGCGTGGATAGCGGTTTGACTCACGGGGATTTCCAAGTCTCCACCCCATTGACGTCA
ATGGGAGTTTGTTTTGGCACCAAAATCAACGGGACTTTCCAAAATGTCGTAACAACTCCGCCCCATTGACGCAAATGG
GCGGTAGGCGTGTACGGTGGGAGGTCTATATAAGCAGAGCTCTCTGGCTAACTACAGAACCCACTGCTTACTGGCTTA
TCGAAATTAATACGACTCACTATAGGGAGACCCTCTAGACCACCATGGAGTTGCCTGTTAGGCTGTTGGTGCTGATGT
TCTGGATTCCTGGTGAGGAGAGAGGGAAGTGAGGGAGGAGAATGGACAGGGAGCAGGAGCACTGAATCCCATTGCTCA
TTCCATGTATCTGGCATGGGTGAGAAGATGGGTCTTATCCTCCAGCATGGGGCCTCTGGGGTGAATACTTGTTAGAGG
GAGGTTCCAGATGGGAACATGTGCTATAATGAAGATTATGAAATGGAGCCTGGGATGGTCTAAGTAATGCCTTAGAAG
TGACTAGACACTTGCAATTCACTTTTTTTGGTAAGAAGAGATTTTTAGGCTATAAAAAAATGTTATGTAAAAATAAAC
GATCACAGTTGAAATAAAAAAAAAATATAAGGATGTTCATGAATTTTGTGTATAACTATGTATTTCTCTCTCATTGTT
TCAGCTTCCTTAAGCGAGCCCAAATCTTCTGACAAAACTCACACATGCCCACCGTGCCCAGGTAAGCCAGCCCAGGCC
TCGCCCTCCAGCTCAAGGCGGGACAGGTGCCCTAGAGTAGCCTGCATCCAGGGACAGGCCCCAGCCGGGTGCTGACGC
ATCCACCTCCATCTCTTCCTCAGCACCTGAGTTCCTGGGGGGACCATCAGTCTTCCTGTTCCCCCCAAAACCCAAGGA
CACTCTCATGATCTCCCGGACCCCTGAGGTCACGTGCGTGGTGGTGGACGTGAGCCAGGAAGACCCCGAGGTCCAGTT
CAACTGGTACGTGGATGGCGTGGAGGTGCATAATGCCAAGACAAAGCCGCGGGAGGAGCAGTTCAACAGCACGTACCG
TGTGGTCAGCGTCCTCACCGTCCTGCACCAGGACTGGCTGAACGGCAAGGAGTACAAGTGCAAGGTCTCCAACAAAGG
CCTCCCGTCCTCCATCGAGAAAACCATCTCCAAAGCCAAAGGTGGGACCCACGGGGTGCGAGGGCCACATGGACAGAG
GTCAGCTCGGCCCACCCTCTGCCCTGGGAGTGACCGCTGTGCCAACCTCTGTCCCTACAGGGCAGCCCCGAGAGCCAC
AGGTGTACACCCTGCCCCCATCCCAGGAGGAGATGACCAAGAACCAGGTCAGCCTGACCTGCCTGGTCAAAGGCTTCT
ACCCCAGCGACATCGCCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGACAAGAGCAGGTGGCAGCAGGGGAACATCTTCTCAT
GCTCCGTGATGCATGAGGCTCTGCACAACCACTACACGCAGAAGAGCCTCTCCCTGTCCCCGGGTGCAGGGGGCGGGG
GCAGCGGGGGCGGAGGATCCGGCGGGGGCTCGGGTATGAGCTACAACTTGCTTGGATTCCTACAAAGAAGCAGCAATT
TTCAGAGTCAGAAGCTCCTGTGGCAATTGAATGGGAGGCTTGAATATTGCCTCAAGGACAGGATGAACTTTGACATCC
CTGAGGAGATTAAGCAGCTGCAGCAGCATCAGAAGGAGGACGCCGCATTGACCATCTATGAGATGCTCCAGAACATCT

FIG. 19-1

TTGCTATTTTCAGACAAGATTCATCTAGCACTGGCTGGAATGAGACTATTGTTGAGAACCTCCTGGCTAATGTCTATC
ATCAGATAAACCATCTGAAGACAGTCCTGGAAGAAAAACTGGAGAAAGAAGATTTCACCAGGGGAAAACTCATGAGCA
GTCTGCACCTGAAAAGATATTATGGGAGGATTCTGGCCTACCTGAAGGCCAAGGAGTACAGTGCCTGTGCCTGGACCA
TAGTCAGAGTGGAAATCCTAAGGAACTTTTACTTCATTAACAGACTTACAGGTTACCTCCGAAACTGACTCGAGGGAT
CCAGACATGATAAGATACATTGATGAGTTTGGACAAACCACAACTAGAATGCAGTGAAAAAAATGCTTTATTTGTGAA
ATTTGTGATGCTATTGCTTTATTTGTAACCATTAGAAGCTGCAATAAACAAGTTAACAACAACAATTGCATTCATTTT
ATGTTTCAGGTTCAGGGGGAGGTGTGGGAGGTTTTTTAAAGCAAGTAAAACCTCTACAAATGTGGTATGGCTGATTAT
GATCCTGCCTCGCGCGTTTCGGTGATGACGGTGAAAACCTCTGACACATGCAGCTCCCGGAGACGGTCACAGCTTGTC
TGTAAGCGGATGCCGGGAGCAGACAAGCCCGTCAGGGCGCGTCAGCGGGTGTTGGCGGGTGTCGGGGCGCAGCCATGA
CCCAGTCACGTAGCGATAGCGGAGTGTATACTGGCTTAACTATGCGGCATCAGAGCAGATTGTACTGAGAGTGCACCA
TATGCGGTGTGAAATACCGCACAGATGCGTAAGGAGAAAATACCGCATCAGGCGCTCTTCCGCTTCCTCGCTCACTGA
CTCGCTGCGCTCGGTCGTTCGGCTGCGGCGAGCGGTATCAGCTCACTCAAAGGCGGTAATACGGTTATCCACAGAATC
AGGGGATAACGCAGGAAAGAACATGTGAGCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTTCCGACCCTGCCGCTTACCGGATA
CCTGTCCGCCTTTCTCCCTTCGGGAAGCGTGGCGCTTTCTCAATGCTCACGCTGTAGGTATCTCAGTTCGGTGTAGGT
CGTTCGCTCCAAGCTGGGCTGTGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACAGGATTAGCAGAGCGAGGTATGT
AGGCGGTGCTACAGAGTTCTTGAAGTGGTGGCCTAACTACGGCTACACTAGAAGGACAGTATTTGGTATCTGCGCTCT
GCTGAAGCCAGTTACCTTCGGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGATCTTTTCTACGGGGTCTGA
CGCTCAGTGGAACGAAAACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTTACCAATGCTTAATCAG
TGAGGCACCTATCTCAGCGATCTGTCTATTTCGTTCATCCATAGTTGCCTGACTCCCCGTCGTGTAGATAACTACGAT
ACGGGAGGGCTTACCATCTGGCCCCAGTGCTGCAATGATACCGCGAGACCCACGCTCACCGGCTCCAGATTTATCAGC
AATAAACCAGCCAGCCGGAAGGGCCGAGCGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACGTTGTTGCCATTGCTGCAGGCATCGTGGT
GTCACGCTCGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTGGTGAGTACTCAACCAA
GTCATTCTGAGAATAGTGTATGCGGCGACCGAGTTGCTCTTGCCCGGCGTCAACACGGGATAATACCGCGCCACATAG
CAGAACTTTAAAAGTGCTCATCATTGGAAAACGTTCTTCGGGGCGAAAACTCTCAAGGATCTTACCGCTGTTGAGATC

FIG. 19-2

CAGTTCGATGTAACCCACTCGTGCACCCAACTGATCTTCAGCATCTTTTACTTTCACCAGCGTTTCTGGGTGAGCAAA
AACAGGAAGGCAAAATGCCGCAAAAAAGGGAATAAGGGCGACACGGAAATGTTGAATACTCATACTCTTCCTTTTTCA
ATATTATTGAAGCATTTATCAGGGTTATTGTCTCATGAGCGGATACATATTTGAATGTATTTAGAAAAATAAACAAAT
AGGGGTTCCGCGCACATTTCCCCGAAAAGTGCCACCTGACGTCTAAGAAACCATTATTATCATGACATTAACCTATAA
AAATAGGCGTATCACGAGGCCCTTTCGTCTTCAAGAATTCCGATCCAGACATGATAAGATACATTGATGAGTTTGGAC
AAACCACAACTAGAATGCAGTGAAAAAAATGCTTTATTTGTGAAATTTGTGATGCTATTGCTTTATTTGTAACCATTA
GAAGCTGCAATAAACAAGTTAACAACAACAATTGCATTCATTTTATGTTTCAGGTTCAGGGGGAGGTGTGGGAGGTTT
TTTAAAGCAAGTAAAACCTCTACAAATGTGGTATGGCTGATTATGATCTAAAGCCAGCAAAAGTCCCATGGTCTTATA
AAAATGCATAGCTTTCGGAGGGGAGCAGAGAACTTGAAAGCATCTTCCTGTTAGTCTTTCTTCTCGTAGACCTTAAAT
TCATACTTGATTCCTTTTTCCTCCTGGACCTCAGAGAGGACGCCTGGGTATTCTGGGAGAAGTTTATATTTCCCCAAA
TCAATTTCTGGGAAAAACGTGTCACTTTCAAATTCCTGCATGATCCTTGTCACAAAGAGTCTGAGGTGGCCTGGTTGA
TTCATGGCTTCCTGGTAAACAGAACTGCCTCCGACTATCCAAACCATGTCTACTTTACTTGCCAATTCCGGTTGTTCA
ATAAGTCTTAAGGCATCATCCAAACTTTTGGCAAGAAAATGAGCTCCTCGTGGTGGTTCTTTGAGTTCTCTACTGAGA
ACTATATTAATTCTGTCCTTTAAAGGTCGATTCTTCTCAGGAATGGAGAACCAGGTTTTCCTACCCATAATCACCAGA
TTCTGTTTACCTTCCACTGAAGAGGTTGTGGTCATTCTTTGGAAGTACTTGAACTCGTTCCTGAGCGGAGGCCAGGGT
CGGTCTCCGTTCTTGCCAATCCCCATATTTTGGGACACGGCGACGATGCAGTTCAATGGTCGAACCATGAGGGCACCA
AGCTAGCTTTTTGCAAAAGCCTAGGCCTCCAAAAAAGCCTCCTCACTACTTCTGGAATAGCTCAGAGGCCGAGGCGGC
CTCGGCCTCTGCATAAATAAAAAAAATTAGTCAGCCATGGGGCGGAGAATGGGCGGAACTGGGCGGAGTTAGGGGCGG
GATGGGCGGAGTTAGGGGCGGGACTATGGTTGCTGACTAATTGAGATGCATGCTTTGCATACTTCTGCCTGCTGGGGA
GCCTGGGGACTTTCCACACCTGGTTGCTGACTAATTGAGATGCATGCTTTGCATACTTCTGCCTGCTGGGGAGCCTGG
GGACTTTCCACACCCTAACTGACACACATTCCACA (SEQ ID NO:18)

FIG. 19-3

Human Fcγ4h-linker-IFN-β(C17S F50H H131A H140A) (γ4 with modified γ1 hinge) nucleic acid sequence, beginning at the hinge:

GAGCCCAAATCTTCTGACAAAACTCACACATGCCCACCGTGCCCAGGTAAGCCAGCCCAGGCCTCGCCCTCCAGCTCA
AGGCGGGACAGGTGCCCTAGAGTAGCCTGCATCCAGGGACAGGCCCCAGCCGGGTGCTGACGCATCCACCTCCATCTC
TTCCTCAGCACCTGAGTTCCTGGGGGGACCATCAGTCTTCCTGTTCCCCCCAAAACCCAAGGACACTCTCATGATCTC
CCGGACCCCTGAGGTCACGTGCGTGGTGGTGGACGTGAGCCAGGAAGACCCCGAGGTCCAGTTCAACTGGTACGTGGA
TGGCGTGGAGGTGCATAATGCCAAGACAAAGCCGCGGGAGGAGCAGTTCAACAGCACGTACCGTGTGGTCAGCGTCCT
CACCGTCCTGCACCAGGACTGGCTGAACGGCAAGGAGTACAAGTGCAAGGTCTCCAACAAAGGCCTCCCGTCCTCCAT
CGAGAAAACCATCTCCAAAGCCAAAGGTGGGACCCACGGGGTGCGAGGGCCACATGGACAGAGGTCAGCTCGGCCCAC
CCTCTGCCCTGGGAGTGACCGCTGTGCCAACCTCTGTCCCTACAGGGCAGCCCCGAGAGCCACAGGTGTACACCCTGC
CCCCATCCCAGGAGGAGATGACCAAGAACCAGGTCAGCCTGACCTGCCTGGTCAAAGGCTTCTACCCCAGCGACATCG
CCGTGGAGTGGGAGAGCAATGGGCAGCCGGAGAACAACTACAAGACCACGCCTCCCGTGCTGGACTCCGACGGCTCCT
TCTTCCTCTACAGCAAGCTCACCGTGGACAAGAGCAGGTGGCAGCAGGGGAACATCTTCTCATGCTCCGTGATGCATG
AGGCTCTGCACAACCACTACACGCAGAAGAGCCTCTCCCTGTCCCCGGGTGCAGGGGGCGGGGGCAGCGGGGGCGGAG
GATCCGGCGGGGGCTCGGGTATGAGCTACAACTTGCTTGGATTCCTACAAAGAAGCAGCAATTTTCAGAGTCAGAAGC
TCCTGTGGCAATTGAATGGGAGGCTTGAATATTGCCTCAAGGACAGGATGAACTTTGACATCCCTGAGGAGATTAAGC
AGCTGCAGCAGCATCAGAAGGAGGACGCCGCATTGACCATCTATGAGATGCTCCAGAACATCTTTGCTATTTTCAGAC
AAGATTCATCTAGCACTGGCTGGAATGAGACTATTGTTGAGAACCTCCTGGCTAATGTCTATCATCAGATAAACCATC
TGAAGACAGTCCTGGAAGAAAAACTGGAGAAAGAAGATTTCACCAGGGGAAAACTCATGAGCAGTCTGCACCTGAAAA
GATATTATGGGAGGATTCTGGCCTACCTGAAGGCCAAGGAGTACAGTGCCTGTGCCTGGACCATAGTCAGAGTGGAAA
TCCTAAGGAACTTTTACTTCATTAACAGACTTACAGGTTACCTCCGAAACTGA (SEQ ID NO:19)

FIG. 20

SEQUENCE LISTING

<160> NUMBER OF SEQ ID NOS: 79

<210> SEQ ID NO 1
<211> LENGTH: 15
<212> TYPE: PRT
<213> ORGANISM: Artificial Sequence
<220> FEATURE:
<223> OTHER INFORMATION: Peptide Linker

<400> SEQUENCE: 1

```
Gly Gly Gly Gly Ser Gly Gly Gly Gly Ser Gly Gly Gly Ser Gly
1               5                   10                  15
```

<210> SEQ ID NO 2
<211> LENGTH: 166
<212> TYPE: PRT
<213> ORGANISM: Homo sapiens

<400> SEQUENCE: 2

```
Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

<210> SEQ ID NO 3
<211> LENGTH: 166
<212> TYPE: PRT
<213> ORGANISM: Artificial Sequence
<220> FEATURE:
<223> OTHER INFORMATION: Mature human IFN-beta with amino acid
      substitution C17S

<400> SEQUENCE: 3

```
Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60
```

Asn Ile Phe Ala Ile Phe Arg Gln Asp Ser Ser Ser Thr Gly Trp Asn
65 70 75 80

Glu Thr Ile Val Glu Asn Leu Leu Ala Asn Val Tyr His Gln Ile Asn
85 90 95

His Leu Lys Thr Val Leu Glu Glu Lys Leu Glu Lys Glu Asp Phe Thr
100 105 110

Arg Gly Lys Leu Met Ser Ser Leu His Leu Lys Arg Tyr Tyr Gly Arg
115 120 125

Ile Leu His Tyr Leu Lys Ala Lys Glu Tyr Ser His Cys Ala Trp Thr
130 135 140

Ile Val Arg Val Glu Ile Leu Arg Asn Phe Tyr Phe Ile Asn Arg Leu
145 150 155 160

Thr Gly Tyr Leu Arg Asn
165

<210> SEQ ID NO 4
<211> LENGTH: 397
<212> TYPE: PRT
<213> ORGANISM: Artificial Sequence
<220> FEATURE:
<223> OTHER INFORMATION: An amino acid sequence for human Fc-IFN-beta (C17S) with Fc region of IgG4 isotype and a modified IgG1 hinge

<400> SEQUENCE: 4

Glu Pro Lys Ser Ser Asp Lys Thr His Thr Cys Pro Pro Cys Pro Ala
1 5 10 15

Pro Glu Phe Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser Gln Glu Asp Pro Glu Val Gln Phe Asn Trp Tyr Val
50 55 60

Asp Gly Val Glu Val His Asn Ala Lys Thr Lys Pro Arg Glu Glu Gln
65 70 75 80

Phe Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Gly
100 105 110

Leu Pro Ser Ser Ile Glu Lys Thr Ile Ser Lys Ala Lys Gly Gln Pro
115 120 125

Arg Glu Pro Gln Val Tyr Thr Leu Pro Pro Ser Gln Glu Glu Met Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Ile Phe
195 200 205

Ser Cys Ser Val Met His Glu Ala Leu His Asn His Tyr Thr Gln Lys
210 215 220

Ser Leu Ser Leu Ser Pro Gly Met Ser Tyr Asn Leu Leu Gly Phe Leu
225 230 235 240

Gln Arg Ser Ser Asn Phe Gln Ser Gln Lys Leu Leu Trp Gln Leu Asn
245 250 255

```
Gly Arg Leu Glu Tyr Cys Leu Lys Asp Arg Met Asn Phe Asp Ile Pro
            260                 265                 270

Glu Glu Ile Lys Gln Leu Gln Gln Phe Gln Lys Glu Asp Ala Ala Leu
        275                 280                 285

Thr Ile Tyr Glu Met Leu Gln Asn Ile Phe Ala Ile Phe Arg Gln Asp
    290                 295                 300

Ser Ser Ser Thr Gly Trp Asn Glu Thr Ile Val Glu Asn Leu Leu Ala
305                 310                 315                 320

Asn Val Tyr His Gln Ile Asn His Leu Lys Thr Val Leu Glu Glu Lys
                325                 330                 335

Leu Glu Lys Glu Asp Phe Thr Arg Gly Lys Leu Met Ser Ser Leu His
            340                 345                 350

Leu Lys Arg Tyr Tyr Gly Arg Ile Leu His Tyr Leu Lys Ala Lys Glu
        355                 360                 365

Tyr Ser His Cys Ala Trp Thr Ile Val Arg Val Glu Ile Leu Arg Asn
    370                 375                 380

Phe Tyr Phe Ile Asn Arg Leu Thr Gly Tyr Leu Arg Asn
385                 390                 395


<210> SEQ ID NO 5
<211> LENGTH: 288
<212> TYPE: PRT
<213> ORGANISM: Artificial Sequence
<220> FEATURE:
<223> OTHER INFORMATION: An amino acid sequence for human Fc-(linker)-
      IFN-beta starting with the CH3 domain of the Fc IgG4 isotype.

<400> SEQUENCE: 5

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn His Tyr
                85                  90                  95

Thr Gln Lys Ser Leu Ser Leu Ser Pro Gly Ala Gly Gly Gly Gly Ser
            100                 105                 110

Gly Gly Gly Gly Ser Gly Gly Gly Ser Gly Met Ser Tyr Asn Leu Leu
        115                 120                 125

Gly Phe Leu Gln Arg Ser Ser Asn Phe Gln Cys Gln Lys Leu Leu Trp
    130                 135                 140

Gln Leu Asn Gly Arg Leu Glu Tyr Cys Leu Lys Asp Arg Met Asn Phe
145                 150                 155                 160

Asp Ile Pro Glu Glu Ile Lys Gln Leu Gln Gln Phe Gln Lys Glu Asp
                165                 170                 175

Ala Ala Leu Thr Ile Tyr Glu Met Leu Gln Asn Ile Phe Ala Ile Phe
            180                 185                 190

Arg Gln Asp Ser Ser Ser Thr Gly Trp Asn Glu Thr Ile Val Glu Asn
        195                 200                 205

Leu Leu Ala Asn Val Tyr His Gln Ile Asn His Leu Lys Thr Val Leu
    210                 215                 220
```

-continued

```
Glu Glu Lys Leu Glu Lys Glu Asp Phe Thr Arg Gly Lys Leu Met Ser
225                 230                 235                 240

Ser Leu His Leu Lys Arg Tyr Tyr Gly Arg Ile Leu His Tyr Leu Lys
                245                 250                 255

Ala Lys Glu Tyr Ser His Cys Ala Trp Thr Ile Val Arg Val Glu Ile
            260                 265                 270

Leu Arg Asn Phe Tyr Phe Ile Asn Arg Leu Thr Gly Tyr Leu Arg Asn
        275                 280                 285


<210> SEQ ID NO 6
<211> LENGTH: 288
<212> TYPE: PRT
<213> ORGANISM: Artificial Sequence
<220> FEATURE:
<223> OTHER INFORMATION: An amino acid sequence for human Fc-(linker)-
      IFN-beta (C17S) starting with the CH3 domain of the Fc IgG4
      isotype

<400> SEQUENCE: 6

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn His Tyr
                85                  90                  95

Thr Gln Lys Ser Leu Ser Leu Ser Pro Gly Ala Gly Gly Gly Gly Ser
            100                 105                 110

Gly Gly Gly Gly Ser Gly Gly Gly Ser Gly Met Ser Tyr Asn Leu Leu
        115                 120                 125

Gly Phe Leu Gln Arg Ser Ser Asn Phe Gln Ser Gln Lys Leu Leu Trp
    130                 135                 140

Gln Leu Asn Gly Arg Leu Glu Tyr Cys Leu Lys Asp Arg Met Asn Phe
145                 150                 155                 160

Asp Ile Pro Glu Glu Ile Lys Gln Leu Gln Gln Phe Gln Lys Glu Asp
                165                 170                 175

Ala Ala Leu Thr Ile Tyr Glu Met Leu Gln Asn Ile Phe Ala Ile Phe
            180                 185                 190

Arg Gln Asp Ser Ser Ser Thr Gly Trp Asn Glu Thr Ile Val Glu Asn
        195                 200                 205

Leu Leu Ala Asn Val Tyr His Gln Ile Asn His Leu Lys Thr Val Leu
    210                 215                 220

Glu Glu Lys Leu Glu Lys Glu Asp Phe Thr Arg Gly Lys Leu Met Ser
225                 230                 235                 240

Ser Leu His Leu Lys Arg Tyr Tyr Gly Arg Ile Leu His Tyr Leu Lys
                245                 250                 255

Ala Lys Glu Tyr Ser His Cys Ala Trp Thr Ile Val Arg Val Glu Ile
            260                 265                 270

Leu Arg Asn Phe Tyr Phe Ile Asn Arg Leu Thr Gly Tyr Leu Arg Asn
        275                 280                 285
```

-continued

<210> SEQ ID NO 7
<211> LENGTH: 288
<212> TYPE: PRT
<213> ORGANISM: Artificial Sequence
<220> FEATURE:
<223> OTHER INFORMATION: An amino acid sequence for human Fc-(linker)-
IFN-beta (C17S L57A H131A H140T) starting with the CH3 domain of
the Fc IgG4 isotype

<400> SEQUENCE: 7

```
Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn His Tyr
                85                  90                  95

Thr Gln Lys Ser Leu Ser Leu Ser Pro Gly Ala Gly Gly Gly Gly Ser
            100                 105                 110

Gly Gly Gly Gly Ser Gly Gly Gly Ser Gly Met Ser Tyr Asn Leu Leu
        115                 120                 125

Gly Phe Leu Gln Arg Ser Ser Asn Phe Gln Ser Gln Lys Leu Leu Trp
    130                 135                 140

Gln Leu Asn Gly Arg Leu Glu Tyr Cys Leu Lys Asp Arg Met Asn Phe
145                 150                 155                 160

Asp Ile Pro Glu Glu Ile Lys Gln Leu Gln Gln Phe Gln Lys Glu Asp
                165                 170                 175

Ala Ala Ala Thr Ile Tyr Glu Met Leu Gln Asn Ile Phe Ala Ile Phe
            180                 185                 190

Arg Gln Asp Ser Ser Ser Thr Gly Trp Asn Glu Thr Ile Val Glu Asn
        195                 200                 205

Leu Leu Ala Asn Val Tyr His Gln Ile Asn His Leu Lys Thr Val Leu
    210                 215                 220

Glu Glu Lys Leu Glu Lys Glu Asp Phe Thr Arg Gly Lys Leu Met Ser
225                 230                 235                 240

Ser Leu His Leu Lys Arg Tyr Tyr Gly Arg Ile Leu Ala Tyr Leu Lys
                245                 250                 255

Ala Lys Glu Tyr Ser Thr Cys Ala Trp Thr Ile Val Arg Val Glu Ile
            260                 265                 270

Leu Arg Asn Phe Tyr Phe Ile Asn Arg Leu Thr Gly Tyr Leu Arg Asn
        275                 280                 285
```

<210> SEQ ID NO 8
<211> LENGTH: 288
<212> TYPE: PRT
<213> ORGANISM: Artificial Sequence
<220> FEATURE:
<223> OTHER INFORMATION: An amino acid sequence for human Fc-(linker)-
IFN-beta (C17S L57A H131A H140A) starting with the CH3 domain of
the Fc IgG4 isotype

<400> SEQUENCE: 8

```
Gly Gln Pro Arg Glu Pro Gln Val Tyr Thr Leu Pro Pro Ser Gln Glu
1               5                   10                  15
```

```
Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn His Tyr
                85                  90                  95

Thr Gln Lys Ser Leu Ser Leu Ser Pro Gly Ala Gly Gly Gly Gly Ser
            100                 105                 110

Gly Gly Gly Gly Ser Gly Gly Gly Ser Gly Met Ser Tyr Asn Leu Leu
        115                 120                 125

Gly Phe Leu Gln Arg Ser Ser Asn Phe Gln Ser Gln Lys Leu Leu Trp
    130                 135                 140

Gln Leu Asn Gly Arg Leu Glu Tyr Cys Leu Lys Asp Arg Met Asn Phe
145                 150                 155                 160

Asp Ile Pro Glu Glu Ile Lys Gln Leu Gln Gln Phe Gln Lys Glu Asp
                165                 170                 175

Ala Ala Ala Thr Ile Tyr Glu Met Leu Gln Asn Ile Phe Ala Ile Phe
            180                 185                 190

Arg Gln Asp Ser Ser Ser Thr Gly Trp Asn Glu Thr Ile Val Glu Asn
        195                 200                 205

Leu Leu Ala Asn Val Tyr His Gln Ile Asn His Leu Lys Thr Val Leu
    210                 215                 220

Glu Glu Lys Leu Glu Lys Glu Asp Phe Thr Arg Gly Lys Leu Met Ser
225                 230                 235                 240

Ser Leu His Leu Lys Arg Tyr Tyr Gly Arg Ile Leu Ala Tyr Leu Lys
                245                 250                 255

Ala Lys Glu Tyr Ser Ala Cys Ala Trp Thr Ile Val Arg Val Glu Ile
            260                 265                 270

Leu Arg Asn Phe Tyr Phe Ile Asn Arg Leu Thr Gly Tyr Leu Arg Asn
        275                 280                 285


<210> SEQ ID NO 9
<211> LENGTH: 288
<212> TYPE: PRT
<213> ORGANISM: Artificial Sequence
<220> FEATURE:
<223> OTHER INFORMATION: An amino acid sequence for human Fc-(linker)-
      IFN-beta (C17S F50A H131A, H140A) starting with the CH3 domain of
      the Fc IgG4 isotype

<400> SEQUENCE: 9

Tyr Lys Thr Thr Pro Pro Val Leu Asp Ser Asp Gly Ser Phe Phe Leu
1               5                   10                  15

Tyr Ser Lys Leu Thr Val Asp Lys Ser Arg Trp Gln Gln Gly Asn Ile
            20                  25                  30

Phe Ser Cys Ser Val Met His Glu Ala Leu His Asn His Tyr Thr Gln
        35                  40                  45

Lys Ser Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95
```

-continued

```
Thr Gln Lys Ser Leu Ser Leu Ser Pro Gly Ala Gly Gly Gly Gly Ser
            100                 105                 110

Gly Gly Gly Gly Ser Gly Gly Gly Ser Gly Met Ser Tyr Asn Leu Leu
        115                 120                 125

Gly Phe Leu Gln Arg Ser Ser Asn Phe Gln Ser Gln Lys Leu Leu Trp
    130                 135                 140

Gln Leu Asn Gly Arg Leu Glu Tyr Cys Leu Lys Asp Arg Met Asn Phe
145                 150                 155                 160

Asp Ile Pro Glu Glu Ile Lys Gln Leu Gln Gln Ala Gln Lys Glu Asp
                165                 170                 175

Ala Ala Leu Thr Ile Tyr Glu Met Leu Gln Asn Ile Phe Ala Ile Phe
            180                 185                 190

Arg Gln Asp Ser Ser Ser Thr Gly Trp Asn Glu Thr Ile Val Glu Asn
        195                 200                 205

Leu Leu Ala Asn Val Tyr His Gln Ile Asn His Leu Lys Thr Val Leu
    210                 215                 220

Glu Glu Lys Leu Glu Lys Glu Asp Phe Thr Arg Gly Lys Leu Met Ser
225                 230                 235                 240

Ser Leu His Leu Lys Arg Tyr Tyr Gly Arg Ile Leu Ala Tyr Leu Lys
                245                 250                 255

Ala Lys Glu Tyr Ser Ala Cys Ala Trp Thr Ile Val Arg Val Glu Ile
            260                 265                 270

Leu Arg Asn Phe Tyr Phe Ile Asn Arg Leu Thr Gly Tyr Leu Arg Asn
        275                 280                 285


<210> SEQ ID NO 10
<211> LENGTH: 288
<212> TYPE: PRT
<213> ORGANISM: Artificial Sequence
<220> FEATURE:
<223> OTHER INFORMATION: An amino acid sequence for human Fc-(linker)-
      IFN-beta (C17S F50A H131A H140T) starting with the CH3 domain of
      the Fc IgG4 isotype

<400> SEQUENCE: 10

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn His Tyr
                85                  90                  95

Thr Gln Lys Ser Leu Ser Leu Ser Pro Gly Ala Gly Gly Gly Gly Ser
            100                 105                 110

Gly Gly Gly Gly Ser Gly Gly Gly Ser Gly Met Ser Tyr Asn Leu Leu
        115                 120                 125

Gly Phe Leu Gln Arg Ser Ser Asn Phe Gln Ser Gln Lys Leu Leu Trp
    130                 135                 140

Gln Leu Asn Gly Arg Leu Glu Tyr Cys Leu Lys Asp Arg Met Asn Phe
145                 150                 155                 160

Asp Ile Pro Glu Glu Ile Lys Gln Leu Gln Gln Ala Gln Lys Glu Asp
```

```
                165                 170                 175

Ala Ala Leu Thr Ile Tyr Glu Met Leu Gln Asn Ile Phe Ala Ile Phe
            180                 185                 190

Arg Gln Asp Ser Ser Ser Thr Gly Trp Asn Glu Thr Ile Val Glu Asn
        195                 200                 205

Leu Leu Ala Asn Val Tyr His Gln Ile Asn His Leu Lys Thr Val Leu
    210                 215                 220

Glu Glu Lys Leu Glu Lys Glu Asp Phe Thr Arg Gly Lys Leu Met Ser
225                 230                 235                 240

Ser Leu His Leu Lys Arg Tyr Tyr Gly Arg Ile Leu Ala Tyr Leu Lys
                245                 250                 255

Ala Lys Glu Tyr Ser Thr Cys Ala Trp Thr Ile Val Arg Val Glu Ile
            260                 265                 270

Leu Arg Asn Phe Tyr Phe Ile Asn Arg Leu Thr Gly Tyr Leu Arg Asn
        275                 280                 285


<210> SEQ ID NO 11
<211> LENGTH: 161
<212> TYPE: PRT
<213> ORGANISM: Mus musculus

<400> SEQUENCE: 11

Ile Asn Tyr Lys Gln Leu Gln Leu Gln Glu Arg Thr Asn Ile Arg Lys
1               5                   10                  15

Cys Gln Glu Leu Leu Glu Gln Leu Asn Gly Lys Ile Asn Leu Thr Tyr
            20                  25                  30

Arg Ala Asp Phe Lys Ile Pro Met Glu Met Thr Glu Lys Met Gln Lys
        35                  40                  45

Ser Tyr Thr Ala Phe Ala Ile Gln Glu Met Leu Gln Asn Val Phe Leu
    50                  55                  60

Val Phe Arg Asn Asn Phe Ser Ser Thr Gly Trp Asn Glu Thr Ile Val
65                  70                  75                  80

Val Arg Leu Leu Asp Glu Leu His Gln Gln Thr Val Phe Leu Lys Thr
                85                  90                  95

Val Leu Glu Glu Lys Gln Glu Glu Arg Leu Thr Trp Glu Met Ser Ser
            100                 105                 110

Thr Ala Leu His Leu Lys Ser Tyr Tyr Trp Arg Val Gln Arg Tyr Leu
        115                 120                 125

Lys Leu Met Lys Tyr Asn Ser Tyr Ala Trp Met Val Val Arg Ala Glu
    130                 135                 140

Ile Phe Arg Asn Phe Leu Ile Ile Arg Arg Leu Thr Arg Asn Phe Gln
145                 150                 155                 160

Asn


<210> SEQ ID NO 12
<211> LENGTH: 161
<212> TYPE: PRT
<213> ORGANISM: Artificial Sequence
<220> FEATURE:
<223> OTHER INFORMATION: An amino acid sequence for mature mouse IFN-
      beta (C17S)

<400> SEQUENCE: 12

Ile Asn Tyr Lys Gln Leu Gln Leu Gln Glu Arg Thr Asn Ile Arg Lys
1               5                   10                  15

Ser Gln Glu Leu Leu Glu Gln Leu Asn Gly Lys Ile Asn Leu Thr Tyr
            20                  25                  30
```

```
Arg Ala Asp Phe Lys Ile Pro Met Glu Met Thr Glu Lys Met Gln Lys
        35                  40                  45

Ser Tyr Thr Ala Phe Ala Ile Gln Glu Met Leu Gln Asn Val Phe Leu
    50                  55                  60

Val Phe Arg Asn Asn Phe Ser Ser Thr Gly Trp Asn Glu Thr Ile Val
65                  70                  75                  80

Val Arg Leu Leu Asp Glu Leu His Gln Gln Thr Val Phe Leu Lys Thr
                85                  90                  95

Val Leu Glu Glu Lys Gln Glu Glu Arg Leu Thr Trp Glu Met Ser Ser
            100                 105                 110

Thr Ala Leu His Leu Lys Ser Tyr Tyr Trp Arg Val Gln Arg Tyr Leu
        115                 120                 125

Lys Leu Met Lys Tyr Asn Ser Tyr Ala Trp Met Val Val Arg Ala Glu
    130                 135                 140

Ile Phe Arg Asn Phe Leu Ile Ile Arg Arg Leu Thr Arg Asn Phe Gln
145                 150                 155                 160

Asn


<210> SEQ ID NO 13
<211> LENGTH: 1409
<212> TYPE: DNA
<213> ORGANISM: Artificial Sequence
<220> FEATURE:
<223> OTHER INFORMATION: A nucleic acid encoding the fusion protein
      huFcg4h-IFN-beta (C17S) starting from the hinge

<400> SEQUENCE: 13

gagcccaaat cttctgacaa aactcacaca tgcccaccgt gcccaggtaa gccagcccag     60

gcctcgccct ccagctcaag gcgggacagg tgccctagag tagcctgcat ccagggacag    120

gccccagccg ggtgctgacg catccacctc catctcttcc tcagcacctg agttcctggg    180

gggaccatca gtcttcctgt tccccccaaa acccaaggac actctcatga tctcccggac    240

ccctgaggtc acgtgcgtgg tggtggacgt gagccaggaa gaccccgagg tccagttcaa    300

ctggtacgtg gatggcgtgg aggtgcataa tgccaagaca aagccgcggg aggagcagtt    360

caacagcacg taccgtgtgg tcagcgtcct caccgtcctg caccaggact ggctgaacgg    420

caaggagtac aagtgcaagg tctccaacaa aggcctcccg tcctccatcg agaaaaccat    480

ctccaaagcc aaaggtggga cccacggggt gcgagggcca catggacaga ggtcagctcg    540

gcccaccctc tgccctggga gtgaccgctg tgccaacctc tgtccctaca gggcagcccc    600

gagagccaca ggtgtacacc ctgcccccat cccaggagga gatgaccaag aaccaggtca    660

gcctgacctg cctggtcaaa ggcttctacc ccagcgacat cgccgtggag tgggagagca    720

atgggcagcc ggagaacaac tacaagacca cgcctcccgt gctggactcc gacggctcct    780

tcttcctcta cagcaagctc accgtggaca agagcaggtg gcagcagggg aacatcttct    840

catgctccgt gatgcatgag gctctgcaca accactacac gcagaagagc ctctccctgt    900

ccccgggtat gagctacaac ttgcttggat tcctacaaag aagcagcaat tttcagagtc    960

agaagctcct gtggcaattg aatgggaggc ttgaatattg cctcaaggac aggatgaact   1020

ttgacatccc tgaggagatt aagcagctgc agcagttcca gaaggaggac gccgcattga   1080

ccatctatga gatgctccag aacatctttg ctattttcag acaagattca tctagcactg   1140

gctggaatga gactattgtt gagaacctcc tggctaatgt ctatcatcag ataaaccatc   1200

tgaagacagt cctggaagaa aaactggaga aagaagattt caccagggga aaactcatga   1260

gcagtctgca cctgaaaaga tattatggga ggattctgca ttacctgaag gccaaggagt   1320
```

-continued

```
acagtcactg tgcctggacc atagtcagag tggaaatcct aaggaacttt tacttcatta   1380

acagacttac aggttacctc cgaaactga                                     1409


<210> SEQ ID NO 14
<211> LENGTH: 6353
<212> TYPE: DNA
<213> ORGANISM: Artificial Sequence
<220> FEATURE:
<223> OTHER INFORMATION: A linearized nucleic acid sequence of the pdCs
      vector containing huFcg4h-(linker)-IFN-beta (C17S)

<400> SEQUENCE: 14

gtcgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggagt atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360

tattagtcat cgctattacc atggtgatgc ggttttggca gtacatcaat gggcgtggat    420

agcggtttga ctcacgggga tttccaagtc tccaccccat tgacgtcaat gggagtttgt    480

tttggcacca aaatcaacgg gactttccaa aatgtcgtaa caactccgcc ccattgacgc    540

aaatgggcgg taggcgtgta cggtgggagg tctatataag cagagctctc tggctaacta    600

cagaacccac tgcttactgg cttatcgaaa ttaatacgac tcactatagg gagaccctct    660

agaccaccat ggagttgcct gttaggctgt tggtgctgat gttctggatt cctggtgagg    720

agagagggaa gtgagggagg agaatggaca gggagcagga gcactgaatc ccattgctca    780

ttccatgtat ctggcatggg tgagaagatg ggtcttatcc tccagcatgg ggcctctggg    840

gtgaatactt gttagaggga ggttccagat gggaacatgt gctataatga agattatgaa    900

atggagcctg ggatggtcta agtaatgcct tagaagtgac tagacacttg caattcactt    960

tttttggtaa gaagagattt ttaggctata aaaaaatgtt atgtaaaaat aaacgatcac   1020

agttgaaata aaaaaaaaat ataaggatgt tcatgaattt tgtgtataac tatgtatttc   1080

tctctcattg tttcagcttc cttaagcgag cccaaatctt ctgacaaaac tcacacatgc   1140

ccaccgtgcc caggtaagcc agcccaggcc tcgccctcca gctcaaggcg ggacaggtgc   1200

cctagagtag cctgcatcca gggacaggcc ccagccgggt gctgacgcat ccacctccat   1260

ctcttcctca gcacctgagt tcctgggggg accatcagtc ttcctgttcc ccccaaaacc   1320

caaggacact ctcatgatct cccggacccc tgaggtcacg tgcgtggtgg tggacgtgag   1380

ccaggaagac cccgaggtcc agttcaactg gtacgtggat ggcgtggagg tgcataatgc   1440

caagacaaag ccgcgggagg agcagttcaa cagcacgtac cgtgtggtca gcgtcctcac   1500

cgtcctgcac caggactggc tgaacggcaa ggagtacaag tgcaaggtct ccaacaaagg   1560

cctcccgtcc tccatcgaga aaaccatctc caaagccaaa ggtgggaccc acggggtgcg   1620

agggccacat ggacagaggt cagctcggcc caccctctgc cctgggagtg accgctgtgc   1680

caacctctgt ccctacaggg cagccccgag agccacaggt gtacaccctg cccccatccc   1740

aggaggagat gaccaagaac caggtcagcc tgacctgcct ggtcaaaggc ttctacccca   1800

gcgacatcgc cgtggagtgg gagagcaatg ggcagccgga gaacaactac aagaccacgc   1860

ctcccgtgct ggactccgac ggctccttct tcctctacag caagctcacc gtggacaaga   1920
```

```
gcaggtggca gcaggggaac atcttctcat gctccgtgat gcatgaggct ctgcacaacc   1980
actacacgca gaagagcctc tccctgtccc cgggtgcagg gggcgggggc agcgggggcg   2040
gaggatccgg cgggggctcg ggtatgagct acaacttgct tggattccta caaagaagca   2100
gcaattttca gagtcagaag ctcctgtggc aattgaatgg gaggcttgaa tattgcctca   2160
aggacaggat gaactttgac atccctgagg agattaagca gctgcagcag ttccagaagg   2220
aggacgccgc attgaccatc tatgagatgc tccagaacat ctttgctatt ttcagacaag   2280
attcatctag cactggctgg aatgagacta ttgttgagaa cctcctggct aatgtctatc   2340
atcagataaa ccatctgaag acagtcctgg aagaaaaact ggagaaagaa gatttcacca   2400
ggggaaaact catgagcagt ctgcacctga aaagatatta tgggaggatt ctgcattacc   2460
tgaaggccaa ggagtacagt cactgtgcct ggaccatagt cagagtggaa atcctaagga   2520
acttttactt cattaacaga cttacaggtt acctccgaaa ctgactcgag ggatccagac   2580
atgataagat acattgatga gtttggacaa accacaacta gaatgcagtg aaaaaaatgc   2640
tttatttgtg aaatttgtga tgctattgct ttatttgtaa ccattagaag ctgcaataaa   2700
caagttaaca acaacaattg cattcatttt atgtttcagg ttcaggggga ggtgtgggag   2760
gttttttaaa gcaagtaaaa cctctacaaa tgtggtatgg ctgattatga tcctgcctcg   2820
cgcgtttcgg tgatgacggt gaaaacctct gacacatgca gctcccggag acggtcacag   2880
cttgtctgta agcggatgcc gggagcagac aagcccgtca gggcgcgtca gcgggtgttg   2940
gcgggtgtcg gggcgcagcc atgacccagt cacgtagcga tagcggagtg tatactggct   3000
taactatgcg gcatcagagc agattgtact gagagtgcac catatgcggt gtgaaatacc   3060
gcacagatgc gtaaggagaa aataccgcat caggcgctct tccgcttcct cgctcactga   3120
ctcgctgcgc tcggtcgttc ggctgcggcg agcggtatca gctcactcaa aggcggtaat   3180
acggttatcc acagaatcag gggataacgc aggaaagaac atgtgagcaa aaggccagca   3240
aaaggccagg aaccgtaaaa aggccgcgtt gctggcgttt ttccataggc tccgcccccc   3300
tgacgagcat cacaaaaatc gacgctcaag tcagaggtgg cgaaacccga caggactata   3360
aagataccag gcgtttcccc ctggaagctc cctcgtgcgc tctcctgttc cgaccctgcc   3420
gcttaccgga tacctgtccg cctttctccc ttcgggaagc gtggcgcttt ctcaatgctc   3480
acgctgtagg tatctcagtt cggtgtaggt cgttcgctcc aagctgggct gtgtgcacga   3540
accccccgtt cagcccgacc gctgcgcctt atccggtaac tatcgtcttg agtccaaccc   3600
ggtaagacac gacttatcgc cactggcagc agccactggt aacaggatta gcagagcgag   3660
gtatgtaggc ggtgctacag agttcttgaa gtggtggcct aactacggct acactagaag   3720
gacagtattt ggtatctgcg ctctgctgaa gccagttacc ttcggaaaaa gagttggtag   3780
ctcttgatcc ggcaaacaaa ccaccgctgg tagcggtggt ttttttgttt gcaagcagca   3840
gattacgcgc agaaaaaaag gatctcaaga agatcctttg atcttttcta cggggtctga   3900
cgctcagtgg aacgaaaact cacgttaagg gattttggtc atgagattat caaaaaggat   3960
cttcacctag atccttttaa attaaaaatg aagttttaaa tcaatctaaa gtatatatga   4020
gtaaacttgg tctgacagtt accaatgctt aatcagtgag gcacctatct cagcgatctg   4080
tctatttcgt tcatccatag ttgcctgact ccccgtcgtg tagataacta cgatacggga   4140
gggcttacca tctggcccca gtgctgcaat gataccgcga gacccacgct caccggctcc   4200
agatttatca gcaataaacc agccagccgg aagggccgag cgcagaagtg gtcctgcaac   4260
tttatccgcc tccatccagt ctattaattg ttgccgggaa gctagagtaa gtagttcgcc   4320
```

-continued

```
agttaatagt ttgcgcaacg ttgttgccat tgctgcaggc atcgtggtgt cacgctcgtc   4380

gtttggtatg gcttcattca gctccggttc ccaacgatca aggcgagtta catgatcccc   4440

catgttgtgc aaaaaagcgg ttagctcctt cggtcctccg atcgttgtca gaagtaagtt   4500

ggccgcagtg ttatcactca tggttatggc agcactgcat aattctctta ctgtcatgcc   4560

atccgtaaga tgcttttctg tgactggtga gtactcaacc aagtcattct gagaatagtg   4620

tatgcggcga ccgagttgct cttgcccggc gtcaacacgg gataataccg cgccacatag   4680

cagaacttta aaagtgctca tcattggaaa acgttcttcg gggcgaaaac tctcaaggat   4740

cttaccgctg ttgagatcca gttcgatgta acccactcgt gcacccaact gatcttcagc   4800

atcttttact ttcaccagcg tttctgggtg agcaaaaaca ggaaggcaaa atgccgcaaa   4860

aaagggaata agggcgacac ggaaatgttg aatactcata ctcttccttt ttcaatatta   4920

ttgaagcatt tatcagggtt attgtctcat gagcggatac atatttgaat gtatttagaa   4980

aaataaacaa ataggggttc cgcgcacatt tccccgaaaa gtgccacctg acgtctaaga   5040

aaccattatt atcatgacat taacctataa aaataggcgt atcacgaggc cctttcgtct   5100

tcaagaattc cgatccagac atgataagat acattgatga gtttggacaa accacaacta   5160

gaatgcagtg aaaaaaatgc tttatttgtg aaatttgtga tgctattgct ttatttgtaa   5220

ccattagaag ctgcaataaa caagttaaca acaacaattg cattcatttt atgtttcagg   5280

ttcaggggga ggtgtgggag gtttttttaaa gcaagtaaaa cctctacaaa tgtggtatgg   5340

ctgattatga tctaaagcca gcaaaagtcc catggtctta taaaaatgca tagctttcgg   5400

aggggagcag agaacttgaa agcatcttcc tgttagtctt tcttctcgta gaccttaaat   5460

tcatacttga ttcctttttc ctcctggacc tcagagagga cgcctgggta ttctgggaga   5520

agtttatatt tccccaaatc aatttctggg aaaaacgtgt cactttcaaa ttcctgcatg   5580

atccttgtca caaagagtct gaggtggcct ggttgattca tggcttcctg gtaaacagaa   5640

ctgcctccga ctatccaaac catgtctact ttacttgcca attccggttg ttcaataagt   5700

cttaaggcat catccaaact tttggcaaga aaatgagctc ctcgtggtgg ttctttgagt   5760

tctctactga gaactatatt aattctgtcc tttaaaggtc gattcttctc aggaatggag   5820

aaccaggttt tcctacccat aatcaccaga ttctgtttac cttccactga agaggttgtg   5880

gtcattcttt ggaagtactt gaactcgttc ctgagcggag gccagggtcg gtctccgttc   5940

ttgccaatcc ccatattttg ggacacggcg acgatgcagt tcaatggtcg aaccatgagg   6000

gcaccaagct agctttttgc aaaagcctag gcctccaaaa aagcctcctc actacttctg   6060

gaatagctca gaggccgagg cggcctcggc ctctgcataa ataaaaaaaa ttagtcagcc   6120

atggggcgga gaatgggcgg aactgggcgg agttaggggc gggatgggcg gagttagggg   6180

cgggactatg gttgctgact aattgagatg catgctttgc atacttctgc ctgctgggga   6240

gcctggggac tttccacacc tggttgctga ctaattgaga tgcatgcttt gcatacttct   6300

gcctgctggg gagcctgggg actttccaca ccctaactga cacacattcc aca          6353
```

<210> SEQ ID NO 15
<211> LENGTH: 1457
<212> TYPE: DNA
<213> ORGANISM: Artificial Sequence
<220> FEATURE:
<223> OTHER INFORMATION: A nucleic acid sequence encoding the fusion protein HuFc-g4h-(linker)-IFN-beta (C17S) starting from the hinge

<400> SEQUENCE: 15

```
gagcccaaat cttctgacaa aactcacaca tgcccaccgt gcccaggtaa gccagcccag     60
```

gcctcgccct ccagctcaag gcgggacagg tgccctagag tagcctgcat ccagggacag 120
gccccagccg ggtgctgacg catccacctc catctcttcc tcagcacctg agttcctggg 180
gggaccatca gtcttcctgt tccccccaaa acccaaggac actctcatga tctcccggac 240
ccctgaggtc acgtgcgtgg tggtggacgt gagccaggaa gaccccgagg tccagttcaa 300
ctggtacgtg gatggcgtgg aggtgcataa tgccaagaca aagccgcggg aggagcagtt 360
caacagcacg taccgtgtgg tcagcgtcct caccgtcctg caccaggact ggctgaacgg 420
caaggagtac aagtgcaagg tctccaacaa aggcctcccg tcctccatcg agaaaaccat 480
ctccaaagcc aaaggtggga cccacggggt gcgagggcca catggacaga ggtcagctcg 540
gcccaccctc tgccctggga gtgaccgctg tgccaacctc tgtccctaca gggcagcccc 600
gagagccaca ggtgtacacc ctgcccccat cccaggagga gatgaccaag aaccaggtca 660
gcctgacctg cctggtcaaa ggcttctacc ccagcgacat cgccgtggag tgggagagca 720
atgggcagcc ggagaacaac tacaagacca cgcctcccgt gctggactcc gacggctcct 780
tcttcctcta cagcaagctc accgtggaca agagcaggtg gcagcagggg aacatcttct 840
catgctccgt gatgcatgag gctctgcaca accactacac gcagaagagc ctctccctgt 900
ccccgggtgc agggggcggg ggcagcgggg gcggaggatc cggcgggggc tcgggtatga 960
gctacaactt gcttggattc ctacaaagaa gcagcaattt tcagagtcag aagctcctgt 1020
ggcaattgaa tgggaggctt gaatattgcc tcaaggacag gatgaacttt gacatccctg 1080
aggagattaa gcagctgcag cagttccaga aggaggacgc cgcattgacc atctatgaga 1140
tgctccagaa catctttgct attttcagac aagattcatc tagcactggc tggaatgaga 1200
ctattgttga gaacctcctg gctaatgtct atcatcagat aaaccatctg aagacagtcc 1260
tggaagaaaa actggagaaa gaagatttca ccaggggaaa actcatgagc agtctgcacc 1320
tgaaaagata ttatgggagg attctgcatt acctgaaggc caaggagtac agtcactgtg 1380
cctggaccat agtcagagtg gaaatcctaa ggaactttta cttcattaac agacttacag 1440
gttacctccg aaactga 1457

<210> SEQ ID NO 16
<211> LENGTH: 6353
<212> TYPE: DNA
<213> ORGANISM: Artificial Sequence
<220> FEATURE:
<223> OTHER INFORMATION: A linearized nucleic acid sequence of the pdCs vector containing huFcg4h-(linker)-IFN-beta (C17S L57A H131A H140A)

<400> SEQUENCE: 16
gtcgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600

-continued

```
cagaacccac tgcttactgg cttatcgaaa ttaatacgac tcactatagg gagaccctct    660
agaccaccat ggagttgcct gttaggctgt tggtgctgat gttctggatt cctggtgagg    720
agagagggaa gtgagggagg agaatggaca gggagcagga gcactgaatc ccattgctca    780
ttccatgtat ctggcatggg tgagaagatg ggtcttatcc tccagcatgg ggcctctggg    840
gtgaatactt gttagaggga ggttccagat gggaacatgt gctataatga agattatgaa    900
atggagcctg ggatggtcta agtaatgcct tagaagtgac tagacacttg caattcactt    960
tttttggtaa gaagagattt ttaggctata aaaaaatgtt atgtaaaaat aaacgatcac   1020
agttgaaata aaaaaaaaat ataaggatgt tcatgaattt tgtgtataac tatgtatttc   1080
tctctcattg tttcagcttc cttaagcgag cccaaatctt ctgacaaaac tcacacatgc   1140
ccaccgtgcc caggtaagcc agcccaggcc tcgccctcca gctcaaggcg ggacaggtgc   1200
cctagagtag cctgcatcca gggacaggcc ccagccgggt gctgacgcat ccacctccat   1260
ctcttcctca gcacctgagt tcctgggggg accatcagtc ttcctgttcc ccccaaaacc   1320
caaggacact ctcatgatct cccggacccc tgaggtcacg tgcgtggtgg tggacgtgag   1380
ccaggaagac cccgaggtcc agttcaactg gtacgtggat ggcgtggagg tgcataatgc   1440
caagacaaag ccgcgggagg agcagttcaa cagcacgtac cgtgtggtca gcgtcctcac   1500
cgtcctgcac caggactggc tgaacggcaa ggagtacaag tgcaaggtct ccaacaaagg   1560
cctcccgtcc tccatcgaga aaaccatctc caaagccaaa ggtgggaccc acggggtgcg   1620
agggccacat ggacagaggt cagctcggcc caccctctgc cctgggagtg accgctgtgc   1680
caacctctgt ccctacaggg cagccccgag agccacaggt gtacaccctg cccccatccc   1740
aggaggagat gaccaagaac caggtcagcc tgacctgcct ggtcaaaggc ttctacccca   1800
gcgacatcgc cgtggagtgg gagagcaatg ggcagccgga gaacaactac aagaccacgc   1860
ctcccgtgct ggactccgac ggctccttct tcctctacag caagctcacc gtggacaaga   1920
gcaggtggca gcaggggaac atcttctcat gctccgtgat gcatgaggct ctgcacaacc   1980
actacacgca gaagagcctc tccctgtccc cgggtgcagg gggcgggggc agcgggggcg   2040
gaggatccgg cgggggctcg ggtatgagct acaacttgct tggattccta caaagaagca   2100
gcaattttca gagtcagaag ctcctgtggc aattgaatgg gaggcttgaa tattgcctca   2160
aggacaggat gaactttgac atccctgagg agattaagca gctgcagcag ttccagaagg   2220
aggacgccgc agccaccatc tatgagatgc tccagaacat ctttgctatt ttcagacaag   2280
attcatctag cactggctgg aatgagacta ttgttgagaa cctcctggct aatgtctatc   2340
atcagataaa ccatctgaag acagtcctgg aagaaaaact ggagaaagaa gatttcacca   2400
ggggaaaact catgagcagt ctgcacctga aaagatatta tgggaggatt ctggcctacc   2460
tgaaggccaa ggagtacagt gcctgtgcct ggaccatagt cagagtggaa atcctaagga   2520
acttttactt cattaacaga cttacaggtt acctccgaaa ctgactcgag ggatccagac   2580
atgataagat acattgatga gtttggacaa accacaacta gaatgcagtg aaaaaaatgc   2640
tttatttgtg aaatttgtga tgctattgct ttatttgtaa ccattagaag ctgcaataaa   2700
caagttaaca acaacaattg cattcatttt atgtttcagg ttcaggggga ggtgtgggag   2760
gttttttaaa gcaagtaaaa cctctacaaa tgtggtatgg ctgattatga tcctgcctcg   2820
cgcgtttcgg tgatgacggt gaaaacctct gacacatgca gctcccggag acggtcacag   2880
cttgtctgta agcggatgcc gggagcagac aagcccgtca gggcgcgtca gcgggtgttg   2940
gcgggtgtcg gggcgcagcc atgacccagt cacgtagcga tagcggagtg tatactggct   3000
```

-continued taactatgcg gcatcagagc agattgtact gagagtgcac catatgcggt gtgaaatacc 3060
gcacagatgc gtaaggagaa aataccgcat caggcgctct tccgcttcct cgctcactga 3120
ctcgctgcgc tcggtcgttc ggctgcggcg agcggtatca gctcactcaa aggcggtaat 3180
acggttatcc acagaatcag gggataacgc aggaaagaac atgtgagcaa aaggccagca 3240
aaaggccagg aaccgtaaaa aggccgcgtt gctggcgttt ttccataggc tccgcccccc 3300
tgacgagcat cacaaaaatc gacgctcaag tcagaggtgg cgaaacccga caggactata 3360
aagataccag gcgtttcccc ctggaagctc cctcgtgcgc tctcctgttc cgaccctgcc 3420
gcttaccgga tacctgtccg cctttctccc ttcgggaagc gtggcgcttt ctcaatgctc 3480
acgctgtagg tatctcagtt cggtgtaggt cgttcgctcc aagctgggct gtgtgcacga 3540
accccccgtt cagcccgacc gctgcgcctt atccggtaac tatcgtcttg agtccaaccc 3600
ggtaagacac gacttatcgc cactggcagc agccactggt aacaggatta gcagagcgag 3660
gtatgtaggc ggtgctacag agttcttgaa gtggtggcct aactacggct acactagaag 3720
gacagtattt ggtatctgcg ctctgctgaa gccagttacc ttcggaaaaa gagttggtag 3780
ctcttgatcc ggcaaacaaa ccaccgctgg tagcggtggt ttttttgttt gcaagcagca 3840
gattacgcgc agaaaaaaag gatctcaaga agatcctttg atcttttcta cggggtctga 3900
cgctcagtgg aacgaaaact cacgttaagg gattttggtc atgagattat caaaaaggat 3960
cttcacctag atccttttaa attaaaaatg aagttttaaa tcaatctaaa gtatatatga 4020
gtaaacttgg tctgacagtt accaatgctt aatcagtgag gcacctatct cagcgatctg 4080
tctatttcgt tcatccatag ttgcctgact ccccgtcgtg tagataacta cgatacggga 4140
gggcttacca tctggcccca gtgctgcaat gataccgcga gacccacgct caccggctcc 4200
agatttatca gcaataaacc agccagccgg aagggccgag cgcagaagtg gtcctgcaac 4260
tttatccgcc tccatccagt ctattaattg ttgccgggaa gctagagtaa gtagttcgcc 4320
agttaatagt ttgcgcaacg ttgttgccat tgctgcaggc atcgtggtgt cacgctcgtc 4380
gtttggtatg gcttcattca gctccggttc ccaacgatca aggcgagtta catgatcccc 4440
catgttgtgc aaaaaagcgg ttagctcctt cggtcctccg atcgttgtca gaagtaagtt 4500
ggccgcagtg ttatcactca tggttatggc agcactgcat aattctctta ctgtcatgcc 4560
atccgtaaga tgcttttctg tgactggtga gtactcaacc aagtcattct gagaatagtg 4620
tatgcggcga ccgagttgct cttgcccggc gtcaacacgg gataataccg cgccacatag 4680
cagaacttta aaagtgctca tcattggaaa acgttcttcg gggcgaaaac tctcaaggat 4740
cttaccgctg ttgagatcca gttcgatgta acccactcgt gcacccaact gatcttcagc 4800
atcttttact ttcaccagcg tttctgggtg agcaaaaaca ggaaggcaaa atgccgcaaa 4860
aaagggaata agggcgacac ggaaatgttg aatactcata ctcttccttt ttcaatatta 4920
ttgaagcatt tatcagggtt attgtctcat gagcggatac atatttgaat gtatttagaa 4980
aaataaacaa ataggggttc cgcgcacatt tccccgaaaa gtgccacctg acgtctaaga 5040
aaccattatt atcatgacat taacctataa aaataggcgt atcacgaggc cctttcgtct 5100
tcaagaattc cgatccagac atgataagat acattgatga gtttggacaa accacaacta 5160
gaatgcagtg aaaaaaatgc tttatttgtg aaatttgtga tgctattgct ttatttgtaa 5220
ccattagaag ctgcaataaa caagttaaca acaacaattg cattcatttt atgtttcagg 5280
ttcaggggga ggtgtgggag gtttttttaaa gcaagtaaaa cctctacaaa tgtggtatgg 5340
ctgattatga tctaaagcca gcaaaagtcc catggtctta taaaaatgca tagctttcgg 5400
aggggagcag agaacttgaa agcatcttcc tgttagtctt tcttctcgta gaccttaaat 5460
tcatacttga ttccttttc ctcctggacc tcagagagga cgcctgggta ttctgggaga 5520
agtttatatt tccccaaatc aatttctggg aaaaacgtgt cactttcaaa ttcctgcatg 5580
atccttgtca caaagagtct gaggtggcct ggttgattca tggcttcctg gtaaacagaa 5640
ctgcctccga ctatccaaac catgtctact ttacttgcca attccggttg ttcaataagt 5700
cttaaggcat catccaaact tttggcaaga aaatgagctc ctcgtggtgg ttctttgagt 5760
tctctactga gaactatatt aattctgtcc tttaaaggtc gattcttctc aggaatggag 5820
aaccaggttt tcctacccat aatcaccaga ttctgtttac cttccactga agaggttgtg 5880
gtcattcttt ggaagtactt gaactcgttc ctgagcggag gccagggtcg gtctccgttc 5940
ttgccaatcc ccatattttg ggacacggcg acgatgcagt tcaatggtcg aaccatgagg 6000
gcaccaagct agctttttgc aaaagcctag gcctccaaaa aagcctcctc actacttctg 6060
gaatagctca gaggccgagg cggcctcggc ctctgcataa ataaaaaaaa ttagtcagcc 6120
atggggcgga gaatgggcgg aactgggcgg agttaggggc gggatgggcg gagttagggg 6180
cgggactatg gttgctgact aattgagatg catgctttgc atacttctgc ctgctgggga 6240
gcctggggac tttccacacc tggttgctga ctaattgaga tgcatgcttt gcatacttct 6300
gcctgctggg gagcctgggg actttccaca ccctaactga cacacattcc aca 6353

<210> SEQ ID NO 17
<211> LENGTH: 1457
<212> TYPE: DNA
<213> ORGANISM: Artificial Sequence
<220> FEATURE:
<223> OTHER INFORMATION: A nucleic acid sequence of huFcg4h-(linker)-
IFN-beta (C17S L57A H131 H140A) starting from the hinge

<400> SEQUENCE: 17
gagcccaaat cttctgacaa aactcacaca tgcccaccgt gcccaggtaa gccagcccag 60
gcctcgccct ccagctcaag gcgggacagg tgccctagag tagcctgcat ccagggacag 120
gccccagccg ggtgctgacg catccacctc catctcttcc tcagcacctg agttcctggg 180
gggaccatca gtcttcctgt tccccccaaa acccaaggac actctcatga tctcccggac 240
ccctgaggtc acgtgcgtgg tggtggacgt gagccaggaa gaccccgagg tccagttcaa 300
ctggtacgtg gatggcgtgg aggtgcataa tgccaagaca aagccgcggg aggagcagtt 360
caacagcacg taccgtgtgg tcagcgtcct caccgtcctg caccaggact ggctgaacgg 420
caaggagtac aagtgcaagg tctccaacaa aggcctcccg tcctccatcg agaaaaccat 480
ctccaaagcc aaaggtggga cccacggggt gcgagggcca catggacaga ggtcagctcg 540
gcccaccctc tgccctggga gtgaccgctg tgccaacctc tgtccctaca gggcagcccc 600
gagagccaca ggtgtacacc ctgcccccat cccaggagga gatgaccaag aaccaggtca 660
gcctgacctg cctggtcaaa ggcttctacc ccagcgacat cgccgtggag tgggagagca 720
atgggcagcc ggagaacaac tacaagacca cgcctcccgt gctggactcc gacggctcct 780
tcttcctcta cagcaagctc accgtggaca agagcaggtg gcagcagggg aacatcttct 840
catgctccgt gatgcatgag gctctgcaca accactacac gcagaagagc ctctccctgt 900
ccccgggtgc agggggcggg ggcagcgggg gcggaggatc cggcgggggc tcgggtatga 960
gctacaactt gcttggattc ctacaaagaa gcagcaattt tcagagtcag aagctcctgt 1020
ggcaattgaa tgggaggctt gaatattgcc tcaaggacag gatgaacttt gacatccctg 1080

-continued aggagattaa gcagctgcag cagttccaga aggaggacgc cgcagccacc atctatgaga 1140
tgctccagaa catctttgct attttcagac aagattcatc tagcactggc tggaatgaga 1200
ctattgttga gaacctcctg gctaatgtct atcatcagat aaaccatctg aagacagtcc 1260
tggaagaaaa actggagaaa gaagatttca ccaggggaaa actcatgagc agtctgcacc 1320
tgaaaagata ttatgggagg attctggcct acctgaaggc caaggagtac agtgcctgtg 1380
cctggaccat agtcagagtg gaaatcctaa ggaactttta cttcattaac agacttacag 1440
gttacctccg aaactga 1457

<210> SEQ ID NO 18
<211> LENGTH: 6353
<212> TYPE: DNA
<213> ORGANISM: Artificial Sequence
<220> FEATURE:
<223> OTHER INFORMATION: A linearized nucleic acid sequence of the pdCs vector containing huFcg4h-(linker)-IFN-beta (C17S F50H H131A H140A)

<400> SEQUENCE: 18
gtcgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600
cagaacccac tgcttactgg cttatcgaaa ttaatacgac tcactatagg gagaccctct 660
agaccaccat ggagttgcct gttaggctgt tggtgctgat gttctggatt cctggtgagg 720
agagagggaa gtgagggagg agaatggaca gggagcagga gcactgaatc ccattgctca 780
ttccatgtat ctggcatggg tgagaagatg ggtcttatcc tccagcatgg ggcctctggg 840
gtgaatactt gttagaggga ggttccagat gggaacatgt gctataatga agattatgaa 900
atggagcctg ggatggtcta agtaatgcct tagaagtgac tagacacttg caattcactt 960
tttttggtaa gaagagattt ttaggctata aaaaaatgtt atgtaaaaat aaacgatcac 1020
agttgaaata aaaaaaaaat ataaggatgt tcatgaattt tgtgtataac tatgtatttc 1080
tctctcattg tttcagcttc cttaagcgag cccaaatctt ctgacaaaac tcacacatgc 1140
ccaccgtgcc caggtaagcc agcccaggcc tcgccctcca gctcaaggcg ggacaggtgc 1200
cctagagtag cctgcatcca gggacaggcc ccagccgggt gctgacgcat ccacctccat 1260
ctcttcctca gcacctgagt tcctgggggg accatcagtc ttcctgttcc ccccaaaacc 1320
caaggacact ctcatgatct cccggacccc tgaggtcacg tgcgtggtgg tggacgtgag 1380
ccaggaagac cccgaggtcc agttcaactg gtacgtggat ggcgtggagg tgcataatgc 1440
caagacaaag ccgcgggagg agcagttcaa cagcacgtac cgtgtggtca gcgtcctcac 1500
cgtcctgcac caggactggc tgaacggcaa ggagtacaag tgcaaggtct ccaacaaagg 1560
cctcccgtcc tccatcgaga aaaccatctc caaagccaaa ggtgggaccc acggggtgcg 1620

-continued

```
agggccacat ggacagaggt cagctcggcc caccctctgc cctgggagtg accgctgtgc   1680
caacctctgt ccctacaggg cagccccgag agccacaggt gtacaccctg cccccatccc   1740
aggaggagat gaccaagaac caggtcagcc tgacctgcct ggtcaaaggc ttctacccca   1800
gcgacatcgc cgtggagtgg gagagcaatg ggcagccgga gaacaactac aagaccacgc   1860
ctcccgtgct ggactccgac ggctccttct tcctctacag caagctcacc gtggacaaga   1920
gcaggtggca gcaggggaac atcttctcat gctccgtgat gcatgaggct ctgcacaacc   1980
actacacgca gaagagcctc tccctgtccc cgggtgcagg gggcgggggc agcgggggcg   2040
gaggatccgg cgggggctcg ggtatgagct acaacttgct tggattccta caaagaagca   2100
gcaattttca gagtcagaag ctcctgtggc aattgaatgg gaggcttgaa tattgcctca   2160
aggacaggat gaactttgac atccctgagg agattaagca gctgcagcag catcagaagg   2220
aggacgccgc attgaccatc tatgagatgc tccagaacat ctttgctatt ttcagacaag   2280
attcatctag cactggctgg aatgagacta ttgttgagaa cctcctggct aatgtctatc   2340
atcagataaa ccatctgaag acagtcctgg aagaaaaact ggagaaagaa gatttcacca   2400
ggggaaaact catgagcagt ctgcacctga aaagatatta tgggaggatt ctggcctacc   2460
tgaaggccaa ggagtacagt gcctgtgcct ggaccatagt cagagtggaa atcctaagga   2520
acttttactt cattaacaga cttacaggtt acctccgaaa ctgactcgag ggatccagac   2580
atgataagat acattgatga gtttggacaa accacaacta gaatgcagtg aaaaaaatgc   2640
tttatttgtg aaatttgtga tgctattgct ttatttgtaa ccattagaag ctgcaataaa   2700
caagttaaca acaacaattg cattcatttt atgtttcagg ttcaggggga ggtgtgggag   2760
gttttttaaa gcaagtaaaa cctctacaaa tgtggtatgg ctgattatga tcctgcctcg   2820
cgcgtttcgg tgatgacggt gaaaacctct gacacatgca gctcccggag acggtcacag   2880
cttgtctgta agcggatgcc gggagcagac aagcccgtca gggcgcgtca gcgggtgttg   2940
gcgggtgtcg gggcgcagcc atgacccagt cacgtagcga tagcggagtg tatactggct   3000
taactatgcg gcatcagagc agattgtact gagagtgcac catatgcggt gtgaaatacc   3060
gcacagatgc gtaaggagaa aataccgcat caggcgctct tccgcttcct cgctcactga   3120
ctcgctgcgc tcggtcgttc ggctgcggcg agcggtatca gctcactcaa aggcggtaat   3180
acggttatcc acagaatcag gggataacgc aggaaagaac atgtgagcaa aaggccagca   3240
aaaggccagg aaccgtaaaa aggccgcgtt gctggcgttt ttccataggc tccgcccccc   3300
tgacgagcat cacaaaaatc gacgctcaag tcagaggtgg cgaaacccga caggactata   3360
aagataccag gcgtttcccc ctggaagctc cctcgtgcgc tctcctgttc cgaccctgcc   3420
gcttaccgga tacctgtccg cctttctccc ttcgggaagc gtggcgcttt ctcaatgctc   3480
acgctgtagg tatctcagtt cggtgtaggt cgttcgctcc aagctgggct gtgtgcacga   3540
accccccgtt cagcccgacc gctgcgcctt atccggtaac tatcgtcttg agtccaaccc   3600
ggtaagacac gacttatcgc cactggcagc agccactggt aacaggatta gcagagcgag   3660
gtatgtaggc ggtgctacag agttcttgaa gtggtggcct aactacggct acactagaag   3720
gacagtattt ggtatctgcg ctctgctgaa gccagttacc ttcggaaaaa gagttggtag   3780
ctcttgatcc ggcaaacaaa ccaccgctgg tagcggtggt ttttttgttt gcaagcagca   3840
gattacgcgc agaaaaaaag gatctcaaga agatcctttg atcttttcta cggggtctga   3900
cgctcagtgg aacgaaaact cacgttaagg gattttggtc atgagattat caaaaaggat   3960
cttcacctag atccttttaa attaaaaatg aagttttaaa tcaatctaaa gtatatatga   4020
```

-continued gtaaacttgg tctgacagtt accaatgctt aatcagtgag gcacctatct cagcgatctg 4080
tctatttcgt tcatccatag ttgcctgact ccccgtcgtg tagataacta cgatacggga 4140
gggcttacca tctggcccca gtgctgcaat gataccgcga gacccacgct caccggctcc 4200
agatttatca gcaataaacc agccagccgg aagggccgag cgcagaagtg gtcctgcaac 4260
tttatccgcc tccatccagt ctattaattg ttgccgggaa gctagagtaa gtagttcgcc 4320
agttaatagt ttgcgcaacg ttgttgccat tgctgcaggc atcgtggtgt cacgctcgtc 4380
gtttggtatg gcttcattca gctccggttc ccaacgatca aggcgagtta catgatcccc 4440
catgttgtgc aaaaaagcgg ttagctcctt cggtcctccg atcgttgtca gaagtaagtt 4500
ggccgcagtg ttatcactca tggttatggc agcactgcat aattctctta ctgtcatgcc 4560
atccgtaaga tgcttttctg tgactggtga gtactcaacc aagtcattct gagaatagtg 4620
tatgcggcga ccgagttgct cttgcccggc gtcaacacgg gataataccg cgccacatag 4680
cagaacttta aaagtgctca tcattggaaa acgttcttcg gggcgaaaac tctcaaggat 4740
cttaccgctg ttgagatcca gttcgatgta acccactcgt gcacccaact gatcttcagc 4800
atcttttact ttcaccagcg tttctgggtg agcaaaaaca ggaaggcaaa atgccgcaaa 4860
aaagggaata agggcgacac ggaaatgttg aatactcata ctcttccttt ttcaatatta 4920
ttgaagcatt tatcagggtt attgtctcat gagcggatac atatttgaat gtatttagaa 4980
aaataaacaa ataggggttc cgcgcacatt tccccgaaaa gtgccacctg acgtctaaga 5040
aaccattatt atcatgacat taacctataa aaataggcgt atcacgaggc cctttcgtct 5100
tcaagaattc cgatccagac atgataagat acattgatga gtttggacaa accacaacta 5160
gaatgcagtg aaaaaaatgc tttatttgtg aaatttgtga tgctattgct ttatttgtaa 5220
ccattagaag ctgcaataaa caagttaaca acaacaattg cattcatttt atgtttcagg 5280
ttcaggggga ggtgtgggag gtttttttaaa gcaagtaaaa cctctacaaa tgtggtatgg 5340
ctgattatga tctaaagcca gcaaaagtcc catggtctta taaaaatgca tagctttcgg 5400
aggggagcag agaacttgaa agcatcttcc tgttagtctt tcttctcgta gaccttaaat 5460
tcatacttga ttcctttttc ctcctggacc tcagagagga cgcctgggta ttctgggaga 5520
agtttatatt tccccaaatc aatttctggg aaaaacgtgt cactttcaaa ttcctgcatg 5580
atccttgtca caaagagtct gaggtggcct ggttgattca tggcttcctg gtaaacagaa 5640
ctgcctccga ctatccaaac catgtctact ttacttgcca attccggttg ttcaataagt 5700
cttaaggcat catccaaact tttggcaaga aaatgagctc ctcgtggtgg ttctttgagt 5760
tctctactga gaactatatt aattctgtcc tttaaaggtc gattcttctc aggaatggag 5820
aaccaggttt tcctacccat aatcaccaga ttctgtttac cttccactga agaggttgtg 5880
gtcattcttt ggaagtactt gaactcgttc ctgagcggag gccagggtcg gtctccgttc 5940
ttgccaatcc ccatatttg ggacacggcg acgatgcagt tcaatggtcg aaccatgagg 6000
gcaccaagct agctttttgc aaaagcctag gcctccaaaa aagcctcctc actacttctg 6060
gaatagctca gaggccgagg cggcctcggc ctctgcataa ataaaaaaaa ttagtcagcc 6120
atggggcgga gaatgggcgg aactgggcgg agttaggggc gggatgggcg gagttagggg 6180
cgggactatg gttgctgact aattgagatg catgctttgc atacttctgc ctgctgggga 6240
gcctggggac tttccacacc tggttgctga ctaattgaga tgcatgcttt gcatacttct 6300
gcctgctggg gagcctgggg actttccaca ccctaactga cacacattcc aca 6353

<210> SEQ ID NO 19

<211> LENGTH: 1457
<212> TYPE: DNA
<213> ORGANISM: Artificial Sequence
<220> FEATURE:
<223> OTHER INFORMATION: A nucleic acid sequence of huFcg4h-(linker)-
IFN-beta (C17S F50H H131A H140A) starting from the hinge

<400> SEQUENCE: 19

```
gagcccaaat cttctgacaa aactcacaca tgcccaccgt gcccaggtaa gccagcccag      60

gcctcgccct ccagctcaag gcgggacagg tgccctagag tagcctgcat ccagggacag     120

gccccagccg ggtgctgacg catccacctc catctcttcc tcagcacctg agttcctggg     180

gggaccatca gtcttcctgt tcccccaaaa acccaaggac actctcatga tctcccggac     240

ccctgaggtc acgtgcgtgg tggtggacgt gagccaggaa gaccccgagg tccagttcaa     300

ctggtacgtg gatggcgtgg aggtgcataa tgccaagaca aagccgcggg aggagcagtt     360

caacagcacg taccgtgtgg tcagcgtcct caccgtcctg caccaggact ggctgaacgg     420

caaggagtac aagtgcaagg tctccaacaa aggcctcccg tcctccatcg agaaaaccat     480

ctccaaagcc aaaggtggga cccacggggt gcgagggcca catggacaga ggtcagctcg     540

gcccaccctc tgccctggga gtgaccgctg tgccaacctc tgtccctaca gggcagcccc     600

gagagccaca ggtgtacacc ctgcccccat cccaggagga gatgaccaag aaccaggtca     660

gcctgacctg cctggtcaaa ggcttctacc ccagcgacat cgccgtggag tgggagagca     720

atgggcagcc ggagaacaac tacaagacca cgcctcccgt gctggactcc gacggctcct     780

tcttcctcta cagcaagctc accgtggaca agagcaggtg gcagcagggg aacatcttct     840

catgctccgt gatgcatgag gctctgcaca accactacac gcagaagagc ctctccctgt     900

ccccgggtgc agggggcggg ggcagcgggg gcggaggatc cggcgggggc tcgggtatga     960

gctacaactt gcttggattc ctacaaagaa gcagcaattt tcagagtcag aagctcctgt    1020

ggcaattgaa tgggaggctt gaatattgcc tcaaggacag gatgaacttt gacatccctg    1080

aggagattaa gcagctgcag cagcatcaga aggaggacgc cgcattgacc atctatgaga    1140

tgctccagaa catctttgct attttcagac aagattcatc tagcactggc tggaatgaga    1200

ctattgttga gaacctcctg gctaatgtct atcatcagat aaaccatctg aagacagtcc    1260

tggaagaaaa actggagaaa gaagatttca ccaggggaaa actcatgagc agtctgcacc    1320

tgaaaagata ttatgggagg attctggcct acctgaaggc caaggagtac agtgcctgtg    1380

cctggaccat agtcagagtg gaaatcctaa ggaactttta cttcattaac agacttacag    1440

gttacctccg aaactga                                                   1457
```

<210> SEQ ID NO 20
<211> LENGTH: 999
<212> TYPE: DNA
<213> ORGANISM: Macaca fascicularis

<400> SEQUENCE: 20

```
gcctccacca agggcccatc ggtcttcccc ctggcgccct cctccaggag cacctccgag      60

agcacagcgg ccctgggctg cctggtcaag gactacttcc ctgaacccgt gaccgtgtcg     120

tggaactcag gctccctgac cagcggcgtg cacaccttcc cggctgtcct acagtcctca     180

gggctctact ccctcagcag cgtggtgacc gtgccctcca gcagcttggg cacccagacc     240

tacgtctgca acgtaaacca caagcccagc aacaccaagg tggacaagag agttgagata     300

aaaacatgtg gtggtggcag caaacctccc acgtgcccac cgtgcccagc acctgaactc     360

ctgggggggac cgtcagtctt cctcttcccc ccaaaaccca aggacaccct catgatctcc    420
```

```
cggaccccctg aggtcacatg cgtggtggta gacgtgagcc aggaagaccc cgatgtcaag    480

ttcaactggt acgtaaacgg cgcggaggtg catcatgccc agacgaagcc acgggagacg    540

cagtacaaca gcacatatcg tgtggtcagc gtcctcaccg tcacgcacca ggactggctg    600

aacggcaagg agtacacgtg caaggtctcc aacaaagccc tcccggcccc catccagaaa    660

accatctcca aagacaaagg gcagccccga gagcctcagg tgtacaccct gcccccgtcc    720

cgggaggagc tgaccaagaa ccaggtcagc ctgacctgcc tggtcaaagg cttctacccc    780

agcgacatcg tcgtggagtg ggagagcagc gggcagccgg agaacaccta caagaccacg    840

ccgcccgtgc tggactccga cggctcctac ttcctctaca gcaagctcac cgtggacaag    900

agcaggtggc ggcaggggaa cgtcttctca tgctccgtga tgcatgaggc tctgcacaac    960

cactacaccc agaagagcct ctccctgtct ccgggtaaa                            999
```

```
<210> SEQ ID NO 21
<211> LENGTH: 333
<212> TYPE: PRT
<213> ORGANISM: Macaca fascicularis

<400> SEQUENCE: 21

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ser Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Val Cys Asn Val Asn His Lys Pro Ser Asn Thr Lys Val Asp Lys
                85                  90                  95

Arg Val Glu Ile Lys Thr Cys Gly Gly Gly Ser Lys Pro Pro Thr Cys
            100                 105                 110

Pro Pro Cys Pro Ala Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser Gln Glu Asp Pro Asp Val Lys
145                 150                 155                 160

Phe Asn Trp Tyr Val Asn Gly Ala Glu Val His His Ala Gln Thr Lys
                165                 170                 175

Pro Arg Glu Thr Gln Tyr Asn Ser Thr Tyr Arg Val Val Ser Val Leu
            180                 185                 190

Thr Val Thr His Gln Asp Trp Leu Asn Gly Lys Glu Tyr Thr Cys Lys
        195                 200                 205

Val Ser Asn Lys Ala Leu Pro Ala Pro Ile Gln Lys Thr Ile Ser Lys
    210                 215                 220

Asp Lys Gly Gln Pro Arg Glu Pro Gln Val Tyr Thr Leu Pro Pro Ser
225                 230                 235                 240

Arg Glu Glu Leu Thr Lys Asn Gln Val Ser Leu Thr Cys Leu Val Lys
                245                 250                 255

Gly Phe Tyr Pro Ser Asp Ile Val Val Glu Trp Glu Ser Ser Gly Gln
            260                 265                 270
```

-continued

```
Pro Glu Asn Thr Tyr Lys Thr Thr Pro Pro Val Leu Asp Ser Asp Gly
        275                 280                 285

Ser Tyr Phe Leu Tyr Ser Lys Leu Thr Val Asp Lys Ser Arg Trp Arg
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330


<210> SEQ ID NO 22
<211> LENGTH: 999
<212> TYPE: DNA
<213> ORGANISM: Macaca mulatta

<400> SEQUENCE: 22

gcctccacca agggcccatc ggtcttcccc ctggcgccct cctccaggag cacctccgag      60

agcacagcgg ccctgggctg cctggtcaag gactacttcc ctgaacccgt gaccgtgtcg     120

tggaactcag gctccctgac cagcggcgtg cacaccttcc cggctgtcct acagtcctca     180

gggctctact ccctcagcag cgtggtgacc gtgccctcca gcagcttggg cacccagacc     240

tacgtctgca acgtaaacca caagcccagc aacaccaagg tggacaagag agttgagata     300

aaaacatgtg gtggtggcag caaacctccc acgtgcccac cgtgcaccag ccctgaactc     360

ctgggggggac cgtcagtctt cctcttcccc ccaaaaccca aggacaccct catgatctcc     420

cggacccctg aggtcacatg cgtggtggta gacgtgagcc aggaagaccc cgatgtcaag     480

ttcaactggt acgtaaacgg cgcggaggtg catcatgccc agacgaagcc acgggagacg     540

cagtacaaca gcacatatcg tgtggtcagc gtcctcaccg tcacgcacca ggactggctg     600

aacggcaagg agtacacgtg caaggtctcc aacaaagccc tcccggcccc catccagaaa     660

accatctcca aagacaaagg gcagccccga gagcctcagg tgtacaccct gccccccgtcc     720

cgggaggagc tgaccaagaa ccaggtcagc ctgacctgcc tggtcaaagg cttctacccc     780

agcgacatcg tcgtggagtg ggagagcagc gggcagccgg agaacaccta caagaccacc     840

ccgcccgtgc tggactccga cggctcctac ttcctctaca gcaagctcac cgtggacaag     900

agcaggtggc agcaggggaa cgtcttctca tgctccgtga tgcatgaggc tctgcacaac     960

cactacaccc agaagagcct ctccctgtct ccgggtaaa                           999


<210> SEQ ID NO 23
<211> LENGTH: 333
<212> TYPE: PRT
<213> ORGANISM: Macaca mulatta

<400> SEQUENCE: 23

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ser Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Val Cys Asn Val Asn His Lys Pro Ser Asn Thr Lys Val Asp Lys
                85                  90                  95
```

```
Arg Val Glu Ile Lys Thr Cys Gly Gly Gly Ser Lys Pro Pro Thr Cys
            100                 105                 110

Pro Pro Cys Thr Ser Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser Gln Glu Asp Pro Asp Val Lys
145                 150                 155                 160

Phe Asn Trp Tyr Val Asn Gly Ala Glu Val His His Ala Gln Thr Lys
                165                 170                 175

Pro Arg Glu Thr Gln Tyr Asn Ser Thr Tyr Arg Val Val Ser Val Leu
            180                 185                 190

Thr Val Thr His Gln Asp Trp Leu Asn Gly Lys Glu Tyr Thr Cys Lys
        195                 200                 205

Val Ser Asn Lys Ala Leu Pro Ala Pro Ile Gln Lys Thr Ile Ser Lys
    210                 215                 220

Asp Lys Gly Gln Pro Arg Glu Pro Gln Val Tyr Thr Leu Pro Pro Ser
225                 230                 235                 240

Arg Glu Glu Leu Thr Lys Asn Gln Val Ser Leu Thr Cys Leu Val Lys
                245                 250                 255

Gly Phe Tyr Pro Ser Asp Ile Val Val Glu Trp Glu Ser Ser Gly Gln
            260                 265                 270

Pro Glu Asn Thr Tyr Lys Thr Thr Pro Pro Val Leu Asp Ser Asp Gly
        275                 280                 285

Ser Tyr Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330


<210> SEQ ID NO 24
<211> LENGTH: 1133
<212> TYPE: DNA
<213> ORGANISM: Felis catus

<400> SEQUENCE: 24

gcctccacca cggccccatc ggtgttccca ctggccccca gctgcgggac cacatctggc      60

gccaccgtgg ccctggcctg cctggtgtta ggctacttcc ctgagccggt gaccgtgtcc     120

tggaactccg gcgccctgac cagcggtgtg cacaccttcc cggccgtcct gcaggcctcg     180

gggctgtact ctctcagcag catggtgaca gtgccctcca gcaggtggct cagtgacacc     240

ttcacctgca acgtggccca cccgcccagc aacaccaagg tggacaagac cgtgcgcaaa     300

acagaccacc caccgggacc caaaccctgc gactgtccca aatgcccacc ccctgagatg     360

cttggaggac cgtccatctt catcttcccc ccaaaaccca aggacaccct ctcgatttcc     420

cggacgcccg aggtcacatg cttggtggtg gacttgggcc cagatgactc cgatgtccag     480

atcacatggt ttgtggataa cacccaggtg tacacagcca agacgagtcc gcgtgaggag     540

cagttcaaca gcacctaccg tgtggtcagt gtcctcccca tcctacacca ggactggctc     600

aaggggaagg agttcaagtg caaggtcaac agcaaatccc tcccctcccc catcgagagg     660

accatctcca aggccaaagg acagccccac gagccccagg tgtacgtcct gcctccagcc     720

caggaggagc tcagcaggaa caaagtcagt gtgacctgcc tgatcaaaag cttccacccg     780

cctgacattg ccgtcgagtg ggagatcacc ggacagccgg agccagagaa caactaccgg     840
```

-continued

```
acgaccccgc cccagctgga cagcgacggg acctacttcg tgtacagcaa gctctcggtg    900

gacaggtccc actggcagag gggaaacacc tacacctgct cggtgtcaca cgaagctctg    960

cacagccacc acacacagaa atccctcacc cagtctccgg gtaaatgagc agcgcgccca   1020

gccccccagg aggcccccgc gggctctgag cgcccacccc tgtgtacatc ccccaccccg   1080

ggcaggtacc ctgcgtgaaa taaagcaccc agcactgccc tgggacctag gac          1133


<210> SEQ ID NO 25
<211> LENGTH: 335
<212> TYPE: PRT
<213> ORGANISM: Felis catus

<400> SEQUENCE: 25

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
        115                 120                 125

Phe Pro Pro Lys Pro Lys Asp Thr Leu Ser Ile Ser Arg Thr Pro Glu
    130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
        195                 200                 205

Val Asn Ser Lys Ser Leu Pro Ser Pro Ile Glu Arg Thr Ile Ser Lys
    210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
        275                 280                 285

Asp Gly Thr Tyr Phe Val Tyr Ser Lys Leu Ser Val Asp Arg Ser His
    290                 295                 300

Trp Gln Arg Gly Asn Thr Tyr Thr Cys Ser Val Ser His Glu Ala Leu
305                 310                 315                 320

His Ser His His Thr Gln Lys Ser Leu Thr Gln Ser Pro Gly Lys
```

-continued 325 330 335

<210> SEQ ID NO 26
<211> LENGTH: 1235
<212> TYPE: DNA
<213> ORGANISM: Oryctolagus cuniculus

<400> SEQUENCE: 26
atgagctggg tccgacaggc tccagggaag gagctggagt ggatcggata cattagttat 60
ggtggtagtg catactacgc gagctgggcg aaaagccgat ccaccatcac cagaaacacc 120
aacgagaaca cggtgactct gaaaatgacc agtctgacag ccgcggacac ggccacctat 180
ttctgtgcga gacattgggg catctggggc ccaggcaccc tggtcaccgt ctcctcaggg 240
caacctaagg ctccatcagt cttcccactg gccccctgct gcggggacac acccagctcc 300
acggtgaccc tgggctgcct ggtcaaaggc tacctcccgg agccagtgac cgtgacctgg 360
aactcgggca ccctcaccaa tggggtacgc accttcccgt ccgtccggca gtcctcaggc 420
ctctactcgc tgagcagcgt ggtgagcgtg acctcaagca gccagcccgt cacctgcaac 480
gtggcccacc cagccaccaa caccaaagtg gacaagaccg ttgcaccctc gacatgcagc 540
aagcccacgt gcccaccccc tgaactcctg gggggaccgt ctgtcttcat cttcccccca 600
aaacccaagg acaccctcat gatctcacgc acccccgagg tcacatgcgt ggtggtggac 660
gtgagccagg atgaccccga ggtgcagttc acatggtaca taaacaacga gcaggtgcgc 720
accgcccggc cgccgctacg ggagcagcag ttcaacagca cgatccgcgt ggtcagcacc 780
ctccccatca cgcaccagga ctggctgagg ggcaaggagt tcaagtgcaa agtccacaac 840
aaggcactcc cggcccccat cgagaaaacc atctccaaag ccagagggca gcccctggag 900
ccgaaggtct acaccatggg ccctccccgg gaggagctga gcagcaggtc ggtcagcctg 960
acctgcatga tcaacggctt ctacccttcc gacatctcgg tggagtggga gaagaacggg 1020
aaggcagagg acaactacaa gaccacgccg gccgtgctgg acagcgacgg ctcctacttc 1080
ctctacaaca agctctcagt gcccacgagt gagtggcagc ggggcgacgt cttcacctgc 1140
tccgtgatgc acgaggcctt gcacaaccac tacacgcaga agtccatctc ccgctctccg 1200
ggtaaatgag cgctgtgccg gcgagctgcc cctct 1235

<210> SEQ ID NO 27
<211> LENGTH: 402
<212> TYPE: PRT
<213> ORGANISM: Oryctolagus cuniculus

<400> SEQUENCE: 27

Met Ser Trp Val Arg Gln Ala Pro Gly Lys Glu Leu Glu Trp Ile Gly
1 5 10 15

Tyr Ile Ser Tyr Gly Gly Ser Ala Tyr Tyr Ala Ser Trp Ala Lys Ser
20 25 30

Arg Ser Thr Ile Thr Arg Asn Thr Asn Glu Asn Thr Val Thr Leu Lys
35 40 45

Met Thr Ser Leu Thr Ala Ala Asp Thr Ala Thr Tyr Phe Cys Ala Arg
50 55 60

His Trp Gly Ile Trp Gly Pro Gly Thr Leu Val Thr Val Ser Ser Gly
65 70 75 80

Gln Pro Lys Ala Pro Ser Val Phe Pro Leu Ala Pro Cys Cys Gly Asp
85 90 95

Thr Pro Ser Ser Thr Val Thr Leu Gly Cys Leu Val Lys Gly Tyr Leu
100 105 110

-continued

```
Pro Glu Pro Val Thr Val Thr Trp Asn Ser Gly Thr Leu Thr Asn Gly
        115                 120                 125

Val Arg Thr Phe Pro Ser Val Arg Gln Ser Ser Gly Leu Tyr Ser Leu
    130                 135                 140

Ser Ser Val Val Ser Val Thr Ser Ser Ser Gln Pro Val Thr Cys Asn
145                 150                 155                 160

Val Ala His Pro Ala Thr Asn Thr Lys Val Asp Lys Thr Val Ala Pro
                165                 170                 175

Ser Thr Cys Ser Lys Pro Thr Cys Pro Pro Pro Glu Leu Leu Gly Gly
            180                 185                 190

Pro Ser Val Phe Ile Phe Pro Pro Lys Pro Lys Asp Thr Leu Met Ile
        195                 200                 205

Ser Arg Thr Pro Glu Val Thr Cys Val Val Val Asp Val Ser Gln Asp
    210                 215                 220

Asp Pro Glu Val Gln Phe Thr Trp Tyr Ile Asn Asn Glu Gln Val Arg
225                 230                 235                 240

Thr Ala Arg Pro Pro Leu Arg Glu Gln Gln Phe Asn Ser Thr Ile Arg
                245                 250                 255

Val Val Ser Thr Leu Pro Ile Thr His Gln Asp Trp Leu Arg Gly Lys
            260                 265                 270

Glu Phe Lys Cys Lys Val His Asn Lys Ala Leu Pro Ala Pro Ile Glu
        275                 280                 285

Lys Thr Ile Ser Lys Ala Arg Gly Gln Pro Leu Glu Pro Lys Val Tyr
    290                 295                 300

Thr Met Gly Pro Pro Arg Glu Glu Leu Ser Ser Arg Ser Val Ser Leu
305                 310                 315                 320

Thr Cys Met Ile Asn Gly Phe Tyr Pro Ser Asp Ile Ser Val Glu Trp
                325                 330                 335

Glu Lys Asn Gly Lys Ala Glu Asp Asn Tyr Lys Thr Thr Pro Ala Val
            340                 345                 350

Leu Asp Ser Asp Gly Ser Tyr Phe Leu Tyr Asn Lys Leu Ser Val Pro
        355                 360                 365

Thr Ser Glu Trp Gln Arg Gly Asp Val Phe Thr Cys Ser Val Met His
    370                 375                 380

Glu Ala Leu His Asn His Tyr Thr Gln Lys Ser Ile Ser Arg Ser Pro
385                 390                 395                 400

Gly Lys
```

```
<210> SEQ ID NO 28
<211> LENGTH: 1079
<212> TYPE: DNA
<213> ORGANISM: Sus scrofa

<400> SEQUENCE: 28

gcccccaaga cggccccatt ggtctaccct ctggcccccct gcggcaggga cacgtctggc      60

cctaacgtgg ccttgggctg cctggcctca agctacttcc ccgagccagt gaccgtgacc     120

tggaactcgg gcgccctgac cagtggcgtg catacettcc catccgtcct gcagccgtca     180

gggctctact ccctcagcag catggtgacc gtgccggcca gcagcctgtc cagcaagagc     240

tacacctgca atgtcaacca cccggccacc accaccaagg tggacaagcg tgttggaaca     300

aagaccaaac caccatgtcc catatgccca gcctgtgaat cgccagggcc ctcggtcttc     360

atcttccctc caaaacccaa ggacaccctc atgatctccc ggacacccca ggtcacgtgc     420

gtggtagttg atgtgagcca ggagaacccg gaggtccagt tctcctggta cgtggacggc     480
```

-continued

```
gtagaggtgc acacggccca gacgaggcca aaggaggagc agttcaacag cacctaccgc     540

gtggtcagcg tcctgcccat ccagcaccag gactggctga acgggaagga gttcaagtgc     600

aaggtcaaca acaaagacct cccagccccc atcacaagga tcatctccaa ggccaaaggg     660

cagacccggg agccgcaggt gtacaccctg cccccacacg ccgaggagct gtccaggagc     720

aaagtcagca taacctgcct ggtcattggc ttctacccac ctgacatcga tgtcgagtgg     780

caaagaaacg gacagccgga gccagagggc aattaccgca ccaccccgcc ccagcaggac     840

gtggacggga cctacttcct gtacagcaag ttctcggtgg acaaggccag ctggcagggt     900

ggaggcatat tccagtgtgc ggtgatgcac gaggctctgc acaaccacta cacccagaag     960

tctatctcca agactccggg taaatgagcc actcgctgca cccctcatgc tcttgggtcc    1020

caagagctca cctgagcccc agcgctgtgt acatacgtcc cgggccagca tgaaataaa     1079


<210> SEQ ID NO 29
<211> LENGTH: 328
<212> TYPE: PRT
<213> ORGANISM: Sus scrofa

<400> SEQUENCE: 29

Ala Pro Lys Thr Ala Pro Leu Val Tyr Pro Leu Ala Pro Cys Gly Arg
1               5                   10                  15

Asp Thr Ser Gly Pro Asn Val Ala Leu Gly Cys Leu Ala Ser Ser Tyr
            20                  25                  30

Phe Pro Glu Pro Val Thr Val Thr Trp Asn Ser Gly Ala Leu Thr Ser
        35                  40                  45

Gly Val His Thr Phe Pro Ser Val Leu Gln Pro Ser Gly Leu Tyr Ser
    50                  55                  60

Leu Ser Ser Met Val Thr Val Pro Ala Ser Ser Leu Ser Ser Lys Ser
65                  70                  75                  80

Tyr Thr Cys Asn Val Asn His Pro Ala Thr Thr Thr Lys Val Asp Lys
                85                  90                  95

Arg Val Gly Thr Lys Thr Lys Pro Pro Cys Pro Ile Cys Pro Ala Cys
            100                 105                 110

Glu Ser Pro Gly Pro Ser Val Phe Ile Phe Pro Pro Lys Pro Lys Asp
        115                 120                 125

Thr Leu Met Ile Ser Arg Thr Pro Gln Val Thr Cys Val Val Val Asp
    130                 135                 140

Val Ser Gln Glu Asn Pro Glu Val Gln Phe Ser Trp Tyr Val Asp Gly
145                 150                 155                 160

Val Glu Val His Thr Ala Gln Thr Arg Pro Lys Glu Glu Gln Phe Asn
                165                 170                 175

Ser Thr Tyr Arg Val Val Ser Val Leu Pro Ile Gln His Gln Asp Trp
            180                 185                 190

Leu Asn Gly Lys Glu Phe Lys Cys Lys Val Asn Asn Lys Asp Leu Pro
        195                 200                 205

Ala Pro Ile Thr Arg Ile Ile Ser Lys Ala Lys Gly Gln Thr Arg Glu
    210                 215                 220

Pro Gln Val Tyr Thr Leu Pro Pro His Ala Glu Glu Leu Ser Arg Ser
225                 230                 235                 240

Lys Val Ser Ile Thr Cys Leu Val Ile Gly Phe Tyr Pro Pro Asp Ile
                245                 250                 255

Asp Val Glu Trp Gln Arg Asn Gly Gln Pro Glu Pro Glu Gly Asn Tyr
            260                 265                 270
```

-continued

```
Arg Thr Thr Pro Pro Gln Gln Asp Val Asp Gly Thr Tyr Phe Leu Tyr
        275                 280                 285

Ser Lys Phe Ser Val Asp Lys Ala Ser Trp Gln Gly Gly Gly Ile Phe
    290                 295                 300

Gln Cys Ala Val Met His Glu Ala Leu His Asn His Tyr Thr Gln Lys
305                 310                 315                 320

Ser Ile Ser Lys Thr Pro Gly Lys
                325


<210> SEQ ID NO 30
<211> LENGTH: 870
<212> TYPE: DNA
<213> ORGANISM: Camelus dromedarius

<400> SEQUENCE: 30

ggatccaggt caccgtctcc tcaggaacga atgaagtatg caagtgtccc aaatgtccag     60

cccctgagct cccgggaggc ccctccgtct tcgtcttccc cccgaaaccc aaggacgtcc    120

tctccatttc tgggaggccc gaggtcacgt gcgttgtggt ggacgtgggt aaggaagacc    180

ccgaggtcaa tttcaactgg tacattgatg gcgttgaggt gcgaacggcc aacacgaagc    240

caaaggagga acagttcaac agcacgtacc gcgtggtcag cgtcctgacc atccagcacc    300

aggactggct gacggggaag gagttcaagt gcaaggtcaa caacaaagct ctcccggccc    360

ccatcgagag gaccatctcc aagcccaaag gacagacccg ggagccgcag gtgtacaccc    420

tggccccaca ccgggaagag ttggccaagg acaccgtgag cgtaacctgc ctggtcaaag    480

gcttctaccc acctgacatc aacgttgagt ggcagaggaa ccgacagcca gagtcagagg    540

gcgcctacgc caccacgctg ccccagctgg acaacgacgg gacctacttc ctctacagca    600

agctctcggt gggaaagaac acgtggcagc ggggagaaac cttcacctgt gtggtgatgc    660

acgaggccct gcacaaccac tacacccaga aatccatcac ccagtcttcg ggtaaatgag    720

cctcaccccg gcaccccagc gaacacccct ccccgaggcc ctcagggtcc agcacggatg    780

cctgagcccc accccctgtgt acatacctcc cgggccagca tgaaataaaa cacccagtgc    840

ctccctgggg cccttcaaaa aaaaaaaaaa                                     870


<210> SEQ ID NO 31
<211> LENGTH: 1581
<212> TYPE: DNA
<213> ORGANISM: Bos taurus

<400> SEQUENCE: 31

ctgactctca tctgctccaa gatgaaccca ctgtggaccc tcctctttgt gctgtcagcc     60

cccatagggg tcctgtccca ggtgcagctg cgggagtcgg gccccagcct ggtgaagccc    120

tcacagaccc tctccctcac gtgcacggtg tctggattct cattgagcag ctatgctcta    180

acctgggtcc gccaggctcc agggaaggcg ctggagtggg ttggtggtat aaccagtggt    240

ggaaccacat actataatcc agccctgaaa tcccggctca gcatcaccaa ggagaactcc    300

aagagccaag tctctctgtc agtgagcagc gtgacacctg aggacacagc cacatactac    360

tgtgcaagaa gtacttatgg tgaggttggt gatggtgcca tcgccgatgc ctggggccaa    420

ggactcctgg tcaccgtctc ctcagcctcc accacagccc cgaaagtcta ccctctgagt    480

tcttgctgcg gggacaagtc cagctccacc gtgaccctgg gctgcctggt ctccagctac    540

atgcccgagc cggtgaccgt gacctggaac tcgggtgccc tgaagagcgg cgtgcacacc    600

ttcccggctg tccttcagtc ctccgggctg tactctctca gcagcatggt gaccgtgccc    660
```

-continued

```
ggcagcacct caggacagac cttcacctgc aacgtagccc acccggccag cagcaccaag    720

gtggacaagg ctgttgatcc cacatgcaaa ccatcaccct gtgactgttg cccacccccct    780

gagctccccg gaggaccctc tgtcttcatc ttcccaccga aacccaagga caccctcaca    840

atctcgggaa cgcccgaggt cacgtgtgtg gtggtggacg tgggccacga tgaccccgag    900

gtgaagttct cctggttcgt ggacgacgtg gaggtaaaca cagccacgac gaagccgaga    960

gaggagcagt tcaacagcac ctaccgcgtg gtcagcgccc tgcgcatcca gcaccaggac   1020

tggactggag gaaaggagtt caagtgcaag gtccacaacg aaggcctccc ggcccccatc   1080

gtgaggacca tctccaggac caaagggccg gcccgggagc cgcaggtgta tgtcctggcc   1140

ccaccccagg aagagctcag caaaagcacg gtcagcctca cctgcatggt caccagcttc   1200

tacccagact acatcgccgt ggagtggcag agaaacgggc agcctgagtc ggaggacaag   1260

tacggcacga ccccgcccca gctggacgcc gacagctcct acttcctgta cagcaagctc   1320

agggtggaca ggaacagctg gcaggaagga gacacctaca cgtgtgtggt gatgcacgag   1380

gccctgcaca atcactacac gcagaagtcc acctctaagt ctgcgggtaa atgagcctca   1440

cgtccctgca ccagcaagcc ctcacccagc ccaccctccc cgggctccag gtccagccag   1500

gacgccctag cccctccctg tgtgcattcc tcctgggccg ccgtgaataa agcacccagg   1560

ccgccctggg accctgcaaa a                                             1581
```

<210> SEQ ID NO 32
<211> LENGTH: 470
<212> TYPE: PRT
<213> ORGANISM: Bos taurus

<400> SEQUENCE: 32

```
Met Asn Pro Leu Trp Thr Leu Leu Phe Val Leu Ser Ala Pro Ile Gly
1               5                   10                  15

Val Leu Ser Gln Val Gln Leu Arg Glu Ser Gly Pro Ser Leu Val Lys
            20                  25                  30

Pro Ser Gln Thr Leu Ser Leu Thr Cys Thr Val Ser Gly Phe Ser Leu
        35                  40                  45

Ser Ser Tyr Ala Leu Thr Trp Val Arg Gln Ala Pro Gly Lys Ala Leu
    50                  55                  60

Glu Trp Val Gly Gly Ile Thr Ser Gly Gly Thr Thr Tyr Tyr Asn Pro
65                  70                  75                  80

Ala Leu Lys Ser Arg Leu Ser Ile Thr Lys Glu Asn Ser Lys Ser Gln
                85                  90                  95

Val Ser Leu Ser Val Ser Ser Val Thr Pro Glu Asp Thr Ala Thr Tyr
            100                 105                 110

Tyr Cys Ala Arg Ser Thr Tyr Gly Glu Val Gly Asp Gly Ala Ile Ala
        115                 120                 125

Asp Ala Trp Gly Gln Gly Leu Leu Val Thr Val Ser Ser Ala Ser Thr
    130                 135                 140

Thr Ala Pro Lys Val Tyr Pro Leu Ser Ser Cys Cys Gly Asp Lys Ser
145                 150                 155                 160

Ser Ser Thr Val Thr Leu Gly Cys Leu Val Ser Ser Tyr Met Pro Glu
                165                 170                 175

Pro Val Thr Val Thr Trp Asn Ser Gly Ala Leu Lys Ser Gly Val His
            180                 185                 190

Thr Phe Pro Ala Val Leu Gln Ser Ser Gly Leu Tyr Ser Leu Ser Ser
        195                 200                 205

Met Val Thr Val Pro Gly Ser Thr Ser Gly Gln Thr Phe Thr Cys Asn
```

```
    210                 215                 220

Val Ala His Pro Ala Ser Ser Thr Lys Val Asp Lys Ala Val Asp Pro
225                 230                 235                 240

Thr Cys Lys Pro Ser Pro Cys Asp Cys Cys Pro Pro Pro Glu Leu Pro
                245                 250                 255

Gly Gly Pro Ser Val Phe Ile Phe Pro Pro Lys Pro Lys Asp Thr Leu
            260                 265                 270

Thr Ile Ser Gly Thr Pro Glu Val Thr Cys Val Val Val Asp Val Gly
        275                 280                 285

His Asp Asp Pro Glu Val Lys Phe Ser Trp Phe Val Asp Asp Val Glu
    290                 295                 300

Val Asn Thr Ala Thr Thr Lys Pro Arg Glu Glu Gln Phe Asn Ser Thr
305                 310                 315                 320

Tyr Arg Val Val Ser Ala Leu Arg Ile Gln His Gln Asp Trp Thr Gly
                325                 330                 335

Gly Lys Glu Phe Lys Cys Lys Val His Asn Glu Gly Leu Pro Ala Pro
            340                 345                 350

Ile Val Arg Thr Ile Ser Arg Thr Lys Gly Pro Ala Arg Glu Pro Gln
        355                 360                 365

Val Tyr Val Leu Ala Pro Pro Gln Glu Glu Leu Ser Lys Ser Thr Val
    370                 375                 380

Ser Leu Thr Cys Met Val Thr Ser Phe Tyr Pro Asp Tyr Ile Ala Val
385                 390                 395                 400

Glu Trp Gln Arg Asn Gly Gln Pro Glu Ser Glu Asp Lys Tyr Gly Thr
                405                 410                 415

Thr Pro Pro Gln Leu Asp Ala Asp Ser Ser Tyr Phe Leu Tyr Ser Lys
            420                 425                 430

Leu Arg Val Asp Arg Asn Ser Trp Gln Glu Gly Asp Thr Tyr Thr Cys
        435                 440                 445

Val Val Met His Glu Ala Leu His Asn His Tyr Thr Gln Lys Ser Thr
    450                 455                 460

Ser Lys Ser Ala Gly Lys
465                 470


<210> SEQ ID NO 33
<211> LENGTH: 1547
<212> TYPE: DNA
<213> ORGANISM: Mustela vison

<400> SEQUENCE: 33

cacgagctct tttaaaaggt gtccagtgtg aggtgcagct ggtggagtct gggggagacc     60

gggtgaagcc tggggggtcc ctgagacttt cctgtgcagc ctctggattc accttcagta    120

actacggcat gagctgggtc cgccaagctc caaggaaggg gctgcagtgg gtcgcatgga    180

tgagttatga tgggagttac acaaactacg cagactctgt gaagggccga ttcaccatct    240

ccagagacaa tggcgagaac acgctgtatc tgcagacgat cagcctgaga gccgaggaca    300

cggccctata ttactgtaca acctctacgt ttcttgtgtc agatccgcct gcttcatcct    360

acggtctgga ctactggggc caggggacct cggtcaccgt gtcctcagct tccaccacgg    420

ccccatcggt tttcccactg gcccccagct gcggggccac ccccggaccc acagtggccc    480

tggcctgcct ggtgtccggc tacttccctg agcctgtcac tgtgtcctgg aactccggct    540

ccttgaccag cggtgtgcac accttcccgt ccgtcctgca gtcctcgggg ctctactctc    600

tcagcagcat ggtgaccgtg ccctccagca ggtggcccag cgacaccttc atctgcaccg    660
```

-continued

```
tggcccaccc agccagtaac accagggtgg acaagagagt gcccccagga aaaattcctc    720

cgccatgcac atgtccccca cgtgcagaat gtgatatgct cggaggacct tcagtcttca    780

tgttcccccc gaaacccagg gacaccctct ccatttcccg aacccccgag gtcacatgca    840

tggtggtgga cctggaagac cctgaggtcc agatcagctg gttcgtggac aaccaggaga    900

tgcacacggc caagacgaat tcacgagagc agcagttcaa cagcaccttc cgtgtggtca    960

gtgtcctccc catccagcac caggactggc tcaaggggaa ggtcttcaag tgcaaggtca   1020

acaacaaagc tctcccatcc cccattgaga ggaccatctc caaggtcaaa ggggaagccc   1080

atcagcccag tgtgtatgtc ctgcccccat cccgggacga gctgagcaag aacagggtca   1140

gtgtgacctg catggtcaaa gacttctacc cacctgacat tgatgtggag tggcagagca   1200

acggccaaca gtttccagag gccagtgtgc gaacaacccc gccccagctg gatgcggacg   1260

gcacctactt cctctacagc aagctctcgg tggacaaggc gcgctggcag gggggagaaa   1320

ccttcacgtg tgcggtgctg catgaagccc tacacaacca ccacacgcag aagaccatct   1380

cccagtctcc gggtaaatga gccgcacgcc cggccccccc gcgagccccc acccacaggc   1440

tcttggggtc ccccgaggac gccggagccc ccacccctgt gtacgtacct cccgggcagg   1500

cgcccctgcg tgaaataaag cacccagcac tgccctggga cccagcg                 1547
```

<210> SEQ ID NO 34
<211> LENGTH: 465
<212> TYPE: PRT
<213> ORGANISM: Mustela vison

<400> SEQUENCE: 34

```
Arg Ala Leu Leu Lys Gly Val Gln Cys Glu Val Gln Leu Val Glu Ser
1               5                   10                  15

Gly Gly Asp Arg Val Lys Pro Gly Gly Ser Leu Arg Leu Ser Cys Ala
            20                  25                  30

Ala Ser Gly Phe Thr Phe Ser Asn Tyr Gly Met Ser Trp Val Arg Gln
        35                  40                  45

Ala Pro Arg Lys Gly Leu Gln Trp Val Ala Trp Met Ser Tyr Asp Gly
    50                  55                  60

Ser Tyr Thr Asn Tyr Ala Asp Ser Val Lys Gly Arg Phe Thr Ile Ser
65                  70                  75                  80

Arg Asp Asn Gly Glu Asn Thr Leu Tyr Leu Gln Thr Ile Ser Leu Arg
                85                  90                  95

Ala Glu Asp Thr Ala Leu Tyr Tyr Cys Thr Thr Ser Thr Phe Leu Val
            100                 105                 110

Ser Asp Pro Pro Ala Ser Ser Tyr Gly Leu Asp Tyr Trp Gly Gln Gly
        115                 120                 125

Thr Ser Val Thr Val Ser Ser Ala Ser Thr Thr Ala Pro Ser Val Phe
    130                 135                 140

Pro Leu Ala Pro Ser Cys Gly Ala Thr Pro Gly Pro Thr Val Ala Leu
145                 150                 155                 160

Ala Cys Leu Val Ser Gly Tyr Phe Pro Glu Pro Val Thr Val Ser Trp
                165                 170                 175

Asn Ser Gly Ser Leu Thr Ser Gly Val His Thr Phe Pro Ser Val Leu
            180                 185                 190

Gln Ser Ser Gly Leu Tyr Ser Leu Ser Ser Met Val Thr Val Pro Ser
        195                 200                 205

Ser Arg Trp Pro Ser Asp Thr Phe Ile Cys Thr Val Ala His Pro Ala
    210                 215                 220
```

```
Ser Asn Thr Arg Val Asp Lys Arg Val Pro Pro Gly Lys Ile Pro Pro
225                 230                 235                 240

Pro Cys Thr Cys Pro Pro Arg Ala Glu Cys Asp Met Leu Gly Gly Pro
                245                 250                 255

Ser Val Phe Met Phe Pro Pro Lys Pro Arg Asp Thr Leu Ser Ile Ser
            260                 265                 270

Arg Thr Pro Glu Val Thr Cys Met Val Val Asp Leu Glu Asp Pro Glu
        275                 280                 285

Val Gln Ile Ser Trp Phe Val Asp Asn Gln Glu Met His Thr Ala Lys
    290                 295                 300

Thr Asn Ser Arg Glu Gln Gln Phe Asn Ser Thr Phe Arg Val Val Ser
305                 310                 315                 320

Val Leu Pro Ile Gln His Gln Asp Trp Leu Lys Gly Lys Val Phe Lys
                325                 330                 335

Cys Lys Val Asn Asn Lys Ala Leu Pro Ser Pro Ile Glu Arg Thr Ile
            340                 345                 350

Ser Lys Val Lys Gly Glu Ala His Gln Pro Ser Val Tyr Val Leu Pro
        355                 360                 365

Pro Ser Arg Asp Glu Leu Ser Lys Asn Arg Val Ser Val Thr Cys Met
    370                 375                 380

Val Lys Asp Phe Tyr Pro Pro Asp Ile Asp Val Glu Trp Gln Ser Asn
385                 390                 395                 400

Gly Gln Gln Phe Pro Glu Ala Ser Val Arg Thr Thr Pro Pro Gln Leu
                405                 410                 415

Asp Ala Asp Gly Thr Tyr Phe Leu Tyr Ser Lys Leu Ser Val Asp Lys
            420                 425                 430

Ala Arg Trp Gln Gly Gly Glu Thr Phe Thr Cys Ala Val Leu His Glu
        435                 440                 445

Ala Leu His Asn His His Thr Gln Lys Thr Ile Ser Gln Ser Pro Gly
    450                 455                 460

Lys
465
```

<210> SEQ ID NO 35
<211> LENGTH: 1594
<212> TYPE: DNA
<213> ORGANISM: Ovis aries

<400> SEQUENCE: 35

```
gaacccactg tggaccctcc tctttgtact ctcagccccc agaggggtcc tgtcccaggt     60

gcggctgcag gagtcgggac ccagcctggc gacgctgcta cagaccctct ccgtcacctg    120

cacgatctct ggattctcat taaataatta tggtgtagac tgggtccgcc aggctccagg    180

aaaggcgctg gagtggcttg gtggcagcgg ttatgatgaa gatatagact acaatccagt    240

ccttaagtcc cggctcagca tcaccaagga cacctccaag agtcaagtgt cgttgacact    300

gagcaccgtg acgactgagg acacggccgt gtactactgc gcaagagttg attatgatag    360

tagtcatgct tttgcgtatg cctcatacga cttctggggc ccagggctcc tgatcagcgt    420

tctttcagcc tcaacaacac ccccgaaagt ctaccctctg acttcttgct gcggggacac    480

gtccagctcc atcgtgaccc tgggctgcct ggtctccagc tatatgcccg agccggtgac    540

cgtgacctgg aactctggtg ccctgaccag cggcgtgcac accttcccgg ccatcctgca    600

gtcctccggg ctctactctc tcagcagcgt ggtgaccgtg ccggccagca cctcaggagc    660

ccagaccttc atctgcaacg tagcccaccc ggccagcagc accaaggtgg acaagcgtgt    720
```

-continued

```
tgagcccgga tgcccggacc catgcaaaca ttgccgatgc ccaccccctg agctccccgg    780

aggaccgtct gtcttcatct tcccaccgaa acccaaggac acccttacaa tctctggaac    840

gcccgaggtc acgtgtgtgg tggtggacgt gggccaggat gaccccgagg tgcagttctc    900

ctggttcgtg gacaacgtgg aggtgcgcac ggccaggaca aagccgagag aggagcagtt    960

caacagcacc ttccgcgtgg tcagcgccct gcccatccag caccaagact ggactggagg   1020

aaaggagttc aagtgcaagg tccacaacga agccctcccg gcccccatcg tgaggaccat   1080

ctccaggacc aaagggcagg cccgggagcc gcaggtgtac gtcctggccc caccccagga   1140

agagctcagc aaaagcacgc tcagcgtcac ctgcctggtc accggcttct acccagacta   1200

catcgccgtg gagtggcaga aaaatgggca gcctgagtcg gaggacaagt acggcacgac   1260

cacatcccag ctggacgccg acggctccta cttcctgtac agcaggctca gggtggacaa   1320

gaacagctgg caagaaggag acacctacgc gtgtgtggtg atgcacgagg ctctgcacaa   1380

ccactacaca cagaagtcga tctctaagcc tccgggtaaa tgagccagat gcccccgcac   1440

cagcaagccc tcacccagcc cgccctcccc gggctccagg tccagccagg acgccctagc   1500

ccctccctgt gtgcatgcct cctgggccgg ccatgaataa agcaccaggc cgccctggga   1560

ccctgcaaaa aaaaaaaaaa aaaaaaaaaa aaaa                               1594
```

```
<210> SEQ ID NO 36
<211> LENGTH: 473
<212> TYPE: PRT
<213> ORGANISM: Ovis aries

<400> SEQUENCE: 36

Asn Pro Leu Trp Thr Leu Leu Phe Val Leu Ser Ala Pro Arg Gly Val
1               5                   10                  15

Leu Ser Gln Val Arg Leu Gln Glu Ser Gly Pro Ser Leu Ala Thr Leu
            20                  25                  30

Leu Gln Thr Leu Ser Val Thr Cys Thr Ile Ser Gly Phe Ser Leu Asn
        35                  40                  45

Asn Tyr Gly Val Asp Trp Val Arg Gln Ala Pro Gly Lys Ala Leu Glu
    50                  55                  60

Trp Leu Gly Gly Ser Gly Tyr Asp Glu Asp Ile Asp Tyr Asn Pro Val
65                  70                  75                  80

Leu Lys Ser Arg Leu Ser Ile Thr Lys Asp Thr Ser Lys Ser Gln Val
                85                  90                  95

Ser Leu Thr Leu Ser Thr Val Thr Thr Glu Asp Thr Ala Val Tyr Tyr
            100                 105                 110

Cys Ala Arg Val Asp Tyr Asp Ser Ser His Ala Phe Ala Tyr Ala Ser
        115                 120                 125

Tyr Asp Phe Trp Gly Pro Gly Leu Leu Ile Ser Val Leu Ser Ala Ser
    130                 135                 140

Thr Thr Pro Pro Lys Val Tyr Pro Leu Thr Ser Cys Cys Gly Asp Thr
145                 150                 155                 160

Ser Ser Ser Ile Val Thr Leu Gly Cys Leu Val Ser Ser Tyr Met Pro
                165                 170                 175

Glu Pro Val Thr Val Thr Trp Asn Ser Gly Ala Leu Thr Ser Gly Val
            180                 185                 190

His Thr Phe Pro Ala Ile Leu Gln Ser Ser Gly Leu Tyr Ser Leu Ser
        195                 200                 205

Ser Val Val Thr Val Pro Ala Ser Thr Ser Gly Ala Gln Thr Phe Ile
    210                 215                 220
```

```
Cys Asn Val Ala His Pro Ala Ser Ser Thr Lys Val Asp Lys Arg Val
225                 230                 235                 240

Glu Pro Gly Cys Pro Asp Pro Cys Lys His Cys Arg Cys Pro Pro Pro
                245                 250                 255

Glu Leu Pro Gly Gly Pro Ser Val Phe Ile Phe Pro Pro Lys Pro Lys
            260                 265                 270

Asp Thr Leu Thr Ile Ser Gly Thr Pro Glu Val Thr Cys Val Val Val
        275                 280                 285

Asp Val Gly Gln Asp Asp Pro Glu Val Gln Phe Ser Trp Phe Val Asp
    290                 295                 300

Asn Val Glu Val Arg Thr Ala Arg Thr Lys Pro Arg Glu Glu Gln Phe
305                 310                 315                 320

Asn Ser Thr Phe Arg Val Val Ser Ala Leu Pro Ile Gln His Gln Asp
                325                 330                 335

Trp Thr Gly Gly Lys Glu Phe Lys Cys Lys Val His Asn Glu Ala Leu
            340                 345                 350

Pro Ala Pro Ile Val Arg Thr Ile Ser Arg Thr Lys Gly Gln Ala Arg
        355                 360                 365

Glu Pro Gln Val Tyr Val Leu Ala Pro Pro Gln Glu Glu Leu Ser Lys
    370                 375                 380

Ser Thr Leu Ser Val Thr Cys Leu Val Thr Gly Phe Tyr Pro Asp Tyr
385                 390                 395                 400

Ile Ala Val Glu Trp Gln Lys Asn Gly Gln Pro Glu Ser Glu Asp Lys
                405                 410                 415

Tyr Gly Thr Thr Thr Ser Gln Leu Asp Ala Asp Gly Ser Tyr Phe Leu
            420                 425                 430

Tyr Ser Arg Leu Arg Val Asp Lys Asn Ser Trp Gln Glu Gly Asp Thr
        435                 440                 445

Tyr Ala Cys Val Val Met His Glu Ala Leu His Asn His Tyr Thr Gln
    450                 455                 460

Lys Ser Ile Ser Lys Pro Pro Gly Lys
465                 470


<210> SEQ ID NO 37
<211> LENGTH: 1561
<212> TYPE: DNA
<213> ORGANISM: Cricetulus migratorius

<400> SEQUENCE: 37

cccattcagt gagcagcact gaaaacaaga caatcaacat ggtgttgggg ctgcactggg      60

ttttctttgt tgctctttta aaaggtgtcc actgtgaggt gcagctggtt gagtctggtg     120

gaggattagt gaagcctgca ggatcactga aactctcctg tctggcttct ggattcgcct     180

tcagtgacta tttcatgagc tggttccgcc aggctccagg gaagggactg gaatgggttg     240

ctggcataga cactaaaagt tatgattatg caacctatta ctctggttcg gtgaaaggca     300

gattcaccat ctccagagat gattcccaaa gcatggtcta cctgcaaatg aacaacctga     360

gaactgagga cacagccact tactactgta caagagaaat cggatactgg ggccaaggaa     420

ccatggtcgc cgtctcctca gccacaacaa cagccccatc tgtctatccc ttggcccctg     480

cctgtgacag cacaaccagc accacggaca cggtgaccct gggatgcctg gtcaagggct     540

atttccctga gccggtgacc gtaagctgga actctggagc cctgaccagc ggcgtgcaca     600

ccttcccatc tgtcctgcat tctgggctct actccctcag cagctcagtg actgtacctt     660

ccagcacctg gcccaagcag cccatcacct gcaacgtagc ccacccggcc agcagcacca     720
```

-continued

```
aggtggacaa gaaaatcgag cccagaactg atacggatac atgtcctaat ccaccggatc    780

catgtcccac gtgtccaact cctgacctct tgggtggacc atctgtcttc atcttccccc    840

caaagcccaa ggatgtgctc atgatctccc tgacccccaa gatcacatgt gtggtggtgg    900

acgtgagcga ggaggagcca gacgtccagt tcaactggta tgtgaacaac gtagaagaca    960

agacagctca gacagagacc cggcagcggc agtacaacag cacctaccgc gtggtcagcg   1020

tcctccccat caagcaccag gactggatga gtggcaaggt gttcaaatgc aaggtcaaca   1080

acaatgccct ccctagcccc attgagaaaa ccatctccaa acccagaggg caagtccggg   1140

taccacagat atatacettt cctccgccta tagaacagac agtcaagaaa gatgtcagtg   1200

tgacctgcct ggtcacaggc ttcctccctc aggacatcca cgtggaatgg gagagcaatg   1260

ggcagccaca gccagagcag aactacaaga acacccagcc tgtcttggac tccgatggct   1320

cttacttcct gtacagcaag ctcaatgtgc ccaagagcag gtgggaccag ggagattcct   1380

tcacctgctc cgtgatacat gaggctctgc acaaccacca catgacgaag accatctccc   1440

ggtctctggg taattgagct cagcacccag aaagctctta ggtcctaagc taccctggca   1500

ccctcctcca cccttccctt gtataaataa agcacccagc actgccctga aaaaaaaaaa   1560

a                                                                   1561
```

<210> SEQ ID NO 38
<211> LENGTH: 472
<212> TYPE: PRT
<213> ORGANISM: Cricetulus migratorius

<400> SEQUENCE: 38

```
Met Val Leu Gly Leu His Trp Val Phe Phe Val Ala Leu Leu Lys Gly
1               5                   10                  15

Val His Cys Glu Val Gln Leu Val Glu Ser Gly Gly Gly Leu Val Lys
            20                  25                  30

Pro Ala Gly Ser Leu Lys Leu Ser Cys Leu Ala Ser Gly Phe Ala Phe
        35                  40                  45

Ser Asp Tyr Phe Met Ser Trp Phe Arg Gln Ala Pro Gly Lys Gly Leu
    50                  55                  60

Glu Trp Val Ala Gly Ile Asp Thr Lys Ser Tyr Asp Tyr Ala Thr Tyr
65                  70                  75                  80

Tyr Ser Gly Ser Val Lys Gly Arg Phe Thr Ile Ser Arg Asp Asp Ser
                85                  90                  95

Gln Ser Met Val Tyr Leu Gln Met Asn Asn Leu Arg Thr Glu Asp Thr
            100                 105                 110

Ala Thr Tyr Tyr Cys Thr Arg Glu Ile Gly Tyr Trp Gly Gln Gly Thr
        115                 120                 125

Met Val Ala Val Ser Ser Ala Thr Thr Thr Ala Pro Ser Val Tyr Pro
    130                 135                 140

Leu Ala Pro Ala Cys Asp Ser Thr Thr Ser Thr Thr Asp Thr Val Thr
145                 150                 155                 160

Leu Gly Cys Leu Val Lys Gly Tyr Phe Pro Glu Pro Val Thr Val Ser
                165                 170                 175

Trp Asn Ser Gly Ala Leu Thr Ser Gly Val His Thr Phe Pro Ser Val
            180                 185                 190

Leu His Ser Gly Leu Tyr Ser Leu Ser Ser Ser Val Thr Val Pro Ser
        195                 200                 205

Ser Thr Trp Pro Lys Gln Pro Ile Thr Cys Asn Val Ala His Pro Ala
    210                 215                 220
```

```
Ser Ser Thr Lys Val Asp Lys Lys Ile Glu Pro Arg Thr Asp Thr Asp
225                 230                 235                 240

Thr Cys Pro Asn Pro Pro Asp Pro Cys Pro Thr Cys Pro Thr Pro Asp
                245                 250                 255

Leu Leu Gly Gly Pro Ser Val Phe Ile Phe Pro Pro Lys Pro Lys Asp
            260                 265                 270

Val Leu Met Ile Ser Leu Thr Pro Lys Ile Thr Cys Val Val Val Asp
        275                 280                 285

Val Ser Glu Glu Glu Pro Asp Val Gln Phe Asn Trp Tyr Val Asn Asn
    290                 295                 300

Val Glu Asp Lys Thr Ala Gln Thr Glu Thr Arg Gln Arg Gln Tyr Asn
305                 310                 315                 320

Ser Thr Tyr Arg Val Val Ser Val Leu Pro Ile Lys His Gln Asp Trp
                325                 330                 335

Met Ser Gly Lys Val Phe Lys Cys Lys Val Asn Asn Asn Ala Leu Pro
            340                 345                 350

Ser Pro Ile Glu Lys Thr Ile Ser Lys Pro Arg Gly Gln Val Arg Val
        355                 360                 365

Pro Gln Ile Tyr Thr Phe Pro Pro Pro Ile Glu Gln Thr Val Lys Lys
    370                 375                 380

Asp Val Ser Val Thr Cys Leu Val Thr Gly Phe Leu Pro Gln Asp Ile
385                 390                 395                 400

His Val Glu Trp Glu Ser Asn Gly Gln Pro Gln Pro Glu Gln Asn Tyr
                405                 410                 415

Lys Asn Thr Gln Pro Val Leu Asp Ser Asp Gly Ser Tyr Phe Leu Tyr
            420                 425                 430

Ser Lys Leu Asn Val Pro Lys Ser Arg Trp Asp Gln Gly Asp Ser Phe
        435                 440                 445

Thr Cys Ser Val Ile His Glu Ala Leu His Asn His His Met Thr Lys
    450                 455                 460

Thr Ile Ser Arg Ser Leu Gly Asn
465                 470


<210> SEQ ID NO 39
<211> LENGTH: 1092
<212> TYPE: DNA
<213> ORGANISM: Rattus rattus

<400> SEQUENCE: 39

gccagaacaa cagccccatc tgtctatccc ttggtccctg gatgcagtgg cacatctgga     60

tccttggtaa cactaggatg ccttgtcaaa ggctatttcc ctgagccggt aaccgtaaaa    120

tggaactctg gagccctgtc cagcggtgtg cacaccttcc cagctgtcct gcagtctggg    180

ctctacaccc tcagcagctc ggtgactgtt ccctccagca cctggtccag ccagaccgtc    240

acctgcagcg tagcccaccc agccaccaaa agcaacttga tcaagagaat tgagcccaga    300

agacccaagc ccagaccccc cacagatatc tgttcatgtg atgacaactt gggtagacca    360

tctgtcttca tcttcccccc aaagcccaag gatatactca tgatcaccct gacccccaag    420

gtcacctgtg tggtggtgga tgtgagcgag gaggagccag acgtccagtt cagctggttt    480

gtggacaacg tacgagtatt cacagctcag acacaacccc atgaggagca gctcaacggt    540

accttccgag tggtcagtac cctccatatc cagcaccagg actggatgag cggcaaggag    600

ttcaaatgca aggtcaacaa caaagacctc ccaagcccca tcgagaaaac catctcaaaa    660

cccagaggaa aagcccggac acctcaagta tacaccattc ctccacctcg tgaacaaatg    720
```

```
tccaagaata aggttagcct cacctgcatg gtcaccagct tctaccccgc atccatcagt    780

gtggagtggg aaaggaatgg ggagctggag caggactaca agaacaccct acccgtgctg    840

gactcagatg agtcctactt cctctacagc aagctcagtg tggacacgga cagttggatg    900

cgaggagaca tttatacctg ctctgtggtg cacgaggctc ttcataacca ccacacacag    960

aagaacctgt cccgctctcc tggtaaatga gcacagtgct taggccacac cccaggtctt   1020

acaagacact gacaccagcc ctaacccctg atcctataaa taaagcaccc agagatggga   1080

ccctgtgaga tt                                                       1092


<210> SEQ ID NO 40
<211> LENGTH: 329
<212> TYPE: PRT
<213> ORGANISM: Rattus rattus

<400> SEQUENCE: 40

Ala Arg Thr Thr Ala Pro Ser Val Tyr Pro Leu Val Pro Gly Cys Ser
1               5                   10                  15

Gly Thr Ser Gly Ser Leu Val Thr Leu Gly Cys Leu Val Lys Gly Tyr
            20                  25                  30

Phe Pro Glu Pro Val Thr Val Lys Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Ser Ser Ser Val Thr Val Pro Ser Ser Thr Trp Ser Ser Gln Thr Val
65                  70                  75                  80

Thr Cys Ser Val Ala His Pro Ala Thr Lys Ser Asn Leu Ile Lys Arg
                85                  90                  95

Ile Glu Pro Arg Arg Pro Lys Pro Arg Pro Pro Thr Asp Ile Cys Ser
            100                 105                 110

Cys Asp Asp Asn Leu Gly Arg Pro Ser Val Phe Ile Phe Pro Pro Lys
        115                 120                 125

Pro Lys Asp Ile Leu Met Ile Thr Leu Thr Pro Lys Val Thr Cys Val
    130                 135                 140

Val Val Asp Val Ser Glu Glu Glu Pro Asp Val Gln Phe Ser Trp Phe
145                 150                 155                 160

Val Asp Asn Val Arg Val Phe Thr Ala Gln Thr Gln Pro His Glu Glu
                165                 170                 175

Gln Leu Asn Gly Thr Phe Arg Val Val Ser Thr Leu His Ile Gln His
            180                 185                 190

Gln Asp Trp Met Ser Gly Lys Glu Phe Lys Cys Lys Val Asn Asn Lys
        195                 200                 205

Asp Leu Pro Ser Pro Ile Glu Lys Thr Ile Ser Lys Pro Arg Gly Lys
    210                 215                 220

Ala Arg Thr Pro Gln Val Tyr Thr Ile Pro Pro Pro Arg Glu Gln Met
225                 230                 235                 240

Ser Lys Asn Lys Val Ser Leu Thr Cys Met Val Thr Ser Phe Tyr Pro
                245                 250                 255

Ala Ser Ile Ser Val Glu Trp Glu Arg Asn Gly Glu Leu Glu Gln Asp
            260                 265                 270

Tyr Lys Asn Thr Leu Pro Val Leu Asp Ser Asp Glu Ser Tyr Phe Leu
        275                 280                 285

Tyr Ser Lys Leu Ser Val Asp Thr Asp Ser Trp Met Arg Gly Asp Ile
    290                 295                 300

Tyr Thr Cys Ser Val Val His Glu Ala Leu His Asn His His Thr Gln
```

-continued

```
305                 310                 315                 320

Lys Asn Leu Ser Arg Ser Pro Gly Lys
                325


<210> SEQ ID NO 41
<211> LENGTH: 1064
<212> TYPE: DNA
<213> ORGANISM: Trichosurus vulpecula

<400> SEQUENCE: 41

gccagcccca cagctccatc tgtctttgcc ctggcaccca attgtggaca gggaacctcc      60

tcccaagtag ctatggcctg cctggtgtca aactacttcc ctgagcctgt gacagtgaca     120

tggaattccg gggccatctc cagtggaatc cagacctatc cttctatcct ccagtcctca     180

ggactctaca cctcaagcag tcagttgaca gttcctgcag atgattggct cacaaagtca     240

tacatctgca atgtggccca caaacccaca tccaccaaaa ctgacaagaa aattgaaaag     300

atttccgagt gtacatgctg caaatgccaa gcatgtgatg tcgttggacc ttctgtattc     360

ctcttccccc caaatcctaa ggacaccctc acactctcaa gagtccctaa aatcacctgt     420

gtggtggttg atgtgagtga tgcctcagag gttcaaattt cctggtacaa aggcgaaaac     480

gcaatcgaca gtcctaaacc gacagagagg aaactaaaca acggcacctt tcaggtggtc     540

agcactctct ctgtagccca ccaagaatgg ctgaatggcg tggcatacac ctgtaaagtt     600

gataacaaag aattaccata tcctgagaga aagaccatct ttcatactaa gggtaacaga     660

aagaagcctg atgtgtatgt ctttgcccca catcctgatg agttgaagca aaaagatact     720

gttagtatta cctgcctagt aaaaagtttc ttccctaaag aagttgttgt tgaatggcaa     780

tgcaacaaca atccagagtc tgaagataac tattccacca ctgaagcaat gagggaaaac     840

gacaccttct ttgtctatag caagctcaat gtgaagaaaa caaaatggca agagaataac     900

cactacacct gcacggtgct gcatgaggcc cttccgaacc aaacttccca gaggacaatc     960

tctgcatcat cccccggtaa atgagagagc aaagagaaat acacacacac acataaatac    1020

acacacacac acacacacac gcacacaaat tgccctcgtg ccgc                     1064


<210> SEQ ID NO 42
<211> LENGTH: 327
<212> TYPE: PRT
<213> ORGANISM: Trichosurus vulpecula

<400> SEQUENCE: 42

Ala Ser Pro Thr Ala Pro Ser Val Phe Ala Leu Ala Pro Asn Cys Gly
1               5                   10                  15

Gln Gly Thr Ser Ser Gln Val Ala Met Ala Cys Leu Val Ser Asn Tyr
            20                  25                  30

Phe Pro Glu Pro Val Thr Val Thr Trp Asn Ser Gly Ala Ile Ser Ser
        35                  40                  45

Gly Ile Gln Thr Tyr Pro Ser Ile Leu Gln Ser Ser Gly Leu Tyr Thr
    50                  55                  60

Ser Ser Ser Gln Leu Thr Val Pro Ala Asp Asp Trp Leu Thr Lys Ser
65                  70                  75                  80

Tyr Ile Cys Asn Val Ala His Lys Pro Thr Ser Thr Lys Thr Asp Lys
                85                  90                  95

Lys Ile Glu Lys Ile Ser Glu Cys Thr Cys Cys Lys Cys Gln Ala Cys
            100                 105                 110

Asp Val Val Gly Pro Ser Val Phe Leu Phe Pro Pro Asn Pro Lys Asp
        115                 120                 125
```

```
Thr Leu Thr Leu Ser Arg Val Pro Lys Ile Thr Cys Val Val Val Asp
    130                 135                 140

Val Ser Asp Ala Ser Glu Val Gln Ile Ser Trp Tyr Lys Gly Glu Asn
145                 150                 155                 160

Ala Ile Asp Ser Pro Lys Pro Thr Glu Arg Lys Leu Asn Asn Gly Thr
                165                 170                 175

Phe Gln Val Val Ser Thr Leu Ser Val Ala His Gln Glu Trp Leu Asn
            180                 185                 190

Gly Val Ala Tyr Thr Cys Lys Val Asp Asn Lys Glu Leu Pro Tyr Pro
        195                 200                 205

Glu Arg Lys Thr Ile Phe His Thr Lys Gly Asn Arg Lys Lys Pro Asp
    210                 215                 220

Val Tyr Val Phe Ala Pro His Pro Asp Glu Leu Lys Gln Lys Asp Thr
225                 230                 235                 240

Val Ser Ile Thr Cys Leu Val Lys Ser Phe Phe Pro Lys Glu Val Val
                245                 250                 255

Val Glu Trp Gln Cys Asn Asn Asn Pro Glu Ser Glu Asp Asn Tyr Ser
            260                 265                 270

Thr Thr Glu Ala Met Arg Glu Asn Asp Thr Phe Phe Val Tyr Ser Lys
        275                 280                 285

Leu Asn Val Lys Lys Thr Lys Trp Gln Glu Asn Asn His Tyr Thr Cys
    290                 295                 300

Thr Val Leu His Glu Ala Leu Pro Asn Gln Thr Ser Gln Arg Thr Ile
305                 310                 315                 320

Ser Ala Ser Ser Pro Gly Lys
                325
```

<210> SEQ ID NO 43
<211> LENGTH: 1699
<212> TYPE: DNA
<213> ORGANISM: Monodelphis domestica

<400> SEQUENCE: 43

```
ggccaggact gaaccagagt cctcatcatg gactttaggc taaactggtt tttctttcta     60

ataactttac aaggtgttga cagtgaggtt cagctggtgg agactggggg agatgtgagg    120

cagcctgggg gctctcttcg actcacttgt acaagttctg gatttacctt atccacctac    180

tacatgcatt ggattcgaca ggctccaggc aaggggctgg agtgggtcgc tgtaataaga    240

aatcctgcta atggtcttac tgcagaatat ggagaggctg tgaaaggccg attcaccatt    300

tccagagatg atgccagtaa gatggtatat ttgcaaatga acaacttgaa aactgaggac    360

acagcaacat atttttgttc aaaagatctt gagttttggg gcaaggggac cacggtgact    420

gtatcctcag ccagacccac agctccatcc gtctttcccc tggtatccag ttgtggacag    480

gaaacacagg cccagatggc tctgggctgc ctggtgacaa gctacttccc tgagccagtg    540

acagtgacat ggaattcagg gaccaccacc agtggaatcc agacctatcc ctctgtactc    600

cagccctcag gactctacac tttaaccagt cagttgacaa ttcctgcaga ttcttggtcc    660

tctcagtcat atacctgcaa tgtggctcac ccagccacat ccaccaagat cgacaagaaa    720

attgaagcaa ctactacaac atgtccatgc tgcaaatgca acacagttga cgccggtgga    780

ccttctgttt ttgtcttccc tccaaatcct caggatgtcc tcaaactctc aagatcccct    840

aaagttacct gtatggtggt tgatgtaagt gatgcatcag gtgttcagat tacctggttc    900

aaaggtgaag aggaagtcag cagtcctaaa ctcacccaga agaaattaaa caatggcacc    960
```

```
tttcaggtgg tcagcaatct ccctgtagtc caccaggaat ggctgaaagg cacttcatac   1020

acctgtaaag ttaataccag tgaactacca gttgttgaga gaaagaccat atcccacact   1080

aaaggtgaga gaaagaagcc tgatatatat gtctttggcc cacatcctga tgagttgaaa   1140

caaaaagatg atgtcagtat tacctgccta gtgaccaatt tcttccctga agatgttgtt   1200

atcgaatggc aaaagaacaa caatccagag tctgaagata aatattacac caccccaaca   1260

acgagggaaa agagcaccta ctttttctac agcaagctta ttgtgaagaa aagagattgg   1320

gataaccaaa actcctatac ctgcgtagtg ttgcatgagg cctttccaaa ccaaatttcc   1380

cagaggacaa tctctgcatc cccgggtaaa tgagaaagcc aagagaatca cacacataca   1440

cacacacaca cacacacaca cacacacaca cacacacaca ccacacacat catcatcatc   1500

atcattatca tcatcatcat cccatcccct cctccaggga tagccagtct ggaggagttc   1560

cctgtctact tcttacccaa ttctccttca tagggtcttc cctccttcat attttccaag   1620

gcttggcgat agaagcctca catgtaaata ctttccatta tcctcaagca aaataataaa   1680

acacccagca ccataaaaa                                                1699
```

```
<210> SEQ ID NO 44
<211> LENGTH: 461
<212> TYPE: PRT
<213> ORGANISM: Monodelphis domestica

<400> SEQUENCE: 44

Met Asp Phe Arg Leu Asn Trp Phe Phe Phe Leu Ile Thr Leu Gln Gly
1               5                   10                  15

Val Asp Ser Glu Val Gln Leu Val Glu Thr Gly Gly Asp Val Arg Gln
            20                  25                  30

Pro Gly Gly Ser Leu Arg Leu Thr Cys Thr Ser Ser Gly Phe Thr Leu
        35                  40                  45

Ser Thr Tyr Tyr Met His Trp Ile Arg Gln Ala Pro Gly Lys Gly Leu
    50                  55                  60

Glu Trp Val Ala Val Ile Arg Asn Pro Ala Asn Gly Leu Thr Ala Glu
65                  70                  75                  80

Tyr Gly Glu Ala Val Lys Gly Arg Phe Thr Ile Ser Arg Asp Asp Ala
                85                  90                  95

Ser Lys Met Val Tyr Leu Gln Met Asn Asn Leu Lys Thr Glu Asp Thr
            100                 105                 110

Ala Thr Tyr Phe Cys Ser Lys Asp Leu Glu Phe Trp Gly Lys Gly Thr
        115                 120                 125

Thr Val Thr Val Ser Ser Ala Arg Pro Thr Ala Pro Ser Val Phe Pro
    130                 135                 140

Leu Val Ser Ser Cys Gly Gln Glu Thr Gln Ala Gln Met Ala Leu Gly
145                 150                 155                 160

Cys Leu Val Thr Ser Tyr Phe Pro Glu Pro Val Thr Val Thr Trp Asn
                165                 170                 175

Ser Gly Thr Thr Thr Ser Gly Ile Gln Thr Tyr Pro Ser Val Leu Gln
            180                 185                 190

Pro Ser Gly Leu Tyr Thr Leu Thr Ser Gln Leu Thr Ile Pro Ala Asp
        195                 200                 205

Ser Trp Ser Ser Gln Ser Tyr Thr Cys Asn Val Ala His Pro Ala Thr
    210                 215                 220

Ser Thr Lys Ile Asp Lys Lys Ile Glu Ala Thr Thr Thr Thr Cys Pro
225                 230                 235                 240

Cys Cys Lys Cys Asn Thr Val Asp Ala Gly Gly Pro Ser Val Phe Val
```

-continued

```
                245                 250                 255

Phe Pro Pro Asn Pro Gln Asp Val Leu Lys Leu Ser Arg Ser Pro Lys
            260                 265                 270

Val Thr Cys Met Val Val Asp Val Ser Asp Ala Ser Gly Val Gln Ile
        275                 280                 285

Thr Trp Phe Lys Gly Glu Glu Glu Val Ser Ser Pro Lys Leu Thr Gln
    290                 295                 300

Lys Lys Leu Asn Asn Gly Thr Phe Gln Val Val Ser Asn Leu Pro Val
305                 310                 315                 320

Val His Gln Glu Trp Leu Lys Gly Thr Ser Tyr Thr Cys Lys Val Asn
                325                 330                 335

Thr Ser Glu Leu Pro Val Val Glu Arg Lys Thr Ile Ser His Thr Lys
            340                 345                 350

Gly Glu Arg Lys Lys Pro Asp Ile Tyr Val Phe Gly Pro His Pro Asp
        355                 360                 365

Glu Leu Lys Gln Lys Asp Asp Val Ser Ile Thr Cys Leu Val Thr Asn
    370                 375                 380

Phe Phe Pro Glu Asp Val Val Ile Glu Trp Gln Lys Asn Asn Asn Pro
385                 390                 395                 400

Glu Ser Glu Asp Lys Tyr Tyr Thr Thr Pro Thr Thr Arg Glu Lys Ser
                405                 410                 415

Thr Tyr Phe Phe Tyr Ser Lys Leu Ile Val Lys Lys Arg Asp Trp Asp
            420                 425                 430

Asn Gln Asn Ser Tyr Thr Cys Val Val Leu His Glu Ala Phe Pro Asn
        435                 440                 445

Gln Ile Ser Gln Arg Thr Ile Ser Ala Ser Pro Gly Lys
    450                 455                 460
```

<210> SEQ ID NO 45
<211> LENGTH: 25
<212> TYPE: DNA
<213> ORGANISM: Artificial Sequence
<220> FEATURE:
<223> OTHER INFORMATION: Forward primer

<400> SEQUENCE: 45
cccgggtatg agctacaact tgctt 25

<210> SEQ ID NO 46
<211> LENGTH: 27
<212> TYPE: DNA
<213> ORGANISM: Artificial Sequence
<220> FEATURE:
<223> OTHER INFORMATION: Reverse primer

<400> SEQUENCE: 46
ctcgagtcag tttcggaggt aacctgt 27

<210> SEQ ID NO 47
<211> LENGTH: 38
<212> TYPE: DNA
<213> ORGANISM: Artificial Sequence
<220> FEATURE:
<223> OTHER INFORMATION: A forward primer

<400> SEQUENCE: 47
agaagcagca attttcagag tcagaagctc ctgtggca 38

<210> SEQ ID NO 48
<211> LENGTH: 38

<212> TYPE: DNA
<213> ORGANISM: Artificial Sequence
<220> FEATURE:
<223> OTHER INFORMATION: A reverse primer

<400> SEQUENCE: 48
tgccacagga gcttctgact ctgaaaattg ctgcttct 38

<210> SEQ ID NO 49
<211> LENGTH: 48
<212> TYPE: DNA
<213> ORGANISM: Artificial Sequence
<220> FEATURE:
<223> OTHER INFORMATION: An oligonucleotide sequence of a flexible linker

<400> SEQUENCE: 49
gggtgcaggg ggcgggggca gcgggggcgg aggatccggc gggggctc 48

<210> SEQ ID NO 50
<211> LENGTH: 16
<212> TYPE: PRT
<213> ORGANISM: Artificial Sequence
<220> FEATURE:
<223> OTHER INFORMATION: A linker amino acid sequence

<400> SEQUENCE: 50

Gly Ala Gly Gly Gly Gly Ser Gly Gly Gly Gly Ser Gly Gly Gly Ser
1 5 10 15

<210> SEQ ID NO 51
<211> LENGTH: 7
<212> TYPE: DNA
<213> ORGANISM: Artificial Sequence
<220> FEATURE:
<223> OTHER INFORMATION: A sequence containing a Sma I site

<400> SEQUENCE: 51 cccgggt 7

<210> SEQ ID NO 52
<211> LENGTH: 6
<212> TYPE: PRT
<213> ORGANISM: Artificial Sequence
<220> FEATURE:
<223> OTHER INFORMATION: A C-terminal amino acid sequence of IgG4

<400> SEQUENCE: 52

Leu Ser Leu Ser Pro Gly
1 5

<210> SEQ ID NO 53
<211> LENGTH: 7
<212> TYPE: PRT
<213> ORGANISM: Artificial Sequence
<220> FEATURE:
<223> OTHER INFORMATION: A C-terminal amino acid sequence of IgG1, IgG2 or IgG3

<400> SEQUENCE: 53

Leu Ser Leu Ser Pro Gly Ala
1 5

<210> SEQ ID NO 54
<211> LENGTH: 38
<212> TYPE: DNA
<213> ORGANISM: Artificial Sequence
<220> FEATURE:

<223> OTHER INFORMATION: A forward primer to introduce C17A mutation

<400> SEQUENCE: 54
agaagcagca attttcaggc tcagaagctc ctgtggca 38

<210> SEQ ID NO 55
<211> LENGTH: 38
<212> TYPE: DNA
<213> ORGANISM: Artificial Sequence
<220> FEATURE:
<223> OTHER INFORMATION: A reverse primer to introduce C17A mutation

<400> SEQUENCE: 55
tgccacagga gcttctgagc ctgaaaattg ctgcttct 38

<210> SEQ ID NO 56
<211> LENGTH: 24
<212> TYPE: DNA
<213> ORGANISM: Artificial Sequence
<220> FEATURE:
<223> OTHER INFORMATION: A forward primer to introduce H131A mutation

<400> SEQUENCE: 56
ctccctgtcc ccgggtgcag gggg 24

<210> SEQ ID NO 57
<211> LENGTH: 38
<212> TYPE: DNA
<213> ORGANISM: Artificial Sequence
<220> FEATURE:
<223> OTHER INFORMATION: A reverse primer to introduce H131A mutation

<400> SEQUENCE: 57
cttggccttc aggtaggcca gaatcctccc ataatatc 38

<210> SEQ ID NO 58
<211> LENGTH: 38
<212> TYPE: DNA
<213> ORGANISM: Artificial Sequence
<220> FEATURE:
<223> OTHER INFORMATION: A second forward primer to introduce H131A
mutation

<400> SEQUENCE: 58
gatattatgg gaggattctg gcctacctga aggccaag 38

<210> SEQ ID NO 59
<211> LENGTH: 24
<212> TYPE: DNA
<213> ORGANISM: Artificial Sequence
<220> FEATURE:
<223> OTHER INFORMATION: A second reverse primer to introduce H131A
mutation

<400> SEQUENCE: 59
cttatcatgt ctggatccct cgag 24

<210> SEQ ID NO 60
<211> LENGTH: 24
<212> TYPE: DNA
<213> ORGANISM: Artificial Sequence
<220> FEATURE:
<223> OTHER INFORMATION: A forward primer containing XmaI site

<400> SEQUENCE: 60
ctccctgtcc ccgggtgcag gggg 24

<210> SEQ ID NO 61
<211> LENGTH: 24
<212> TYPE: DNA
<213> ORGANISM: Artificial Sequence
<220> FEATURE:
<223> OTHER INFORMATION: A reverse primer containing BamH I

<400> SEQUENCE: 61
cttatcatgt ctggatccct cgag 24

<210> SEQ ID NO 62
<211> LENGTH: 24
<212> TYPE: DNA
<213> ORGANISM: Artificial Sequence
<220> FEATURE:
<223> OTHER INFORMATION: A forward primer to introduce H140A mutation

<400> SEQUENCE: 62
ctccctgtcc ccgggtgcag gggg 24

<210> SEQ ID NO 63
<211> LENGTH: 30
<212> TYPE: DNA
<213> ORGANISM: Artificial Sequence
<220> FEATURE:
<223> OTHER INFORMATION: A reverse primer to introduce H140A mutation

<400> SEQUENCE: 63
ggtccaggca caggcactgt actccttggc 30

<210> SEQ ID NO 64
<211> LENGTH: 30
<212> TYPE: DNA
<213> ORGANISM: Artificial Sequence
<220> FEATURE:
<223> OTHER INFORMATION: A second forward primer to introduce H140A
mutation

<400> SEQUENCE: 64
ggcaaggagt acagtgcctg tgcctggacc 30

<210> SEQ ID NO 65
<211> LENGTH: 24
<212> TYPE: DNA
<213> ORGANISM: Artificial Sequence
<220> FEATURE:
<223> OTHER INFORMATION: A second reverse primer to introduce H140A
mutation

<400> SEQUENCE: 65
cttatcatgt ctggatccct cgag 24

<210> SEQ ID NO 66
<211> LENGTH: 24
<212> TYPE: DNA
<213> ORGANISM: Artificial Sequence
<220> FEATURE:
<223> OTHER INFORMATION: A forward primer containing Xma I site

<400> SEQUENCE: 66
ctccctgtcc ccgggtgcag gggg 24

<210> SEQ ID NO 67
<211> LENGTH: 24
<212> TYPE: DNA
<213> ORGANISM: Artificial Sequence
<220> FEATURE:

<223> OTHER INFORMATION: A reverse primer containing BamH I site

<400> SEQUENCE: 67
cttatcatgt ctggatccct cgag 24

<210> SEQ ID NO 68
<211> LENGTH: 24
<212> TYPE: DNA
<213> ORGANISM: Artificial Sequence
<220> FEATURE:
<223> OTHER INFORMATION: A forward primer to introduce F50H or L57A mutation

<400> SEQUENCE: 68
ctccctgtcc ccgggtgcag gggg 24

<210> SEQ ID NO 69
<211> LENGTH: 33
<212> TYPE: DNA
<213> ORGANISM: Artificial Sequence
<220> FEATURE:
<223> OTHER INFORMATION: A reverse primer to introduce L57A mutation

<400> SEQUENCE: 69
gagcatctca tagatggtgg ctgcggcgtc ctc 33

<210> SEQ ID NO 70
<211> LENGTH: 27
<212> TYPE: DNA
<213> ORGANISM: Artificial Sequence
<220> FEATURE:
<223> OTHER INFORMATION: A reverse primer to introduce F50H mutation

<400> SEQUENCE: 70
gtcctccttc tgatgctgct gcagctg 27

<210> SEQ ID NO 71
<211> LENGTH: 33
<212> TYPE: DNA
<213> ORGANISM: Artificial Sequence
<220> FEATURE:
<223> OTHER INFORMATION: A second forward primer for L57A mutation

<400> SEQUENCE: 71
gaggacgccg cagccaccat ctatgagatg ctc 33

<210> SEQ ID NO 72
<211> LENGTH: 27
<212> TYPE: DNA
<213> ORGANISM: Artificial Sequence
<220> FEATURE:
<223> OTHER INFORMATION: A second forward primer for F50H mutation

<400> SEQUENCE: 72
cagctgcagc agcatcagaa ggaggac 27

<210> SEQ ID NO 73
<211> LENGTH: 24
<212> TYPE: DNA
<213> ORGANISM: Artificial Sequence
<220> FEATURE:
<223> OTHER INFORMATION: A second reverse primer containing BamH I site

<400> SEQUENCE: 73
cttatcatgt ctggatccct cgag 24

```
<210> SEQ ID NO 74
<211> LENGTH: 24
<212> TYPE: DNA
<213> ORGANISM: Artificial Sequence
<220> FEATURE:
<223> OTHER INFORMATION: A forward primer

<400> SEQUENCE: 74

ctccctgtcc ccgggtgcag gggg                                            24


<210> SEQ ID NO 75
<211> LENGTH: 24
<212> TYPE: DNA
<213> ORGANISM: Artificial Sequence
<220> FEATURE:
<223> OTHER INFORMATION: A reverse primer

<400> SEQUENCE: 75

cttatcatgt ctggatccct cgag                                            24


<210> SEQ ID NO 76
<211> LENGTH: 6
<212> TYPE: PRT
<213> ORGANISM: Homo sapiens

<400> SEQUENCE: 76

Leu Ser Leu Ser Leu Gly
1               5


<210> SEQ ID NO 77
<211> LENGTH: 397
<212> TYPE: PRT
<213> ORGANISM: Artificial Sequence
<220> FEATURE:
<223> OTHER INFORMATION: Fc-IFN-Beta protein comprising gamma 4 with a
      modified gamma 1 hinge sequence

<400> SEQUENCE: 77

Glu Pro Lys Ser Ser Asp Lys Thr His Thr Cys Pro Pro Cys Pro Ala
1               5                   10                  15

Pro Glu Phe Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser Gln Glu Asp Pro Glu Val Gln Phe Asn Trp Tyr Val
    50                  55                  60

Asp Gly Val Glu Val His Asn Ala Lys Thr Lys Pro Arg Glu Glu Gln
65                  70                  75                  80

Phe Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Gly
            100                 105                 110

Leu Pro Ser Ser Ile Glu Lys Thr Ile Ser Lys Ala Lys Gly Gln Pro
        115                 120                 125

Arg Glu Pro Gln Val Tyr Thr Leu Pro Pro Ser Gln Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190
```

```
Ser Lys Leu Thr Val Asp Lys Ser Arg Trp Gln Gln Gly Asn Ile Phe
        195                 200                 205

Ser Cys Ser Val Met His Glu Ala Leu His Asn His Tyr Thr Gln Lys
    210                 215                 220

Ser Leu Ser Leu Ser Pro Gly Met Ser Tyr Asn Leu Leu Gly Phe Leu
225                 230                 235                 240

Gln Arg Ser Ser Asn Phe Gln Cys Gln Lys Leu Leu Trp Gln Leu Asn
                245                 250                 255

Gly Arg Leu Glu Tyr Cys Leu Lys Asp Arg Met Asn Phe Asp Ile Pro
            260                 265                 270

Glu Glu Ile Lys Gln Leu Gln Gln Phe Gln Lys Glu Asp Ala Ala Leu
        275                 280                 285

Thr Ile Tyr Glu Met Leu Gln Asn Ile Phe Ala Ile Phe Arg Gln Asp
    290                 295                 300

Ser Ser Ser Thr Gly Trp Asn Glu Thr Ile Val Glu Asn Leu Leu Ala
305                 310                 315                 320

Asn Val Tyr His Gln Ile Asn His Leu Lys Thr Val Leu Glu Glu Lys
                325                 330                 335

Leu Glu Lys Glu Asp Phe Thr Arg Gly Lys Leu Met Ser Ser Leu His
            340                 345                 350

Leu Lys Arg Tyr Tyr Gly Arg Ile Leu His Tyr Leu Lys Ala Lys Glu
        355                 360                 365

Tyr Ser His Cys Ala Trp Thr Ile Val Arg Val Glu Ile Leu Arg Asn
    370                 375                 380

Phe Tyr Phe Ile Asn Arg Leu Thr Gly Tyr Leu Arg Asn
385                 390                 395


<210> SEQ ID NO 78
<211> LENGTH: 696
<212> TYPE: DNA
<213> ORGANISM: Homo sapiens
<220> FEATURE:
<221> NAME/KEY: CDS
<222> LOCATION: (1)..(696)

<400> SEQUENCE: 78

gag ccc aaa tct tct gac aaa act cac aca tgc cca ccg tgc cca gca       48
Glu Pro Lys Ser Ser Asp Lys Thr His Thr Cys Pro Pro Cys Pro Ala
1               5                   10                  15

cct gaa ctc ctg ggg gga ccg tca gtc ttc ctc ttc ccc cca aaa ccc       96
Pro Glu Leu Leu Gly Gly Pro Ser Val Phe Leu Phe Pro Pro Lys Pro
            20                  25                  30

aag gac acc ctc atg atc tcc cgg acc cct gag gtc aca tgc gtg gtg      144
Lys Asp Thr Leu Met Ile Ser Arg Thr Pro Glu Val Thr Cys Val Val
        35                  40                  45

gtg gac gtg agc cac gaa gac cct gag gtc aag ttc aac tgg tac gtg      192
Val Asp Val Ser His Glu Asp Pro Glu Val Lys Phe Asn Trp Tyr Val
    50                  55                  60

gac ggc gtg gag gtg cat aat gcc aag aca aag ccg cgg gag gag cag      240
Asp Gly Val Glu Val His Asn Ala Lys Thr Lys Pro Arg Glu Glu Gln
65                  70                  75                  80

tac aac agc acg tac cgt gtg gtc agc gtc ctc acc gtc ctg cac cag      288
Tyr Asn Ser Thr Tyr Arg Val Val Ser Val Leu Thr Val Leu His Gln
                85                  90                  95

gac tgg ctg aat ggc aag gag tac aag tgc aag gtc tcc aac aaa gcc      336
Asp Trp Leu Asn Gly Lys Glu Tyr Lys Cys Lys Val Ser Asn Lys Ala
            100                 105                 110

ctc cca gcc ccc atc gag aaa acc atc tcc aaa gcc aaa ggg cag ccc      384
```

-continued

```
Leu Pro Ala Pro Ile Glu Lys Thr Ile Ser Lys Ala Lys Gly Gln Pro
        115                 120                 125

cga gaa cca cag gtg tac acc ctg ccc cca tca cgg gag gag atg acc      432
Arg Glu Pro Gln Val Tyr Thr Leu Pro Pro Ser Arg Glu Glu Met Thr
    130                 135                 140

aag aac cag gtc agc ctg acc tgc ctg gtc aaa ggc ttc tat ccc agc      480
Lys Asn Gln Val Ser Leu Thr Cys Leu Val Lys Gly Phe Tyr Pro Ser
145                 150                 155                 160

gac atc gcc gtg gag tgg gag agc aat ggg cag ccg gag aac aac tac      528
Asp Ile Ala Val Glu Trp Glu Ser Asn Gly Gln Pro Glu Asn Asn Tyr
                165                 170                 175

aag acc acg cct ccc gtg ctg gac tcc gac ggc tcc ttc ttc ctc tat      576
Lys Thr Thr Pro Pro Val Leu Asp Ser Asp Gly Ser Phe Phe Leu Tyr
            180                 185                 190

agc aag ctc acc gtg gac aag agc agg tgg cag cag ggg aac gtc ttc      624
Ser Lys Leu Thr Val Asp Lys Ser Arg Trp Gln Gln Gly Asn Val Phe
        195                 200                 205

tca tgc tcc gtg atg cat gag gct ctg cac aac cac tac acg cag aag      672
Ser Cys Ser Val Met His Glu Ala Leu His Asn His Tyr Thr Gln Lys
    210                 215                 220

agc ctc tcc ctg tcc ccg ggt aaa                                      696
Ser Leu Ser Leu Ser Pro Gly Lys
225                 230


<210> SEQ ID NO 79
<211> LENGTH: 232
<212> TYPE: PRT
<213> ORGANISM: Homo sapiens

<400> SEQUENCE: 79

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220
```

-continued

```
Ser Leu Ser Leu Ser Pro Gly Lys
225                 230
```

STABILIZATION OF FC-INTERFERON-BETA FUSION PROTEINS

CROSS-REFERENCE TO RELATED APPLICATION

This application is a divisional application of U.S. application Ser. No. 11/167,767, filed Jun. 27, 2005, and issued as U.S. Pat. No. 7,670,595 on Mar. 2, 2010, which claims priority to and the benefit of U.S. Provisional Patent Application No. 60/583,389, filed on Jun. 28, 2004, the entire disclosures of each of which are incorporated by reference herein.

FIELD OF THE INVENTION

The invention relates to Fc-fusion proteins. More specifically, the invention relates to high-level expression and secretion of Fc-interferon-beta fusion proteins and variant forms thereof, and methods of making and using such proteins.

BACKGROUND OF THE INVENTION

Interferons are single chain polypeptides secreted by most animal cells in response to a variety of stimuli, including viruses, mitogens and cytokines. Interferons participate in the regulation of cell functions and mediate antiproliferative, antiviral and immunomodulatory effects. Thus, they are of great interest therapeutically. Native interferons are divided into three major types, based on the cell types from which they are primarily derived, namely, interferon-α (from leukocytes), interferon-β (from fibroblasts), interferon-γ (from immune cells). Interferon-β (IFN-β) exhibits various biological and immunological activities and as a result has potential applications in immunotherapy, antitumor, anticancer and antiviral therapies. Numerous investigations and clinical trials have been and are being conducted based on anticancer and antiviral properties of both wild-type and recombinant IFN-β. Clinical trials using recombinant IFN-β in the treatment of multiple sclerosis also have been conducted.

Most cytokines, including native IFN-β, have relatively short circulating half-lives. Consequently, in order for IFN-β to be effective as a therapeutic agent, it must be administered in large and frequent doses to a patient; however, this often leads to toxic side effects. Therefore, it is highly desirable to produce forms of IFNβ that have prolonged circulating half-lives compared to the native cytokine. Furthermore, for production purposes it is useful to produce forms of IFN-β that are easy to express and purify in large amounts.

Human IFN-β (huIFN-β) is a glycoprotein of 166 amino acids and has a four helix-bundle structure. Recombinant huIFN-β may be commonly produced for use as a therapeutic in either a prokaryotic or a mammalian expression system. However, when proteins that are normally secreted, such as huIFN-β, in a mammalian environment are produced in a prokaryote, the effect of prokaryotic expression on protein folding and on potential post-translational modifications needs to be addressed. For example, in mammalian cells, most proteins destined for the extracellular milieu are folded in the oxidizing environment of the endoplasmic reticulum (ER), which promotes the correct formation of disulfide bonds. In contrast, the reducing environment of the prokaryotic cytosol interferes with the formation of cysteine bonds. In addition, proteins expressed in prokaryotic systems lack some post-translational modifications, such as N-linked glycosylation, which likely aid in the correct folding of the protein, increase the stability of the folded protein, and decrease the immunogenicity of the administered protein.

For example, when intact wild-type IFN-β is expressed in a prokaryotic expression system, it does not fold properly and forms aggregates. This can be overcome by mutating the free cysteine at position 17 of the mature IFN-β protein to, for example, a serine. This cysteine at position 17 is not involved in a disulfide bond. See, for example, U.S. Pat. No. 4,737,462. In contrast, when intact wild-type IFN-β is produced in a eukaryotic expression system, where the environment is appropriate for correct folding of the IFN-β protein, improper folding and aggregation are not observed. Because IFN-β protein appears to fold properly and not to aggregate when expressed in a eukaryotic expression system, this suggests that glycosylation plays an important role in proper folding of the IFN-β protein. Recombinant IFN-β produced in a eukaryotic expression system undergoes glycosylation, although it may not have the precise glycosylation pattern of the native IFN-β. See, for example, U.S. Pat. No. 5,795,779. Whereas glycosylation of IFN-β does not seem to be essential for its biological activity, the specific activity of glycosylated IFN-β in bioassays is greater than that of the unglycosylated form. Indeed, IFN-β produced in a eukaryotic expression system, such as a mammalian expression system, is substantially non-aggregated, but does form aggregates when the glycan moiety is removed. Therefore, the glycosylated form of IFN-β is desirable for therapeutic use as its biophysical properties are closer to those of the native protein than the unglycosylated form.

In addition, it has been found that linking a protein of interest "X" to an immunoglobulin Fc domain "Fc" to create an Fc-X fusion protein ("immunofusin") generally has the effect of increasing protein production significantly. This is believed to occur, in part, because the Fc moiety of the fusion protein, commonly referred to as the expression cassette, is designed for efficient secretion of the fusion protein, and in part because proteins are being produced and secreted from mammalian cells that are normally active for secretion. A further advantage of creating Fc-X fusion proteins is that the resultant immunofusins exhibit an increased circulating half-life as compared to the free proteins of interest, which can be a significant therapeutic advantage.

There is, therefore, a need in the art for biologically active immunofusins including an Fc moiety fused to an IFN-β moiety optimized to have biophysical properties that are close to those of native IFN-β.

SUMMARY OF THE INVENTION

The invention provides methods and compositions for expressing soluble, biologically active Fc-IFN-β fusion proteins and variants thereof (Fc-IFN-$\beta^{sol}$). The Fc-IFN-$\beta^{sol}$ fusion proteins of the invention demonstrate improved biological properties over unaltered Fc-IFN-β proteins such as increased solubility, prolonged circulating half-life, enhanced biological activity, and reduced immunogenicity.

To improve the circulating half-life of IFN-β, the invention provides a fusion protein including an Fc-IFN-β fusion protein including an immunoglobulin Fc region and an IFN-β protein linked to the carboxy-terminus of the immunoglobulin Fc region. To improve folding and to reduce aggregation, the IFN-β protein includes an amino acid alteration at at least one of positions 17, 50, 57, 130, 131, 136, and 140, corresponding to native mature interferon-β. The alteration to the amino acid can be a deletion, substitution or modification. In one embodiment, the amino acid alteration substitutes either serine, alanine, valine or methionine in place of cysteine at position 17. In another embodiment, the amino acid alteration substitutes histidine in place of phenylalanine at position 50.

In yet another embodiment, the amino acid alteration substitutes alanine in place of leucine at position 57, while in a further embodiment, the amino acid alteration substitutes alanine in place of leucine at position 130. A further embodiment allows an amino acid alteration substituting alanine in place of histidine at position 131, while an additional embodiment contemplates substituting alanine in place of lysine at position 136. In yet another embodiment, the amino acid alteration substitutes alanine or threonine in place of histidine at position 140.

The immunoglobulin Fc region can include an immunoglobulin hinge region and an immunoglobulin heavy chain constant region. In one embodiment, the Fc region is derived from IgG4, while in another it is derived from IgG1, and in yet another it is derived from IgG2. In another embodiment, the Fc region is derived from IgG4 but includes a hinge region from IgG1. In yet another embodiment, the Fc region is derived from IgG2 but includes a hinge region derived from IgG1. When the Fc region includes a CH3 domain, the C-terminal lysine of the immunoglobulin Fc region can be replaced by an alanine residue. In a further embodiment, a cysteine residue of the hinge region is mutated.

The invention provides different methods for joining the Fc moiety and the IFN-β moiety to create fusion proteins according to the invention. For example, in one embodiment the immunoglobulin Fc region and the interferon-β protein are fused together by a peptide bond. In another embodiment, the immunoglobulin Fc region and the interferon-β protein are connected by a peptide linker sequence to facilitate protein folding. The linker sequence preferably is composed of glycine and serine residues. For example, in one embodiment, the peptide linker sequence is $Gly_4SerGly_4SerGly_3SerGly$ (SEQ ID NO:1).

In one embodiment, the Fc-interferon-β fusion protein includes amino acid alterations at positions 17, 50, 131, and 140 to improve folding and reduce aggregation. In one specific embodiment, the amino acid alterations are serine substituted in place of cysteine at position 17, histidine substituted in place of phenylalanine at position 50, alanine substituted in place of histidine at position 131, and threonine or alanine substituted in place of histidine at position 140. In certain embodiments, the Fc region includes IgG1, IgG2, or IgG4. The fusion protein can also include a polypeptide linker sequence connecting the interferon-β protein and the immunoglobulin Fc region. In one embodiment, a cysteine residue of the hinge region is mutated.

In another embodiment, the Fc-interferon-β fusion protein includes amino acid alterations at positions 17, 57, 131, and 140, improving folding and reducing aggregation of the expressed fusion protein. In one specific embodiment, the amino acid alterations are serine substituted in place of cysteine at position 17, alanine substituted in place of leucine at position 57, alanine substituted in place of histidine at position 131, and threonine or alanine substituted in place of histidine at position 140. In certain embodiments, the Fc region includes IgG1, IgG2, or IgG4. In another embodiment, the fusion protein can also include a polypeptide linker sequence connecting the interferon-β protein and the immunoglobulin Fc region. In a further embodiment, a cysteine residue of the hinge region is mutated.

The invention also provides methods for encoding and expressing fusion proteins of the invention. For example, one aspect of the invention relates to nucleic acid molecules encoding any of the aforementioned Fc-interferon-β fusion proteins, while in another aspect, the invention relates to cells containing a nucleic acid encoding any of the aforementioned Fc-interferon-β fusion proteins. In a further aspect, the nucleic acid molecules of the invention can be incorporated in operative association into a replicable expression vector which can then be introduced, for example, by transfection, into a mammalian host cell competent to produce the immunoglobulin Fc-IFN-$\beta^{sol}$ fusion protein. The vector includes a nucleic acid molecule encoding any one of the aforementioned Fc-interferon-β fusion proteins. The invention also encompasses a replicable expression vector for transfecting a mammalian cell. The vector includes a nucleic acid molecule encoding any one of the aforementioned Fc-interferon-β fusion proteins.

In another aspect, the invention relates to methods of stabilizing Fc-interferon-β fusion proteins. In one embodiment, the method includes the step of making any of the aforementioned Fc-interferon-β fusion proteins. In a further embodiment, the stabilizing includes increasing the circulating half-life of the Fc-interferon-β fusion protein relative to an unaltered Fc-interferon-β fusion protein. In yet another embodiment, the stabilizing includes decreasing the aggregation of the Fc-interferon-β fusion protein relative to an unaltered Fc-interferon-β fusion protein, while in a further embodiment, the stabilizing includes increasing the biological activity of the Fc-interferon-β fusion protein relative to an unaltered Fc-interferon-β fusion protein.

A further aspect of the invention relates to methods for treating a patient for a condition alleviated by the administration of interferon-β. In one embodiment, the treatment includes administering an effective amount of any of the aforementioned interferon-β fusion proteins to a mammal having the condition. In another embodiment, the method includes administering a nucleic acid encoding any of the aforementioned interferon-β fusion proteins to a mammal having the condition, while in yet another embodiment, the method includes administering a cell encoding any of the aforementioned interferon-β fusion proteins to a mammal having the condition.

The foregoing and other objects, features and advantages of the invention will be apparent from the description, drawings, and claims that follow.

BRIEF DESCRIPTION OF THE DRAWINGS

FIG. 3 is the amino acid sequence for mature IFN-β (SEQ ID NO:2).

FIG. 4 is the amino acid sequence for mature human IFN-β(C17S) (SEQ ID NO:3).

FIG. 5 is the amino acid sequence for human Fc-IFN-$\beta^{sol}$(C17S) of the γ4 isotype with a modified γ1 hinge (Fcγ4h-IFN-$\beta^{sol}$) (SEQ ID NO:4).

FIG. 6 is the amino acid sequence for human Fc-(linker)-IFN-β, starting with the CH3 domain of the Fcγ4 isotype (SEQ ID NO:5).

FIG. 7 is the amino acid sequence for human Fc-linker)-IFN-$\beta^{sol}$(C17S), starting with the CH3 domain of the Fcγ4 isotype (SEQ ID NO:6).

FIG. 8 is the amino acid sequence for human Fc-(linker)-IFN-$\beta^{sol}$(C17S L57A H131A H140T) starting with the CH3 domain of the Fcγ4 isotype (SEQ ID NO:7).

FIG. 9 is the amino acid sequence for human Fc-(linker)-IFN-$\beta^{sol}$(C17S L57A H131A H140A) starting with the CH3 domain of the Fcγ4 isotype (SEQ ID NO:8).

FIG. 10 is the amino acid sequence for human Fc-(linker)-IFN-$\beta^{sol}$(C17S F50A H131A, H140A), starting with the CH3 domain of the Fcγ4 isotype (SEQ ID NO:9).

FIG. 11 is the amino acid sequence for human Fc-(linker)-IFN-$\beta^{sol}$(C17S F50A H131A H140T), starting with the CH3 domain of the Fcγ4 isotype (SEQ ID NO:10).

FIG. 12 is the amino acid sequence for mature mouse IFN-β (SEQ ID NO:11).

FIG. 13 is the amino acid sequence for mature mouse IFN-β(C17S) (SEQ ID NO:12).

FIG. 14 is the nucleic acid sequence encoding the fusion protein embodiment huFcγ4h-IFN-$\beta^{sol}$(C17S) (γ4 isotype with modified γ1 hinge wherein the first cysteine of the γ1 hinge is replaced by a serine), starting from the hinge region (SEQ ID NO:13).

FIGS. 15-1 through 15-3 show the linearized nucleic acid sequence of the pdCs vector containing huFcγ4h-(linker)-IFN-$\beta^{sol}$(C17S) (γ4 isotype with modified γ1 hinge wherein the first cysteine of the γ1 hinge is replaced by a serine), wherein the Fc region and the IFN-β moiety are attached via a linker polypeptide (SEQ ID NO:14).

FIG. 16 is the nucleic acid sequence encoding the fusion protein embodiment HuFc-γ4h-(linker)-IFN-$\beta^{sol}$(C17S) (γ4 isotype with modified γ1 hinge wherein the first cysteine of the γ1 hinge is replaced by a serine), starting from the hinge region, wherein the Fc region and the IFN-β moiety are attached via a linker polypeptide (SEQ ID NO:15).

FIGS. 17-1 through 17-3 show the linearized nucleic acid sequence of the pdCs vector containing huFcγ4h-(linker)-IFN-$\beta^{sol}$(C17S L57A H131A H140A) (γ4 isotype with modified γ1 hinge wherein the first cysteine of the γ1 hinge is replaced by a serine), wherein the Fe region and the IFN-β moiety are attached via a linker polypeptide (SEQ ID NO:16).

FIG. 18 is the nucleic acid sequence of huFcγ4h-(linker)-IFN-$\beta^{sol}$(C17S L57A H131 H140A) (γ4 isotype with modified γ1 hinge wherein the first cysteine of the γ1 hinge is replaced by a serine), starting from the hinge, wherein the Fe region and the IFN-β moiety are attached via a linker polypeptide (SEQ ID NO:17).

FIG. 19-1 through 19-3 shows the linearized nucleic acid sequence of the pdCs vector containing huFcγ4h-(linker)-IFN-$\beta^{sol}$(C17S F50H H131A H140A) (γ4 isotype with modified γ1 hinge wherein the first cysteine of the γ1 hinge is replaced by a serine), wherein the Fc region and the IFN-β moiety are attached via a linker polypeptide (SEQ ID NO:18).

FIG. 20 is the nucleic acid sequence of huFcγ4h-(linker)-IFN-$\beta^{sol}$(C17S F50H H131A H140A) (γ4 isotype with modified γ1 hinge wherein the first cysteine of the γ1 hinge is replaced by a serine) starting from the hinge, wherein the Fc region and the IFN-β moiety are attached via a linker polypeptide (SEQ ID NO:19).

DETAILED DESCRIPTION OF THE INVENTION

Figure 1A:
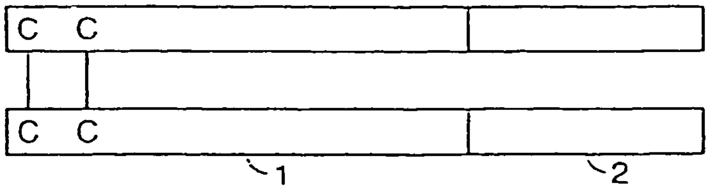
FIGS. 1A-1C are schematic illustrations of non-limiting examples of Fc-IFN-$\beta^{sol}$ fusion proteins constructed in accordance with the invention.

IFN-β mediates antiproliferative, antiviral and immunomodulatory effects and, in addition to its usefulness in treating multiple sclerosis, it is anticipated that many other conditions may be alleviated by IFN-β administration. For example, its usefulness as a treatment for a variety of malignancies, such as acute myeloid leukemia, multiple myeloma, Hodgkin's disease, basal cell carcinoma, cervical dysplasia and osteosarcoma is under evaluation. IFN-β is also being tested as a therapeutic agent against a variety of viral infections, including viral hepatitis, herpes zoster and genitalis, papilloma viruses, viral encephalitis, and cytomegalovirus pneumonia.

However, when administered to a patient, recombinant mature IFN-β has a short circulating half-life, making it suboptimal for use in therapy. Therefore there is a need in the art to produce variants of IFN-β with improved pharmacokinetic properties, including improved serum half-life.

One method known in the art for prolonging the half-life of small proteins involves linking them to an immunoglobulin Fc region. Fusions in which an Fc region is placed at the N-terminus of a ligand (termed 'immunofusins' or 'Fc-X' fusions, where X is a ligand such as IFN-β) have a number of useful properties (Lo et al., U.S. Pat. Nos. 5,726,044 and 5,541,087; Lo et al. (1998) Protein Engineering 11: 495). For instance, if leptin is administered to a mouse as an Fc-leptin fusion molecule (See, for example, PCT patent application publication WO 00/40615), the circulating half-life of leptin increases from about 18 minutes to more than 8 hours. Similarly, the half-life of IL-2 in a mouse is increased from a few minutes to a few hours when it is administered as an Fc-IL2 fusion protein.

Another useful property of Fc-X fusion proteins is that the Fc portion generally has the effect of increasing protein production significantly. This is believed to occur, in part, because the Fc moiety of the fusion protein, commonly referred to as the expression cassette, is designed for efficient secretion of the fusion protein and, in part, because the fusion proteins can be produced in and secreted from host mammalian cells that naturally express immunoglobulin such that the fusion protein is readily secreted from the host cell. While it may be possible to produce these fusion proteins in a prokaryotic expression system, a eukaryotic expression system is preferred and a mammalian expression system is most preferred.

Surprisingly, it was found that when an unaltered Fc-IFN-β immunofusin was produced in a eukaryotic expression system, it was poorly expressed, misfolded and substantially aggregated. In contrast, recombinant IFN-β proteins produced in a eukaryotic expression system are soluble and 98% monomeric (Runkel et al. (1998), Pharmaceutical Research 15:641). Thus it appeared that the placement of the Fc moiety at the N-terminus of the IFN-β moiety affected the ability of the fusion protein to fold correctly as no aggregation is observed when IFN-β is produced as a fusion protein where the IFN-β moiety precedes the Fc domain (See U.S. Pat. No. 5,908,626). Therefore, there is a need in the art to create Fc-IFN-β fusion proteins that fold correctly and are substantially non-aggregated.

Consequently, the invention provides (i) nucleic acid sequences which facilitate efficient production of immunoglobulin Fc-IFN-$\beta^{sol}$ fusion proteins; (ii) nucleic acid constructs for rapid and efficient production and secretion of immunoglobulin Fc-IFN-$\beta^{sol}$ fusion proteins in a variety of mammalian host cells; and (iii) methods for the production, secretion, and purification of recombinant variants of immunoglobulin Fc-IFN-$\beta^{sol}$ fusion proteins.

In particular, the present invention provides nucleic acid molecules, for example, DNA or RNA molecules, which encode serially in the 5' to 3' direction, a polypeptide including an immunoglobulin Fc region and an IFN-$\beta^{sol}$ protein.

The nucleic acid molecules of the invention can be incorporated in operative association into a replicable expression vector which may then be introduced, for example, by transfection, into a mammalian host cell competent to produce the immunoglobulin Fc-IFN-$\beta^{sol}$ fusion protein.

The invention also provides methods of stabilizing immunoglobulin Fc-IFN-β fusion proteins. Although many proteins have been successfully produced and purified as Fc fusions, including many four-helix bundle proteins such as IL-2 (huFc-IL2), it has been found that Fc-IFN-β fusion proteins, where IFN-β belongs to the class of four-helix bundle proteins, form aggregates at least partly due to aberrant disulfide bonds present in the protein ("covalent aggregation"). In addition, it has been found that Fc-IFN-β proteins form aggregates through non-covalent interactions as well ("non-covalent aggregation").

The present invention alleviates aggregation by providing methods of stabilizing Fc-IFN-β fusion proteins including the step of making an Fc-IFN-$\beta^{sol}$ fusion protein, where the fusion protein includes an IFN-β protein having at one or more amino acid alterations, linked to the carboxy-terminus of an immunoglobulin Fc region. In embodiments of the invention, stabilizing includes increasing the solubility of the Fc-IFN-$\beta^{sol}$ fusion protein relative to an unaltered Fc-IFN-β fusion protein, increasing the circulating half-life of the Fc-IFN-$\beta^{sol}$ fusion protein relative to an unaltered Fc-IFN-β fusion protein, and/or enhancing the biological activity of the Fc-IFN-$\beta^{sol}$ fusion protein relative to an unaltered Fc-IFN-β fusion protein. Increased stabilization is achieved in part by the elimination of aberrant disulfide bonding in the fusion protein and in part by reducing the amount of non-covalent aggregation of the fusion protein.

The invention also provides methods for treating conditions alleviated by IFN-β, bioactive fragments or active variants thereof by administering to a mammal an effective amount of IFN-β produced by a method of the invention and/or an Fc-IFN-$\beta^{sol}$ fusion protein of the invention. The invention also provides methods for treating conditions alleviated by IFN-β or active variants thereof by administering a nucleic acid of the invention, for example, a "naked DNA," or a vector containing a DNA or RNA of the invention, to a mammal having the condition.

IFN-β Moiety

The invention provides fusion proteins and nucleic acid molecules encoding those proteins including an altered IFN-β protein linked to the C-terminus of an immunoglobulin Fc region. The IFN-β moiety can include one ore more mutations to the amino acid structure of the IFN-β moiety and Fc-IFN-β construct to improve the protein folding properties of the fusion protein, to reduce aggregation, and to improve protein expression. For example, the IFN-β moiety of the soluble fusion protein Fc-IFN-$\beta^{sol}$ can contain an alteration at position 17, corresponding to a cysteine in the native mature IFN-β linked to the carboxy-terminus of an immunoglobulin Fc region. The amino acid sequence for native mature human IFN-β is shown in FIG. 3. The amino acid alteration at position 17 of the IFN-β protein can be generated by an amino acid substitution, amino acid deletion or amino acid modification through methods known in the art. Preferred alterations to the IFN-β moiety include substituting either a serine (C17S), valine (C17V), alanine (C17A) or methionine (C17M) in place of the cysteine at position 17. An exemplary amino acid sequence of a soluble human Fc-IFN-β fusion protein containing the C17S mutation (huFc-IFN-$\beta^{sol}$ (C17S)) is shown in FIG. 5 (SEQ ID NO:4), while the amino acid sequence for an IFN-β moiety including the C17S mutation is shown in FIG. 4 (SEQ ID NO:3). The invention also includes huFc-IFN-$\beta^{sol}$(C17V), huFc-IFN-βsol(C17A) and huFc-IFN-$\beta^{sol}$(C17M) fusion protein constructs.

In addition to an alteration at position 17 of the mature IFN-β moiety, the invention provides Fc-IFN-β fusion proteins with other altered residues. For example, the IFN-β moiety can be altered at one or more of positions 17, 50, 57, 130, 131, 136, and 140 corresponding to, respectively, a cysteine, a phenylalanine, a lysine, a leucine, a histidine, a lysine, and a histidine in the native mature IFN-β protein. The IFN-β moiety is linked to the carboxy-terminus of an immunoglobulin Fc region. Alterations to the amino acid structure at one or more of positions 17, 50, 57, 130, 131, 136, and 140 can include an amino acid substitution, amino acid deletion or amino acid modification and can be generated through methods known in the art. Alterations introduced at these residues are believed to alleviate the causes of non-covalent aggregation. In one embodiment, the phenylalanine at position 50 is replaced by histidine (F50H). In another embodiment, the leucine at position 57 is replaced by alanine (L57A). In a further embodiment, the histidine at position 131 is replaced by alanine (H131A), while in yet another embodiment, the histidine at 140 is replaced by either alanine (H140A) or threonine (H140T). In another embodiment, the leucine at position 130 is replaced by alanine (L130A), while in yet another embodiment, the lysine at residue 136 is replaced by alanine (K136A). While certain amino acid substitutions have been enumerated herein, the invention is not limited to these enumerated alterations. Any suitable amino acid capable of conferring the appropriate properties on the fusion protein may be substituted in place of the original amino acid residue at position 17, 50, 57, 130, 131, 136, and/or 140 of the IFN-β moiety.

The invention contemplates an IFN-β moiety of an Fc-IFN-$\beta^{sol}$ fusion protein having any combination of one, two, three, four, five, six, or seven of the alterations to positions 17, 50, 57, 130, 131, 136 and/or 140 as disclosed herein. For example, the Fc-IFN-$\beta^{sol}$ in one embodiment contains amino acid alterations at one or more of F50, H131 and H140 of the mature form of IFN-β, optionally combined with a C17 alteration. In another embodiment, the IFN-β moiety of the Fc-IFN-$\beta^{sol}$ fusion protein contains amino acid alterations at one or more of L57, H131 and H140 of the mature form of IFN-β, optionally combined with a C17 alteration. In another embodiment, IFN-β moiety of the Fc-IFN-$\beta^{sol}$ fusion protein includes the alterations C17S, F50H, H131A, and/or H140A. FIGS. 8-11 show exemplary amino acid sequences of embodiments of Fc-IFN-$\beta^{sol}$ fusion proteins incorporating various combinations of these mutations. In yet another embodiment, the IFN-β moiety of the Fc-IFN-$\beta^{sol}$ fusion protein includes the alterations C17S, F50H, H131A, and/or H140T. In yet another embodiment, the IFN-β moiety of the Fc-IFN-$\beta^{sol}$ fusion protein includes the alterations C17S, L57A, H131A, and/or H140A, while in a further embodiment, the fusion protein includes the alterations C17S, L57A, H131A, and/or H140T. The Fc region is preferably a human Fc region.

Another embodiment of the invention includes nucleic acid sequences encoding Fc-IFN-$\beta^{sol}$ variants with at least one codon substitution in the mature human IFN-β protein sequence. In one embodiment, a codon substitution replaces the cysteine corresponding to position 17 in the mature human IFN-β sequence with a serine (C17S). Expression of this nucleotide sequence, contained on an appropriate plasmid, in a mammalian cell culture system resulted in the efficient production of the fusion protein huFc-huIFN-$\beta^{sol}$ (C17S). In alternative embodiments, a codon substitution replaces the cysteine at position 17 with either an alanine, a valine, or a methionine. Similarly, expression from any of these nucleotide sequences, contained on an appropriate plasmid, in a mammalian cell culture system will result in the efficient production of fusion protein huFc-huIFN-$\beta^{sol}$ (C17A), huFc-huIFN-$\beta^{sol}$(C17V), or huFc-huIFN-$\beta^{sol}$ (C17M). In one embodiment, a nucleic acid sequence encoding a representative Fc-IFN-$\beta^{sol}$ fusion protein huFcγ4h-IFN-$\beta^{sol}$(C17S), starting from the hinge, is disclosed in FIG. 14 (SEQ ID NO:13). The invention also includes nucleic acid sequences encoding Fc-IFN-$\beta^{sol}$ variants with codon substitutions replacing amino acids at one or more of positions 17, 50, 57, 130, 131, 136 and/or 140. Nucleic acids incorporating the altered codons of the invention can be created using methods known in the art.

The immunoglobulin Fc region and the IFN-β moiety of an Fc-IFN-$\beta^{sol}$ fusion protein can be linked to one another in a variety of ways. While the C-terminus of the Fc moiety may be directly linked to the N-terminus of the IFN-β moiety via a peptide bond, the invention additionally includes connecting the Fc moiety and the IFN-β moiety via a linker peptide. The linker peptide is located between the C-terminus of the Fc moiety and the N-terminus of the mature IFN-β moiety. The invention also includes a nucleic acid sequence encoding the linker peptide. The linker peptide is preferably composed of serine and glycine residues. In one embodiment, the linker has the amino acid sequence $Gly_4SerGly_4SerGly_3SerGly$ (SEQ ID NO:1), while in yet another embodiment a nucleic acid encoding an Fc-IFN-$\beta^{sol}$ includes a nucleic acid sequence encoding the linker peptide $Gly_4SerGly_4SerGly_3SerGly$ (SEQ ID NO:1). Some exemplary Fc-linker-IFN-$\beta^{sol}$ amino acid sequences of the invention are shown in FIGS. 6-11, while some exemplary Fc-linker-IFN-$\beta^{sol}$ nucleic acid sequences of the invention are shown in FIGS. 14-16. For example, in one embodiment, the Fc-linker-IFN-$\beta^{sol}$ protein is huFcγ4-linker-IFN-$\beta^{sol}$(C17S), wherein the Fc region is an IgG4 Fc region, and the linker is $Gly_4SerGly_4SerGly_3SerGly$ (SEQ ID NO:1). Expression of fusion proteins of the invention from Fc-IFN-$\beta^{sol}$ and Fc-linker-IFN-$\beta^{sol}$ nucleotide sequences, such as those previously discussed, when contained on an appropriate plasmid, in a mammalian cell culture system will result in the efficient production of Fc-IFN-$\beta^{sol}$ and Fc-linker-IFN-$\beta^{sol}$ fusion proteins.

As previously mentioned, Fc-IFN-$\beta^{sol}$ fusion proteins of the invention demonstrate improved biological properties over unaltered Fc-IFN-β fusion proteins. For example, it was found that human Fcγ4h-IFN-$\beta^{sol}$(C17S) displayed folding properties that were different from, and improved over, the parent fusion protein Fcγ4-IFN-$\beta^{sol}$ and Fc-γ4h-IFN-$\beta^{sol}$. In particular, as demonstrated in FIG. 2, it was found that predominantly a single species of the human Fcγ4h-IFN-$\beta^{sol}$ (C17S) fusion protein 3, 4 was seen when expressed in mammalian tissue culture cells, as ascertained by non-reducing SDS-PAGE gel analysis. This species corresponded to the correctly folded Fcγ4-IFN-$\beta^{sol}$ fusion protein 3, 4. In contrast, for the parent molecule Fcγ4-IFN-$\beta^{sol}$ 1 and for Fcγ4h-IFN-$\beta^{sol}$ 2, many high molecular weight species were observed, as evidenced by an unresolved trail of high molecular weight proteins on a non-reducing SDS-PAGE gel 1, 2. On a reducing SDS-PAGE gel system, this trail resolved to a significant extent into a single band for both human Fcγ4-IFN-$\beta^{sol}$ 5 and human Fcγ4h-IFN-$\beta^{sol}$ 6, suggesting that the aggregation was largely driven by the presence of covalent disulfide bonds. Therefore, the introduction of the single point mutation C17S into the human Fcγ4h-IFN-$\beta^{sol}$ fusion protein 7 restored proper folding of the protein 7.

Moreover, it was found by analytical size exclusion chromatography (SEC), that, whereas non-aggregated protein of the parent molecule could not be obtained, at least 10% of Fc-IFN-$\beta^{sol}$(C17S) was non-aggregated after purification with Protein A. Therefore, the introduction of the single point mutation C17S into the Fc-IFN-$\beta^{sol}$ fusion protein facilitated the production of non-aggregated material. Furthermore, introduction of a linker peptide at the junction between the Fc region and the IFN-β moiety resulted in about a two-fold increase in yield of non-aggregated material over Fc-IFN-$\beta^{sol}$ (C17S) without the linker. Expression from, for example, a nucleotide sequence encoding the fusion protein Fc-linker-IFN-$\beta^{sol}$(C17S F50H H131A H140A) wherein the linker is $Gly_4SerGly_4SerGly_3SerGly$ (SEQ ID NO:1), as shown in FIGS. 19-1 through 19-3, contained on an appropriate plasmid, in a mammalian cell culture system resulted in the efficient production of the fusion protein Fc-linker-IFN-$\beta^{sol}$ (C17S F50H H131A H140A). It was found that this fusion protein product contained about 50% non-aggregated material after purification by Protein A, as assessed by analytical SEC, which represents a considerable further improvement over the results obtained with Fc-IFN-$\beta^{sol}$ protein containing a single point mutation in IFN-β, Fc-linker-IFN-$\beta^{sol}$(C17S). A similar further increase in expression characteristics was seen with the Fc-IFN-$\beta^{sol}$ protein Fc-linker-IFN-$\beta^{sol}$(C17S L57A H131A H140T).

As previously mentioned, the invention provides nucleic acid sequences encoding and amino acid sequences defining fusion proteins including an immunoglobulin Fc region and at least one target protein, referred to herein as IFN-β or variants thereof. Three exemplary embodiments of protein constructs embodying the invention are illustrated in the drawing as FIGS. 1A-1C. Because dimeric constructs are preferred, all are illustrated as dimers cross-linked by a pair of disulfide bonds between cysteines in adjacent subunits. In the drawings, the disulfide bonds 11, 12 are depicted as linking together the two immunoglobulin heavy chain Fc regions 1, 1' via an immunoglobulin hinge region within each heavy chain, and thus are characteristic of native forms of these molecules. While constructs including the hinge region of Fc are preferred and have shown promise as therapeutic agents, the invention contemplates that the crosslinking at other positions may be chosen as desired. Furthermore, under some circumstances, dimers or multimers useful in the practice of the invention may be produced by non-covalent association, for example, by hydrophobic interaction. Because homodimeric constructs are important embodiments of the invention, the drawings illustrate such constructs. It should be appreciated, however, that heterodimeric structures also are useful in the practice of the invention.

FIG. 1A illustrates a dimeric construct, also termed a "unit dimer", produced in accordance with the principles set forth herein (see, for example, Example 1). Each monomer of the homodimer includes an immunoglobulin Fc region I including a hinge region, a CH2 domain and a CH3 domain. Attached directly, i.e., via a polypeptide bond, to the C terminus of the Fc region is IFN-$\beta^{sol}$ 2. It should be understood that the Fc region may be attached to IFN-$\beta^{sol}$ protein via a polypeptide linker (not shown).

Figure 1B:
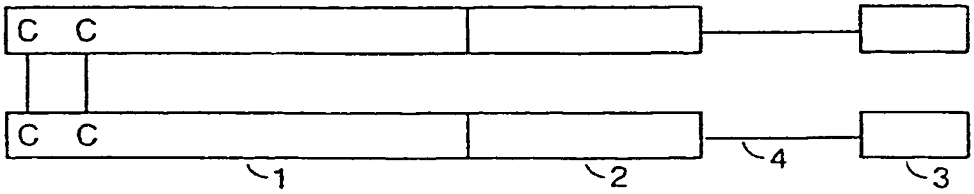
Figure 1C:
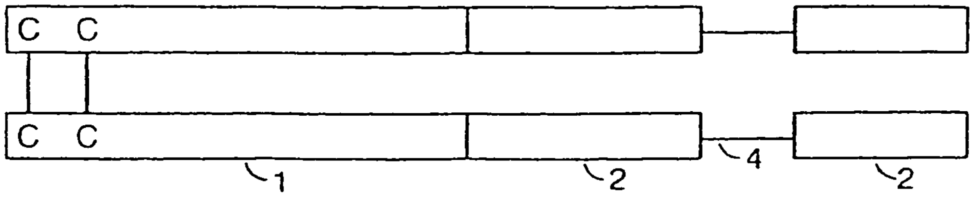

FIGS. 1B and 1C depict protein constructs of the invention which include as a target protein plural IFN-β proteins arranged in tandem and connected by a linker. In FIG. 1B, the target protein includes full length IFN-β 2, a polypeptide linker made of glycine and serine residues 4, and an active variant of IFN-β 3. This construct may be depicted by the formula Fc-X-X wherein the Xs represent different target proteins. FIG. 1C differs from the construct of FIG. 1B in that the most C-terminal protein domain includes a second, full length copy of IFN-β 2. This construct may be depicted by the formula Fc-X-X, where the Xs represent identical target proteins. Although FIGS. 1A-1C represent Fc-X constructs, where X is the target protein, it is contemplated that useful proteins of the invention may also be depicted by the formula X-Fc-X, wherein the Xs may represent the same or different target proteins.

As shown in FIGS. 1B and 1C, the fusion protein may include a second target protein (Fc-X-X). For example, in addition to a fusion protein having a first IFN-β target protein, the fusion protein may also include a second mature, full length IFN-β or an active IFN-$\beta^{sol}$ variant or a bioactive fragment thereof. In one aspect, the active variant is a variant in which one or more amino acid residues in the IFN-β moiety is substituted for another amino acid residue. Several IFN-β substitution variants were discussed previously. For example, a cysteine at position 17, corresponding to the native mature IFN-β may be replaced with a serine, a valine, an alanine or a methionine. In this type of construct, the first and second proteins can be the same protein, as in, for example, FIG. 1C, or they may be different proteins, as in, for example, FIG. 1B. The first and second proteins may be linked together, either directly or by means of a polypeptide linker. Alternatively, both proteins may be linked either directly or via a polypeptide linker, to the immunoglobulin Fc region. In a further embodiment, the first protein can be connected to the N-terminus of the immunoglobulin Fc region and the second protein can be connected to the C-terminus of the immunoglobulin Fc region.

In one embodiment, two fusion proteins may be linked to form dimers. The two fusion proteins may associate, either covalently, for example, by a disulfide bond, a polypeptide bond or a crosslinking agent, or non-covalently, to produce a dimeric protein. In a preferred embodiment, the two fusion proteins are associated covalently by means of at least one and more preferably two interchain disulfide bonds via cysteine residues, preferably located within immunoglobulin hinge regions disposed within the immunoglobulin Fc regions of each chain.

Other embodiments of the invention include multivalent and multimeric forms of IFN-β fusion proteins and combinations thereof.

As used herein, the term "multivalent" refers to a recombinant molecule that incorporates two or more biologically active segments. The protein fragments forming the multivalent molecule optionally may be linked through a polypeptide linker which attaches the constituent parts and permits each to function independently.

As used herein, the term "bivalent" refers to a multivalent recombinant molecule having the configuration Fc-X, where X is an IFN-β protein. The two proteins may be linked through a peptide linker. Constructs of the type shown can increase the apparent binding affinity between the protein and its receptor.

As used herein, the term "multimeric" refers to the stable association of two or more polypeptide chains either covalently, for example, by means of a covalent interaction, for example, a disulfide bond, or non-covalently, for example, by hydrophobic interaction. The term multimer is intended to encompass both homomultimers, wherein the subunits are the same, as well as, heteromultimers, wherein the subunits are different.

As used herein, the term "dimeric" refers to a specific multimeric molecule where two polypeptide chains are stably associated through covalent or non-covalent interactions. Such constructions are shown schematically in FIG. 1A. It should be understood that the immunoglobulin Fc region including at least a portion of the hinge region, a CH2 domain and a CH3 domain, typically forms a dimer. Many protein ligands are known to bind to their receptors as a dimer. If a protein ligand X dimerizes naturally, the X moiety in an Fc-X molecule will dimerize to a much greater extent, since the dimerization process is concentration dependent. The physical proximity of the two X moieties connected by Fc would make the dimerization an intramolecular process, greatly shifting the equilibrium in favor of the dimer and enhancing its binding to the receptor.

As used herein, the term "polypeptide linker" is understood to mean a polypeptide sequence that can link together two proteins that in nature are not naturally linked together. The polypeptide linker preferably includes a plurality of amino acids such as alanine, glycine and serine or combinations of such amino acids. Preferably, the polypeptide linker includes a series of glycine and serine peptides about 10-15 residues in length. See, for example, U.S. Pat. Nos. 5,258,698 and 5,908,626. A preferred linker polypeptide of the invention is $Gly_4SerGly_4SerGly_3SerGly$ (SEQ ID NO:1). However, it is contemplated, that the optimal linker length and amino acid composition may be determined by routine experimentation by methods well known in the art.

As used herein, the term "interferon-β or IFN-β" is understood to mean not only full length mature interferon-β, for example, human IFN-β, but also homologs, variants and bioactive fragments or portions thereof. Known sequences of IFN-β may be found in GenBank. The term "interferon-β" or "IFN-β" also includes naturally occurring IFN-β and IFN-β-like proteins, moieties and molecules as well as IFN-β that is recombinantly produced or artificially synthesized.

The term "bioactive fragment" or portion refers to any IFN-β protein fragment that has at least 5%, more preferably at least 10%, and most preferably at least 20% and optimally at least 30%, 40%, 50%, 60%, 70%, 80%, 90% or 100% of the biological activity of the template human IFN-β protein of SEQ ID NO:2, determined using the antiviral activity assay or cellular growth inhibition assays, as described in Examples 6 and 7. The term "variants" includes species and allelic variants, as well as other naturally occurring or non-naturally occurring variants, for example, generated by genetic engineering protocols, that are at least 70% similar or 60% identical, more preferably at least 75% similar or 65% identical, and most preferably at least 80% similar or 70% identical to the mature human IFN-β protein disclosed in SEQ ID NO:2.

In order to determine whether a candidate polypeptide has the requisite percentage similarity or identity to a reference polypeptide, the candidate amino acid sequence and the reference amino acid sequence are first aligned using the dynamic programming algorithm described in Smith and Waterman (1981) J. MOL. BIOL. 147:195-197, in combination with the BLOSUM62 substitution matrix described in FIG. 2 of Henikoff and Henikoff (1992), "Amino acid substitution matrices from protein blocks", PROC. NATL. ACAD. SCI. USA 89:10915-10919. For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pair-wise similarity score is zero; otherwise the pair-wise similarity score is 1.0. The raw similarity score is the sum of the pair-wise similarity scores of the aligned amino acids. The raw score then is normalized by dividing it by the number of amino acids in the smaller of the candidate or reference sequences. The normalized raw score is the percent similarity. Alternatively, to calculate a percent identity, the aligned amino acids of each sequence again are compared sequentially. If the amino acids are non-identical, the pair-wise identity score is zero; otherwise the pair-wise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

Variants may also include other IFN-β mutant proteins having IFN-β-like activity. Species and allelic variants, include, but are not limited to human and mouse IFN-β sequences. The human and mouse mature IFN-β proteins are depicted in SEQ ID NOs.:2 and 11, and in FIGS. 3 and 12 respectively.

Furthermore, the IFN-β sequence may include a portion or all of the consensus sequence set forth in SEQ ID NO:2, wherein the IFN-β has at least 5%, preferably at least 10%, more preferably at least 20%, 30% or 40%, most preferably at least 50%, and optimally 60%, 70%, 80%, 90% or 100% of the biological activity of the mature human IFN-β of SEQ ID NO:2, as determined using the antiviral activity assay or cellular growth inhibition assay of Examples 6 and 7.

The three-dimensional structure of IFN-β has been solved by X-ray crystallography (Karpusas et al, 1997, PNAS 94: 11813). Although in the crystallized state, IFN-β molecule is a dimer with a zinc ion at the dimer interface, it is thought that IFN-β need not be a dimer in order to be active. Structurally IFN-β contains an additional alpha-helical segment with respect to classical four helix bundle proteins, which is formed within the C-D loop, so that the canonical bundle structure is formed by helices A, B, C and E. Interestingly, the structure also reveals a portion of the glycan moiety which is coupled to amino acid N80 at the start of helix C and is ordered along a portion of the protein, most likely shielding some of the surface-exposed hydrophobic amino acid residues from solvent. Glycosylation of IFN-β has been shown to be important for the solubility and stability of the molecule, and this could explain the propensity of the non-glycosylated IFN-β molecule to aggregate. The free cysteine at position 17 in helix A appears proximal to the surface but buried, and, without wishing to be bound by theory, it is possible that scrambled disulfide bonds may in turn prevent the correct glycosylation of the protein.

Dimerization of a ligand can increase the apparent binding affinity between the ligand and its receptor. For instance, if one interferon-beta moiety of an Fc-interferon-beta fusion protein can bind to a receptor on a cell with a certain affinity, the second interferon-beta moiety of the same Fc-Interferon-beta fusion protein may bind to a second receptor on the same cell with a much higher avidity (apparent affinity). This may occur because of the physical proximity of the second interferon-beta moiety to the receptor after the first interferon-beta moiety already is bound. In the case of an antibody binding to an antigen, the apparent affinity may be increased by at least ten thousand-fold, i.e., 104. Each protein subunit, i.e., "X," has its own independent function so that in a multivalent molecule, the functions of the protein subunits may be additive or synergistic. Thus, fusion of the normally dimeric Fc molecule to interferon-beta may increase the activity of interferon-beta. Accordingly, constructs of the type shown in FIG. 1A may increase the apparent binding affinity between interferon-beta and its receptor.

Fc Moiety

The IFN-β fusion proteins disclosed herein are expressed as fusion proteins with an Fc region of an immunoglobulin. As is known, each immunoglobulin heavy chain constant region includes four or five domains. The domains are named sequentially as follows: CH1-hinge-CH2-CH3(—CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE.

As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may include 1) a CH2 domain 2) a CH3 domain, 3) a CH4 domain 4) a CH2 domain and a CH3 domain, 5) a CH2 domain and a CH4 domain, 6) a CH3 domain and a CH4 domain or 7) a combination of an immunoglobulin hinge region and/or a CH2 domain and/or CH3 domain and/or a CH4 domain. In one embodiment, the immunoglobulin Fc region includes at least an immunoglobulin hinge region, while in another embodiment the immunoglobulin Fc region includes at least one immunoglobulin constant heavy region, for example, a CH2 domain or a CH3 domain, and depending on the type of immunoglobulin used to generate the Fc region, optionally a CH4 domain. In another embodiment, the Fc region includes a hinge region, a CH2 domain and a CH3 domain, and preferably lacks the CH1 domain, while in another embodiment, the Fc region includes a hinge region and a CH2 domain. In yet another embodiment, the Fc region includes a hinge region and a CH3 domain. In a further embodiment, the Fc region contains a functional binding site for the Fc protection receptor, FcRp. The binding site for FcRp includes amino acids in both the CH2 and CH3 domains and the Fc-FcRp interaction contributes significantly to the extended serum half-life of Fc fusion proteins.

Although immunoglobulin Fc regions and component constant heavy domains may be from any immunoglobulin class, a preferred class of immunoglobulin for the Fc-IFN-β fusion proteins of the invention is IgG (Igγ) (γ subclasses 1, 2, 3, or 4). The nucleotide and amino acid sequences of human Fcγ1 are set forth in SEQ ID NOs: 78 and 79. Other classes of immunoglobulin, IgA (Igα), IgD (Igδ), IgE (Igϵ) and IgM (Igμ), can also be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably includes at least a portion of a hinge domain, and preferably at least a portion of a CH3 domain of Fcγ or the homologous domains in any of IgA, IgD, IgE, or IgM.

It is contemplated that the Fc region used in the generation of the fusion proteins containing the IFN-β variants can be adapted to the specific application of the molecule. In one embodiment, the Fc region is derived from an immunoglobulin γ1 isotype or variants thereof. The use of human Fcγ1 as the Fc region sequence has several advantages. For example, an Fc region derived from an immunoglobulin γ1 isotype can be used when targeting the fusion protein to the liver is desired. Additionally, if the Fc fusion protein is to be used as a biopharmaceutical, the Fcγ1 domain may confer effector function activities to the fusion protein. The effector function activities include the biological activities such as placental transfer and increased serum half-life. The immunoglobulin Fc region also provides for detection by anti-Fc ELISA and purification through binding to *Staphylococcus aureus* protein A ("Protein A"). In certain applications, however, it may be desirable to delete specific effector functions from the immunoglobulin Fc region, such as Fc receptor binding and/or complement fixation. When an Fc region derived from immunoglobulin γ1 is used, a lysine at the carboxy terminus of the immunoglobulin Fc region is typically replaced with an alanine. This improves the circulating half life of the Fc-IFN-$\beta^{sol}$ fusion protein.

Other embodiments of Fc-IFN-$\beta^{sol}$ fusion proteins use Fc regions derived from a different immunoglobulin γ isotype i.e.γ2, γ3, or γ4, or variants thereof. The Fc region can include a hinge region derived from a different immunoglobulin isotype than the Fc region itself. For example, some embodiments of Fc-IFN-$\beta^{sol}$ fusion proteins contain a hinge region derived from an immunoglobulin γ1 or a variant thereof. For instance, the immunoglobulin Fc region can be derived from an immunoglobulin γ2 isotype and include a hinge region derived from an immunoglobulin γ1 isotype or a variant thereof. In one embodiment, a cysteine residue of the γ1 hinge is modified. In a further embodiment, the first cysteine of the γ1 hinge is modified. In yet another embodiment, a serine is substituted in place of the first cysteine of the γ1 hinge. Because the immunoglobulin γ2 isotype is ineffective in mediating effector functions and displays vastly reduced binding to Fc↓ receptor (FcγR), it may be expected that this particular configuration of IFN-β fusion variant more closely mimics the biological activity of the free IFN-β molecule and in addition has the most enhanced circulating half-life when administered to a mammal. Just as with γ1, it is preferable to mutate the carboxy-terminal lysine of the Fc region-to alanine in order to improve the circulating half life of the Fc-IFN-$\beta^{sol}$ fusion protein.

As previously stated, the Fc region of Fc-IFN-$\beta^{sol}$ fusion proteins of the invention can be derived from an immunoglobulin γ4 isotype. In some embodiments of the invention, an immunoglobulin γ4 isotype is modified to contain a hinge region derived from an immunoglobulin γ1 isotype or a variant thereof. In one embodiment, a cysteine residue of the γ1 hinge is modified. In a further embodiment, the first cysteine of the γ1 hinge is modified. In yet another embodiment, a serine is substituted in place of the first cysteine of the γ1 hinge. Like immunoglobulin γ2 isotypes, immunoglobulin γ4 isotypes also exhibit lower affinity towards FcγR and thus offer similar advantages in reducing immune effector functions. When an Fc region derived from γ 1, 2, 3 or 4 is used, a lysine at the carboxy-terminus of the immunoglobulin Fc region is typically replaced with an alanine. Immunoglobulin γ4 is a preferred Fc region for making Fc-IFN-$\beta^{sol}$ fusion proteins wherein the IFN-β moiety includes alterations to one of more amino acid residues at position 17, 50, 57, 130, 131, 136 and/or 140. An exemplary amino acid sequence of an Fc-IFN-$\beta^{sol}$ fusion protein of the invention which includes an Fc region of immunoglobulin γ4 isotype modified to contain a hinge region derived from an immunoglobulin γ1 is shown in FIG. 5 (SEQ ID NO:4).

Depending on the application, constant region genes from species other than human, for example, mouse or rat, may be used. The immunoglobulin Fc region used as a fusion partner in the DNA construct generally may be from any mammalian species. Where it is undesirable to elicit an immune response in the host cell or animal against the Fc region, the Fc region may be derived from the same species as the host cell or animal. For example, a human immunoglobulin Fc region can be used when the host animal or cell is human; likewise, a murine immunoglobulin Fc region can be used where the host animal or cell will be a mouse.

Nucleic acid sequences encoding, and amino acid sequences defining a human immunoglobulin Fc region useful in the practice of the invention are set forth in SEQ ID NO:78 and SEQ ID NO:79 respectively. However, it is contemplated that other immunoglobulin Fc region sequences useful in the practice of the invention may be found, for example, by those encoded by nucleotide sequences of the heavy chain constant region which includes the Fc region sequence as disclosed in the Genbank and/or EMBL databases, for example, AF045536.1 (*Macaca fuscicularis*, nucleotide sequence SEQ ID NO:20; amino acid sequence SEQ ID NO:21), AF045537.1 (*Macaca mulatta*, nucleotide sequence SEQ ID NO:22; amino acid sequence SEQ ID NO:23), AB016710 (*Felis catus*, nucleotide sequence SEQ ID NO:24; amino acid sequence SEQ ID NO:25), K00752 (*Oryctolagus cuniculus*, nucleotide sequence SEQ ID NO:26; amino acid sequence SEQ ID NO:27), U03780 (*Sus scrofa*, nucleotide sequence SEQ ID NO:28; amino acid sequence SEQ ID NO:29), Z48947 (*Camelus dromedaries*, nucleotide sequence SEQ ID NO:30), (*Bos taurus*, nucleotide sequence SEQ ID NO:31; amino acid sequence SEQ ID NO:32), L07789 (*Mustela vison*, nucleotide sequence SEQ ID NO:33; amino acid sequence SEQ ID NO:34), X69797 (*Ovis aries*, nucleotide sequence SEQ ID NO:35; amino acid sequence SEQ ID NO:36), U17166 (*Cricetulus migratorius*, nucleotide sequence SEQ ID NO:37; amino acid sequence SEQ ID NO:38), X07189 (*Rattus rattus*, nucleotide sequence SEQ ID NO:39; amino acid sequence SEQ ID NO:40), AF157619.1 (*Trichosurus vulpecula*, nucleotide sequence SEQ ID NO:41; amino acid sequence SEQ ID NO:42), or AF035195 (*Monodelphis domestica*, nucleotide sequence SEQ ID NO:43; amino acid sequence SEQ ID NO:44).

Furthermore, it is contemplated that substitution or deletion of amino acids within the immunoglobulin heavy chain constant regions may be useful in the practice of the invention. One example may include introducing amino acid substitutions in the upper CH2 region to create an Fc variant with reduced affinity for Fc receptors (Cole et al. (1997) J. Immunol. 159:3613). One of ordinary skill in the art can prepare such constructs using well known molecular biology techniques.

It is understood that the present invention exploits conventional recombinant DNA methodologies for generating the Fc fusion proteins useful in the practice of the invention. The Fc fusion constructs preferably are generated at the DNA level, and the resulting DNAs integrated into expression vectors, and expressed to produce the fusion proteins of the invention.

As used herein, the term "vector" is understood to mean any nucleic acid including a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include a retrovirus, an adenovirus and an adeno-associated virus. As used herein, the term "gene expression" or "expression" of a target protein, is understood to mean the transcription of a DNA sequence, translation of the mRNA transcript, and secretion of an Fc fusion protein product.

A useful expression vector is pdCs (Lo et al. (1988) Protein Engineering 11:495), in which the transcription of the Fc-X gene utilizes the enhancer/promoter of the human cytomegalovirus and the SV40 polyadenylation signal. The enhancer and promoter sequence of the human cytomegalovirus used was derived from nucleotides −601 to +7 of the sequence provided in Boshart et al. (1985) Cell 41:521. The vector also contains the mutant dihydrofolate reductase gene as a selection marker (Simonsen and Levinson (1983) Proc. Nat. Acad. Sci. USA 80:2495).

An appropriate host cell can be transformed or transfected with the DNA sequence of the invention, and utilized for the expression and/or secretion of the target protein. Currently preferred host cells for use in the invention include immortal hybridoma cells, NS/0 myeloma cells, 293 cells, Chinese hamster ovary cells, HeLa cells, and COS cells.

One expression system that has been used to produce high level expression of fusion proteins in mammalian cells is a DNA construct encoding, in the 5' to 3' direction, a secretion cassette, including a signal sequence and an immunoglobulin Fc region, and a target protein such as IFNβ. Several target proteins have been expressed successfully in such a system and include, for example, IL2, CD26, Tat, Rev, OSF-2, βIG-H3, IgE Receptor, PSMA, and gp120. These expression constructs are disclosed in U.S. Pat. Nos. 5,541,087 and 5,726,044 to Lo et al.

The fusion proteins of the invention may or may not be include a signal sequence when expressed. As used herein, the term "signal sequence" is understood to mean a segment which directs the secretion of the IFN-β fusion protein and thereafter is cleaved following translation in the host cell. The signal sequence of the invention is a polynucleotide which encodes an amino acid sequence which initiates transport of a protein across the membrane of the endoplasmic reticulum. Signal sequences which are useful in the invention include antibody light chain signal sequences, e.g., antibody 14.18 (Gillies et. al. (1989) J. Immunol. Meth. 125:191), antibody heavy chain signal sequences, e.g., the MOPC141 antibody heavy chain signal sequence (Sakano et al. (1980) Nature 286:5774), and any other signal sequences which are known in the art (see, e.g., Watson (1984) Nucleic Acids Research 12:5145).

Signal sequences have been well characterized in the art and are known typically to contain 16 to 30 amino acid residues, and may contain greater or fewer amino acid residues. A typical signal peptide consists of three regions: a basic N-terminal region, a central hydrophobic region, and a more polar C-terminal region. The central hydrophobic region contains 4 to 12 hydrophobic residues that anchor the signal peptide across the membrane lipid bilayer during transport of the nascent polypeptide. Following initiation, the signal peptide is usually cleaved within the lumen of the endoplasmic reticulum by cellular enzymes known as signal peptidases. Potential cleavage sites of the signal peptide generally follow the "(−3, −1) rule." Thus a typical signal peptide has small, neutral amino acid residues in positions −1 and −3 and lacks proline residues in this region. The signal peptidase will cleave such a signal peptide between the −1 and +1 amino acids. Thus, the signal sequence may be cleaved from the amino-terminus of the fusion protein during secretion. This results in the secretion of an Fc fusion protein consisting of the immunoglobulin Fc region and the target protein. A detailed discussion of signal peptide sequences is provided by von Heijne (1986) Nucleic Acids Res. 14:4683.

As would be apparent to one of skill in the art, the suitability of a particular signal sequence for use in the secretion cassette may require some routine experimentation. Such experimentation will include determining the ability of the signal sequence to direct the secretion of an Fc fusion protein and also a determination of the optimal configuration, genomic or cDNA, of the sequence to be used in order to achieve efficient secretion of Fc fusion proteins. Additionally, one skilled in the art is capable of creating a synthetic signal peptide following the rules presented by von Heijne, referenced above, and testing for the efficacy of such a synthetic signal sequence by routine experimentation. A signal sequence can also be referred to as a "signal peptide," "leader sequence," or "leader peptides."

The fusion of the signal sequence and the immunoglobulin Fc region is sometimes referred to herein as secretion cassette. An exemplary secretion cassette useful in the practice of the invention is a polynucleotide encoding, in a 5' to 3' direction, a signal sequence of an immunoglobulin light chain gene and an Fcγ1 region of the human immunoglobulin γ1 gene. The Fcγ1 region of the immunoglobulin Fcγ1 gene preferably includes at least a portion of the immunoglobulin hinge domain and at least the CH3 domain, or more preferably at least a portion of the hinge domain, the CH2 domain and the CH3 domain. As used herein, the "portion" of the immunoglobulin hinge region is understood to mean a portion of the immunoglobulin hinge that contains at least one, preferably two cysteine residues capable of forming interchain disulfide bonds. The DNA encoding the secretion cassette can be in its genomic configuration or its cDNA configuration. Under certain circumstances, it may be advantageous to produce the Fc region from human immunoglobulin Fcγ2 heavy chain sequences. Although Fc fusions based on human immunoglobulin γ1 and γ2 sequences behave similarly in mice, the Fc fusions based on the γ2 sequences can display superior pharmacokinetics in humans.

In another embodiment, the DNA sequence encodes a proteolytic cleavage site interposed between the secretion cassette and the target protein. A cleavage site provides for the proteolytic cleavage of the encoded fusion protein thus separating the Fc domain from the target protein. As used herein, "proteolytic cleavage site" is understood to mean amino acid sequences which are preferentially cleaved by a proteolytic enzyme or other proteolytic cleavage agents. Useful proteolytic cleavage sites include amino acids sequences which are recognized by proteolytic enzymes such as trypsin, plasmin or enterokinase K. Many cleavage site/cleavage agent pairs are known (see, for example, U.S. Pat. No. 5,726,044).

Further, substitution or deletion of constructs of these constant regions, in which one or more amino acid residues of the constant region domains are substituted or deleted also would be useful. One example would be to introduce amino acid substitutions in the upper CH2 region to create an Fc variant with reduced affinity for Fc receptors (Cole et al. (1997) J. Immunol. 159: 3613). One of ordinary skill in the art can prepare such constructs using well known molecular biology techniques.

The fusion constructs disclosed herein produced high levels of Fc-IFN-$\beta^{sol}$. The initial clones produced about 100 μg/mL of altered Fc-IFN-$\beta^{sol}$, which could be purified to homogeneity by Protein A affinity chromatography. Expression levels often can be increased several fold by subcloning. As stated above, it was found that when IFN-β with the cysteine at position 17 replaced with a serine, an alanine, a valine or a methionine is expressed as Fc fusion molecules, high levels of expression were obtained, presumably because the amino acid substitution at position 17 of the IFN-$\beta^{sol}$ protein prevents aberrant disulfide bond formation in the protein and the Fc region acts as a carrier, helping the polypeptide to fold correctly and to be secreted efficiently. Similarly, other Fc-IFN-$\beta^{sol}$ fusion proteins of the invention including the mutation C17S, such as, for example Fc-(linker)-IFN-$\beta^{sol}$ (C17S F50H H131A -H140A) and Fc-(linker)-IFN-$\beta^{sol}$ (C17S L57A H131A H140T) are equally well expressed. Moreover, the Fc region is also glycosylated and highly charged at physiological pH. Therefore, the Fc region can help to solubilize hydrophobic proteins.

In addition to high levels of expression, Fc-IFN-$\beta^{sol}$ proteins exhibited greater bioactivity than the parental (un-modified) Fc-IFN-β fusion protein, as measured in a cell based anti-viral assay (Example 6), and were comparable to the bioactivity of a commercial preparation of IFN-β obtained from R&D Systems (Minneapolis, Minn.).

In addition to the high levels of expression, altered Fc-IFN-β fusion proteins exhibited longer serum half-lives compared to unaltered Fc-IFN-β fusion proteins. For example, the circulating half-life of Fc-IFN-$\beta^{sol}$ including the mutation C17S is found to be significantly greater than that of the parent Fc-IFN-β fusion protein (see Example 8).

The fusion proteins of the invention provide several important clinical benefits. As demonstrated in the tests of biological assays in Examples 6 and 7, the biological activity of altered Fc-IFN-$\beta^{sol}$ is significantly higher than that of unaltered Fc-IFN-β.

Another embodiment of the present invention provides constructs having various structural conformations, e.g., bivalent or multivalent constructs, dimeric or multimeric constructs, and combinations thereof. Such functional conformations of molecules of the invention allow the synergistic effect of IFN-β and other anti-viral and anti-cancer proteins to be explored in animal models.

An important aspect of the invention is that the sequences and properties of various IFN-β proteins and encoding DNAs are quite similar. In the context of Fc-X fusions, the properties of IFN-β proteins and encoding DNAs are essentially identical, so that a common set of techniques can be used to generate any Fc-IFN-β DNA fusion, to express the fusion, to purify the fusion protein, and to administer the fusion protein for therapeutic purposes.

The present invention also provides methods for the production of IFN-β of non-human species as Fc fusion proteins. Non-human IFN-β fusion proteins are useful for preclinical studies of IFN-β because efficacy and toxicity studies of a protein drug must be performed in animal model systems before testing in human beings. A human protein may not work in a mouse model since the protein may elicit an immune response, and/or exhibit different pharmacokinetics skewing the test results. Therefore, the equivalent mouse protein is the best surrogate for the human protein for testing in a mouse model.

The present invention provides methods of treating various cancers, viral diseases, other diseases, related conditions and causes thereof by administering the DNA, RNA or proteins of the invention to a mammal having such condition. Related conditions may include, but are not limited to multiple sclerosis; a variety of malignancies, such as acute myeloid leukemia, multiple myeloma, Hodgkin's disease, basal cell carcinoma, cervical dysplasia and osteosarcoma; a variety of viral infections, including viral hepatitis, herpes zoster and genitalis, papilloma viruses, viral encephalitis, and cytomegalovirus pneumonia.

In view of the broad roles played by IFN-β in modulating immune responses, the present invention also provides methods for treating conditions alleviated by the administration of IFN-β. These methods include administering to a mammal having the condition, which may or may not be directly related to viral infection or cancer, an effective amount of a composition of the invention. For example, a nucleic acid, such as DNA or RNA, encoding an Fc-IFN-$\beta^{sol}$ fusion protein can be administered to a subject, preferably a mammal, as a therapeutic agent. Additionally, a cell containing a nucleic acid encoding an Fc-IFN-$\beta^{sol}$ fusion protein can be administered to a subject, preferably a mammal, as a therapeutic agent. Furthermore, an Fc-IFN-$\beta^{sol}$ protein can be administered to a subject, preferably a mammal, as a therapeutic agent.

The proteins of the invention not only are useful as therapeutic agents, but one skilled in the art recognizes that the proteins are useful in the production of antibodies for diagnostic use. Likewise, appropriate administration of the DNA or RNA, e.g., in a vector or other delivery system for such uses, is included in methods of use of the invention.

Compositions of the present invention may be administered by any route which is compatible with the particular molecules. It is contemplated that the compositions of the present invention may be provided to an animal by any suitable means, directly (e.g., locally, as by injection, implantation or topical administration to a tissue locus) or systemically (e.g., parenterally or orally). Where the composition is to be provided parenterally, such as by intravenous, subcutaneous, ophthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the composition preferably includes part of an aqueous or physiologically compatible fluid suspension or solution. Thus, the carrier or vehicle is physiologically acceptable so that in addition to delivery of the desired composition to the patient, it does not otherwise adversely affect the patient's electrolyte and/or volume balance. The fluid medium for the agent thus can include normal physiologic saline.

The DNA constructs (or gene constructs) of the invention also can be used as a part of a gene therapy protocol to deliver nucleic acids encoding IFN-β or a fusion protein construct thereof. The invention features expression vectors for in vivo transfection and expression of IFN-β or a fusion protein construct thereof in particular cell types so as to reconstitute or supplement the function of IFN-β. Expression constructs of IFN-β, or fusion protein constructs thereof, may be administered in any biologically effective carrier, e.g. any formulation or composition capable of effectively delivering the IFN-β gene or fusion protein construct thereof to cells in vivo. Approaches include insertion of the subject gene in viral vectors including recombinant retroviruses, adenovirus, adeno-associated virus, and herpes simplex virus-1, or recombinant bacterial or eukaryotic plasmids. Preferred dosages per administration of nucleic acids encoding the fusion proteins of the invention are within the range of 1 μg/m2 to 100 mg/m2, more preferably 20 μg/m2 to 10 mg/m2, and most preferably 400 μg/m2 to 4 mg/m2. It is contemplated that the optimal dosage and mode of administration may be determined by routine experimentation well within the level of skill in the art.

Preferred dosages of the fusion protein per administration are within the range of 0.1 mg/m2-100 mg/m2, more preferably, 1 mg/m2-20 mg/m2, and most preferably 2 mg/m2-6 mg/m2. It is contemplated that the optimal dosage, however, also depends upon the disease being treated and upon the existence of side effects. However, optimal dosages may be determined using routine experimentation. Administration of the fusion protein may be by periodic bolus injections, or by continuous intravenous or intraperitoneal administration from an external reservoir (for example, from an intravenous bag) or internal (for example, from a bioerodable implant). Furthermore, it is contemplated that the fusion proteins of the invention also may be administered to the intended recipient together with a plurality of different biologically active molecules. It is contemplated, however, that the optimal combination of fusion protein and other molecules, modes of administration, dosages may be determined by routine experimentation well within the level of skill in the art.

The invention is illustrated further by the following non-limiting examples.

EXAMPLES

Example 1

Cloning of huFc-huInterferon-beta (huFc-IFN-β) and huFc-IFN-$\beta^{sol}$ Mutants Human interferon β (IFN-β) cDNA was ordered from American Type Culture Collection (ATCC Number 31903). The sequence for the mature form was amplified by Polymerase Chain Reactions (PCR). The forward primer used in the amplification reactions was 5' C CCG GGT ATG AGC TAC AAC TTG CTT (SEQ ID NO:45), where the sequence CCCGGGT encodes the carboxy terminus of the CH3 without the lysine codon, as well as the restriction endonuclease site SmaI CCCGGG (Lo et al., Protein Engineering (1998) 11:495), and the sequence in bold encodes the N-terminus of the mature IFN-β coding sequence. The reverse primer for this reaction was 5' CTC GAG TCA GTT TCG GAG GTA ACC TGT (SEQ ID NO:46), where TCA is the anticodon of the translation stop codon, and CTCGAG is the restriction site Xho I. The amplified 450 bp PCR product was cloned into the pCRII vector (Invitrogen), and its sequence verified.

The SmaI-XhoI restriction fragment with the completely correct mature IFN-β sequence was used for cloning into the expression vector pdCs-huFc, such that the coding sequence of mature IFN-β was fused in frame to the 3'-end of the Fc coding sequence. The expression plasmid pdCs-huFc-IFN-β was constructed by ligating the SmaI-XhoI restriction fragment containing the mature IFN-β cDNA with the SmaI-XhoI restriction fragment of the pdCs-huFc vector according to Lo et al., (Protein Engineering (1998) 11:495). The huFc DNA corresponds to a sequence that when expressed produces the Fc fragment of the human immunoglobulin γ4 with a modified γ1 hinge sequence. The amino acid sequence is shown in SEQ ID NO:77.

To generate further fusion proteins including the IFN-β fused to Fc moieties of a different isotype or containing other alterations, the same cloning strategy was used, while substituting the appropriate version of pdCs-huFc vector. Thus, the SmaI-XhoI restriction fragment of IFN-β was inserted into pdCS-huFc vector digested with SmaI and XhoI, which encoded either an immunoglobulin γ 4 isotype with a γ 4-derived hinge region, or an immunoglobulin γ 1 isotype, or an immunoglobulin γ 2 isotype, or an immunoglobulin γ2 isotype but with an altered immunoglobulin γ 1-derived hinge region. Because the introduction of the SmaI cloning site into the vector encoding an immunoglobulin γ 4 isotype does not result in a silent mutation in the expressed protein of the Fc moiety, the protein sequence encoded by the nucleic acid sequence around the SmaI site is LSLSPG (SEQ ID NO:53). Had the mutation been silent, the sequence would have present been LSLSLG (See e.g. FIG. 7, residues 101-106 or SEQ ID NO:76).

The cysteine 17 to serine (C17S) mutation was introduced into the IFN-β nucleotide sequence by an overlapping PCR method (Daugherty et al., (1991) Nucleic Acids Res. 19:2471) using complementary mutagenic primers. The forward primer sequence was: 5' AGA AGC AGC AAT TTT CAG AGT CAG AAG CTC CTG TGG CA (SEQ ID NO:47), where the underlined nucleotide indicates the introduced point mutation (TGT to AGT). Accordingly, the reverse primer was: 5' TG CCA CAG GAG CTT CTG ACT CTG AAA ATT GCT GCT TCT (SEQ ID NO:48). The PCR fragment generated by the overlapping PCR method was ligated to the pCRII vector, the sequence verified, and the SmaI-XhoI fragment ligated to any of the pdCs-huFc expression vectors as described above. The amino acid sequence is shown as SEQ ID NO:3. The sequence of the mouse counterpart with the mutation is depicted in SEQ ID NO:12.

As discussed above, the cysteine at position 17 is mutated to a serine in the Fc-IFN-$\beta^{sol}$ protein that has the Fc portion including immunoglobulin γ 4 with a modified γ 1 hinge sequence. The amino acid sequence is shown as SEQ ID NO:4.

To introduce a flexible linker sequence between the huFc moiety and the IFN-β moiety, a synthetic oligonucleotide duplex of the sequence 5' G GGT GCA GGG GGC GGG GGC AGC GGG GGC GGA GGA TCC GGC GGG GGC TC 3' (SEQ ID NO:49) was produced. This blunt-ended, double-stranded duplex was inserted at the unique SmaI site of the expression vector pdCs-huFc-IFN-β by ligation. The orientation of the blunt-ended duplex in the resultant vector, pdCs-huFc-(GS linker)-IFN-β was confirmed by sequencing. As a result, the amino acid sequence GAGGGGSGGGGSGGGS (SEQ ID NO:50) was added between the proline (codon CCG) and the glycine (codon GGT) residues encoded by the C CCG GGT (SEQ ID NO:51) sequence containing the SmaI site. The amino acid sequence of a huFc-(GS linker) IFN-β starting with the CH3 domain of the Fcγ4 isotype is shown in FIG. 6 (SEQ ID NO:5). When using this linker with immunoglobulin γ4 constructs of the invention, it is important to note that LSLSPG (SEQ ID NO:52) C-terminal amino acid sequence of immunoglobulin γ4 lacks the alanine residue present in the immunoglobulin γ1, γ2 or γ3 C-terminal sequence LSLSPGA (SEQ ID NO:53). As stated earlier, the alanine is the result of mutating the native lysine residue. When the linker is inserted in the γ1, γ2 or γ3 construct, terminal glycine and alanine residues are identically substituted by a glycine and alanine of the linker. Thus, when the linker is inserted into immunoglobulin γ4 Fc-IFN-β, the amino acid sequence gains an additional alanine residue when the C-terminal glycine is replaced by glycine and alanine. This is exemplified by comparing, for example, FIG. 5, residues 226-231 (SEQ ID NO:4) and FIG. 6, beginning at residue 101 (SEQ ID NO:5).

Further Fc-IFN-$\beta^{sol}$ protein variants can be produced that contain mutations in the IFN-β moiety. For example, C17 may be altered to another amino acid, for instance alanine. In order to introduce the C17A mutation, the following mutagenic oligonucleotides are used: the forward primer is 5' AGA AGC AGC AAT TTT CAG GCT CAG AAG CTC CTG TGG CA 3', (SEQ ID NO:54), and the reverse primer is 5' TG CCA CAG GAG CTT CTG AGC CTG AAA ATT GCT GCT TCT 3', (SEQ ID NO:55), where the underlined nucleotides indicate the introduced mutations.

Further mutations in Fc-IFN-$\beta^{sol}$ were introduced in the IFN-β moiety by overlap PCR. Preferred IFN-β fusion proteins of the invention, Fcγ4h-(linker)-IFN-$\beta^{sol}$(C17S L57A H131A H140A) and Fcγ4h-(linker)-IFN-$\beta^{sol}$(C17S F50H H131A H140A), are produced by starting with the template Fcγ4h-linker-IFN-βsol(C17S) prepared using methods previously described herein.

To introduce the H131A mutation to the Fcγ4h-(linker)-IFN-$\beta^{sol}$(C 17S) template, a first nucleic acid fragment is created by PCR using the forward primer sequence 5' CTC CCT GTC CCC GGG TGC AGG GGG (SEQ ID NO:56), which incorporates the restriction endonuclease XmaI site, and the reverse primer sequence 5' CTT GGC CTT CAG GTA GGC CAG AAT CCT CCC ATA ATA TC (SEQ ID NO:57), where GGC represents the H131A mutation. A second fragment of the fusion protein is created by PCR using the forward primer sequence 5'GAT ATT ATG GGA GGA TTC TGG CCT ACC TGA AGG CCA AG (SEQ ID NO:58), where GGC represents the H131A mutation, and the reverse primer sequence 5' CTT ATC ATG TCT GGA TCC CTC GAG (SEQ ID NO:59), which incorporates the BamHI restriction site. The products from these reactions are purified on an electrophoretic gel according to standard methods. The gel purified fragments are then together subjected to PCR using the forward primer sequence 5'CTC CCT GTC CCC GGG TGC AGG GGG (SEQ ID NO:60), which incorporates the XmaI restriction site, and the reverse primer sequence 5' CTT ATC ATG TCT GGA TCC CTC GAG (SEQ ID NO:61), which incorporates the BamHI restriction site. This results in a nucleic acid encoding Fcγ4h-linker-IFN-βsol(C17S H131A).

Next, the H140A mutation is introduced by subjecting the Fcγh-linker-IFN-$\beta^{sol}$(C17S H131A) to PCR to create a first fragment using the forward primer sequence 5'CTC CCT GTC CCC GGG TGC AGG GGG (SEQ ID NO:62), which incorporates the restriction endonuclease XmaI site, and the reverse primer sequence 5' GGT CCA GGC ACA GGC ACT GTA CTC CTT GGC (SEQ ID NO:63), where GGC represents the H140A mutation. A second fragment of the fusion protein is created by PCR using the forward primer sequence 5' GGC AAG GAG TAC AGT GCC TGT GCC TGG ACC (SEQ ID NO:64), where GCC represents the H140A mutation. The reverse primer sequence is 5' CTT ATC ATG TCT GGA TCC CTC GAG (SEQ ID NO:65), which incorporates the BamHI restriction site. The products from these reactions are purified on an electrophoretic gel according to standard methods. The gel purified fragments are then together subjected to PCR using the forward primer sequence 5'CTC CCT GTC CCC GGG TGC AGG GGG (SEQ ID NO:66), which incorporates the XmaI restriction site, and the reverse primer sequence 5' CTT ATC ATG TCT GGA TCC CTC GAG (SEQ ID NO:67), which incorporates the BamHI restriction site. This results in a nucleic acid encoding Fcγ4h-linker-IFN-$\beta^{sol}$ (C17S H131A H140A). Alternatively, this process may be followed to instead insert the H140T mutation of the invention by modifying the appropriate primers to express the threonine codon ACC.

Finally, to introduce either the F50H mutation or the L57A mutation to the template Fcγ4h-linker-IFN-$\beta^{sol}$(C17S H131A H140A) template prepared in the previous step, a first nucleic acid fragment is created by PCR using the forward primer 5'CTC CCT GTC CCC GGG TGC AGG GGG (SEQ ID NO:68), which incorporates the restriction endonuclease XmaI site, and either the reverse primer sequence 5' GAG CAT CTC ATA GAT GGT GGC TGC GGC GTC CT C (SEQ ID NO:69), where GGC represents the codon for creating the L57A mutation or the reverse primer sequence 5' GTC CTC CTT CTG ATG CTG CTG CAG CTG (SEQ ID NO:70), where ATG represents the codon creating the F50H mutation. To create the second fragment of the fusion protein for the L57A mutation, the template is subjected to PCR using the forward primer sequence 5' GAG GAC GCC GCA GCC ACC ATC TAT GAG ATG CTC (SEQ ID NO:71), where GCC represents the L57A mutation. To create the second fragment of the fusion protein for introducing the F50H mutation, the template is subjected to PCR using the forward primer sequence 5' CAG CTG CAG CAG CAT CAG AAG GAG GAC (SEQ ID NO:72), where CAT represents the F50H mutation. The reverse primer for production of the second fragment of either mutation is 5' CTT ATC ATG TCT GGA TCC CTC GAG (SEQ ID NO:73), which incorporates the BamHI restriction site. The products from these reactions are purified on an electrophoretic gel according to standard methods. The gel purified fragments are then used as the PCR to produce a nucleic acid encoding Fcγ4h-linker-IFN-$\beta^{sol}$(C17S L57A H131A H140A) or Fcγ4h-linker-IFN-$\beta^{sol}$(C17S F50H H131A H140A). The forward and reverse primers for this reaction are 5'CTC CCT GTC CCC GGG TGC AGG GGG (SEQ ID NO:74) and 5' CTT ATC ATG TCT GGA TCC CTC GAG (SEQ ID NO:75), respectively, as used in previous steps.

Example 2

Transfection and Expression of Fc-IFN-β Fusion Proteins

For rapid analysis of protein expression, the plasmid pdCs-huFc-IFN-β, pdCs-huFc-IFN-$\beta^{sol}$(C17S) or other huFc fusion protein variants containing huIFN-β were introduced into human embryonic kidney HEK 293 cells (ATCC# CRL-1573) by transient transfection using lipofectamine (Invitrogen).

To obtain stably transfected clones which express huFc-IFN-$\beta^{sol}$(C17S), for example, the appropriate plasmid DNA was introduced into the mouse myeloma NS/0 cells by electroporation. NS/0 cells were grown in Dulbecco's modified Eagle's medium supplemented with 10% heat-inactivated fetal bovine serum, 2 mM glutamine and penicillin/streptomycin. About $5\times10^6$ cells were washed once with PBS and resuspended in 0.5 ml PBS. 10 μg of linearized plasmid DNA were then incubated with the cells in a Gene Pulser Cuvette (0.4 cm electrode gap, BioRad) on ice for 10 min. Electroporation was performed using a Gene Pulser (BioRad, Hercules, Calif.) with settings at 0.25 V and 500 μF. Cells were allowed to recover for 10 min on ice, after which they were resuspended in growth medium and plated onto two 96 well plates. Stably transfected clones were selected by their growth in the presence of 100 nM methotrexate (MTX), which was added to the growth medium two days post-transfection. The cells were fed every 3 days for two to three more times, and MTX-resistant clones appeared in 2 to 3 weeks. Supernatants from clones were assayed by anti-Fc ELISA to identify high producers. High producing clones were isolated and propagated in growth medium containing 100 nM MTX. The growth medium typically used was H-SFM or CD medium (Life Technologies).

Alternatively, clones stably expressing huFc-IFN-$\beta^{sol}$ fusion proteins were obtained in human embryonic kidney HEK 293 cells by methotrexate selection, by a method similar to the one described above. HEK 293 clones were maintained in DMEM supplemented with 10% FBS.

Example 3

Characterization of huFc-IFN-β Fusion Proteins from Cell Supernatants

The huFc-IFN-β fusion proteins were subsequently captured from the medium for further analysis. For routine characterization by gel electrophoresis, the huFc-IFN-β fusion proteins secreted into the medium was captured on Protein A Sepharose beads (Repligen, Cambridge, Mass.) and then eluted by boiling the sample in protein sample buffer, with or without a reducing agent such as β-mercaptoethanol. The samples were analyzed by SDS-PAGE and the protein bands were visualized by Coomassie staining.

Figure 2:
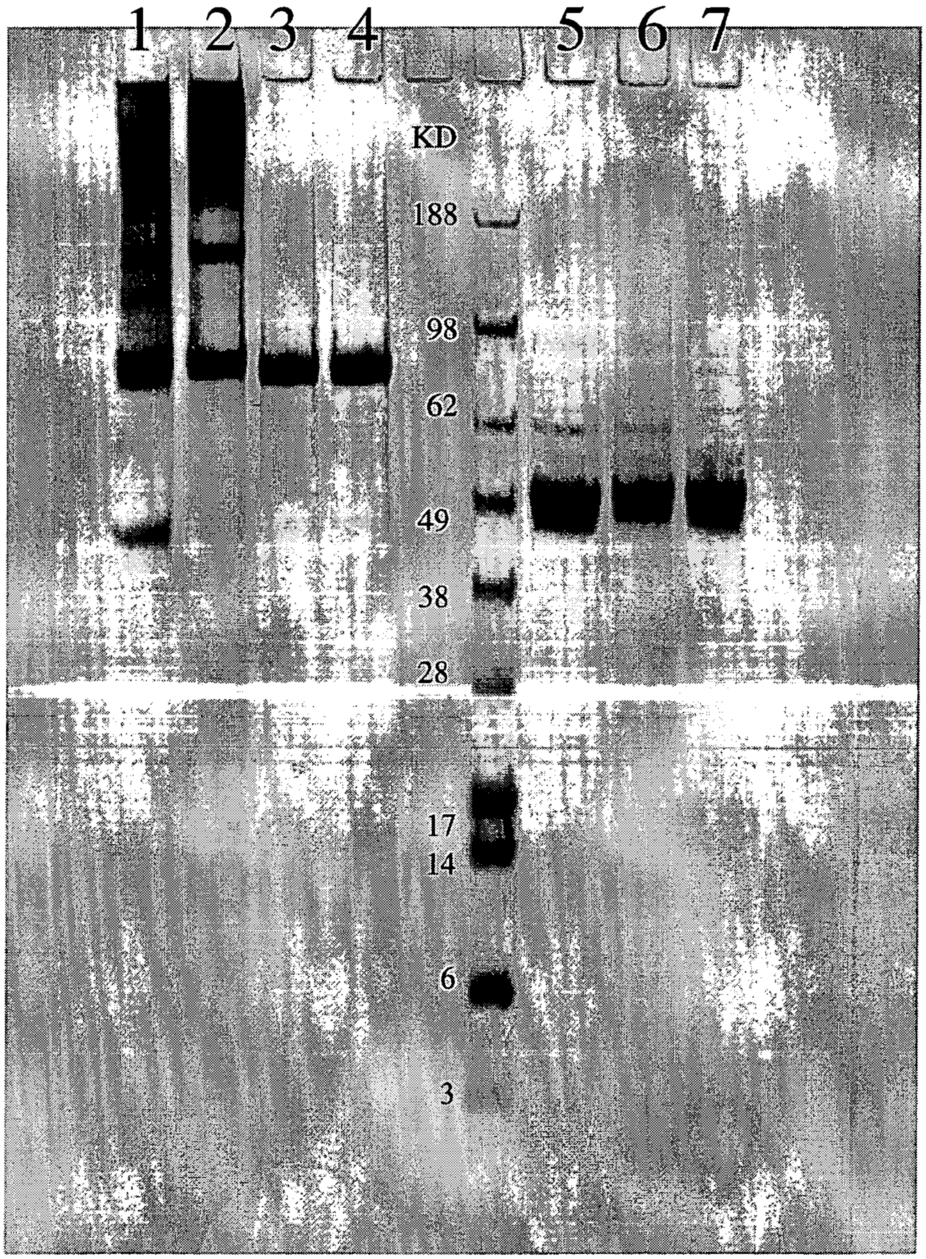
FIG. 2 is a photograph of an SDS-PAGE gel showing the migration patterns of HuFc-γ4-IFN-β and HuFc-γ4h-IFN-β fusion proteins without the C17S mutation and HuFc-γ4h-IFN-β(C17S) fusion proteins in both reducing and non-reducing chemical environments.

When huFc-IFN-β protein containing an immunoglobulin γ 4 isotype was analyzed by SDS-PAGE, it was found that the protein was not expressed in mammalian tissue culture cells as a uniform species. As shown in FIG. 2, under non-reducing conditions, in addition to a major band at 100 kDa which represented the huFc-IFN-β, multiple other bands were clearly visible, as well as an unresolved trail of higher molecular weight proteins. These results indicated that when expressed as an Fc fusion protein, the wildtype IFN-β formed aggregates. This finding was in contrast to what is generally found with unmodified IFN-β; when the wildtype sequence is cloned into an expression vector, and expressed and secreted in mammalian cell culture it is found to be 98% monomeric by size exclusion chromatography (Runkel et al., (1998), Pharmaceutical Research 15:641). This result was further unexpected in light of the fact that IFN-β can be produced as a fusion protein of the form IFN-β-Fc. See, for example, U.S. Pat. No. 5,908,626.

A portion of these aggregates was stable to reducing agents, as additional bands to the expected 50 kDa band for huFc-IFN-β persisted in a reducing SDS-PAGE system. However, the amount of material exhibiting abnormal migration was vastly diminished. This result suggested that to a significant extent the aggregation was due to scrambled disulfide bond formation.

An Fc-IFN-β variant which contained a substitution of the hinge region with one derived from immunoglobulin γ 1 was analyzed. It was found that this substitution had no impact on the behavior of the fusion protein, although it did not contain four disulfide bonds like the immunoglobulin γ 4 hinge region. Similarly, using an Fc isotype derived from an immunoglobulin γ 1 in the fusion construct also had no effect. Thus, while the aggregation appeared to be due to the presence of the Fc moiety, the aggregation could not be alleviated by alterations in the Fc moiety.

It has been reported that when IFN-β is fused to the N-terminal region of Fc, the introduction of a linker sequence is useful. See, for example, U.S. Pat. No. 5,908,626. Similar to the Fc-IFN-β fusion proteins with either the altered hinge regions or altered Fc regions, an Fc-IFN-β fusion protein containing a Gly-Ser linker region, which separates the Fc region from the IFN-β moiety also yields the same result as above.

In contrast, SDS-PAGE analysis of huFc-IFN-β(C17S) revealed that this protein was substantially non-aggregated. Under non-reducing conditions, the band of 100 kDa corresponding to huFc-IFN-β (C17S) represented practically the only visible band on the gel. Moreover, under reducing conditions, the more prominent band representing aggregated fusion protein, most probably due to interaction of exposed hydrophobic patches, was also absent. Therefore, the introduction of a cysteine substitution at position 17 of the mature sequence of IFN-β promoted the correct folding of the fusion protein. This result was surprising on two counts: for one, the presence of a free cysteine in the “X” portion of an Fc-X protein had not presented a problem in other fusion proteins, such as Fc-IL2; and the presence of the free cysteine in IFN-β had not presented a problem either when the free protein or when an IFN-β-Fc protein were expressed in a mammalian expression system.

Example 4

ELISA Procedures

The concentration of human Fc-containing protein products in the supernatants of MTX-resistant clones and other test samples were determined by anti-huFc ELISA. Standard procedures as described in detail below were essentially followed.

A. Coating Plates

ELISA plates were coated with AffiniPure Goat anti-Human IgG (H+L) (Jackson Immuno Research Laboratories, West Grove, Pa.) at 5 μg/mL in PBS, and 100 μL/well in 96-well plates (Nunc-Immuno plate Maxisorp). Coated plates were covered and incubated at 4° C. overnight. Plates then were washed 4 times with 0.05% Tween (Tween 20) in PBS, and blocked with 1% BSA/1% goat serum in PBS, 200 μL/well. After incubation with the blocking buffer at 37° C. for 2 hrs, the plates were washed 4 times with 0.05% Tween in PBS and tapped dry on paper towels.

B. Incubation with Test Samples and Secondary Antibody

Test samples were diluted as appropriate in sample buffer (1% BSA/1% goat serum/0.05% Tween in PBS). A standard curve was prepared using a chimeric antibody (with a human Fc), the concentration of which was known. To prepare a standard curve, serial dilutions were made in the sample buffer to give a standard curve ranging from 125 ng/mL to 3.9 ng/mL. The diluted samples and standards were added to the plate, 100 μL/well and the plate incubated at 37° C. for 2 hr. After incubation, the plate was washed 8 times with 0.05% Tween in PBS. To each well was then added 100 μL of the secondary antibody, the horseradish peroxidase-conjugated anti-human IgG (Jackson Immuno Research), diluted around 1:120,000 in the sample buffer. The exact dilution of the secondary antibody has to be determined for each lot of the HRP-conjugated anti-human IgG. After incubation at 37° C. for 2 hr, the plate was washed 8 times with 0.05% Tween in PBS.

C. Development

The substrate solution was added to the plate at 100 μL/well. The substrate solution was prepared by dissolving 30 mg of OPD (o-phenylenediamine dihydrochloride (OPD), (1 tablet) into 15 mL of 0.025 M Citric acid/0.05 M Na2HPO4 buffer, pH 5, which contained 0.03% of freshly added hydrogen peroxide. The color was allowed to develop for 30 min. at room temperature in the dark. The developing time is subject to change, depending on lot to lot variability of the coated plates, the secondary antibody, etc. The reaction was stopped by adding 4N sulfuric acid, 100 μL/well. The plate was read by a plate reader, which was set at both 490 and 650 nm and programmed to subtract the background OD at 650 nm from the OD at 490 nm.

Example 5

Purification and Analysis of huFc-IFN-β Proteins

A standard purification of Fc-containing fusion proteins was performed based on the affinity of the Fc protein moiety for Protein A. Briefly, cell supernatants (from cells transfected with wildtype or mutant proteins) containing the fusion protein were loaded onto a pre-equilibrated (50 mM Sodium Phosphate, 150 mM NaCl at neutral pH) Protein A Sepharose Fast Flow column and the column was washed extensively in buffer (50 mM Sodium Phosphate, 150 mM NaCl at neutral pH). Bound protein was eluted at a low pH (pH 2.5) in same buffer as above and fractions were immediately neutralized, optionally by eluting directly into a solution of 1M Tris base, pH 11.

The Protein A Sepharose—purified huFc-IFN-β and huFc-IFN-$\beta^{sol}$ fusion proteins were analyzed by analytical size exclusion chromatography (SEC), and the % non-aggregated material was quantified by calculating the area under the curve of chromatogram peaks. The integrity and purity of the fusion proteins was verified by SDS-PAGE electrophoresis.

TABLE 1

Analytical SEC analysis of Fc-IFN-β fusion proteins

| Protein | % non-aggregated |
|---|---|
| Fc-γ4h-IFN-β | 0 |
| Fc-γ4h-IFN-β(C17S) | 11 |
| Fc-γ4h-linker-IFN-β(C17S) | 21-30 |
| Fc-γ4h-linker-IFN-β(C17S F50H H131A H140A) | 52 |
| Fc-γ4h-linker-IFN-β(C17S L57A H131A H140T) | 49 |

In a second purification step, neutralized Protein A Sepharose eluates containing Fc-IFN-$\beta^{sol}$ fusion proteins were applied to a preparative SEC column and peak fractions were collected, yielding Fc-IFN-$\beta^{sol}$ protein preparations consisting of at least 90% non-aggregated material. While the yield of purified product for Fc-γ4h-linker-IFN-β(C17S) was about 10%, for Fc-γ4h-linker-IFN-$\beta^{sol}$(C17S L57A H131A H140T) it was about 75%. This result indicated that the combination of mutations C17S with, for example L57A, H131A, and H140T in the IFN-β moiety significantly promoted the solubility characteristics of the Fc-IFN-β fusion proteins.

Example 6

Measurement of Antiviral Activity

Viral replication in cell culture often results in cytotoxicity, an effect known as cytopathic effect (CPE). Interferons can inhibit viral proliferation and protect cells from CPE. The antiviral activity of IFN-β can be quantitated by cytopathic effect reduction (CPER), as described in "*Lymphokines and Interferons: A Practical Approach*", edited by M. J. Clemens, A. G. Morris, and A. J. H. Gearin, I. R. L. Press, Oxford, 1987. The antiviral activities of purified huFc-IFN-β and huFc-IFN-$\beta^{sol}$ were compared relative to a commercial huIFN-β standard (R&D Systems) or Betaferon (Serono) using the human epithelial lung carcinoma line A549 (ATCC # CCL-185) and the encephalomyocarditis virus (EMCV; ATCC # VR 129B) according to the CPER protocol described in the above reference. The effective dose (ED50) was set as the amount of protein that led to 50% CPER (i.e. 50% of the cells being protected from lysis), determined relative to uninfected control cells. The ED50 values were the average of at least three separate experiments. It was found that the effective doses that gave 50% CPER were 50 pg/ml for huFc-IFN-β 70 pg/ml for huFc-IFN-$\beta^{sol}$(C17S), 14 pg/ml for huFc-IFN-$\beta^{sol}$(C17S, F50H, H131A, H140A) and 17 pg/ml for huFc-IFN-$\beta^{sol}$ (C17S, L57A, H131A, H140T). These values, which had been normalized to the amount of IFN-β in the fusion protein, correlated well with the ED50 of 90 pg/ml or 40 pg/ml found with the commercial standard or Betaferon, respectively. Therefore, the IFN-β fusion proteins retained substantial anti-viral activity in a CPER assay, and the huFc-IFN-$\beta^{sol}$ fusion proteins had an ED50 about equivalent to that of the free huIFN-β.

Example 7

Cellular Growth Inhibition Assay

The activity of the purified Fc-IFN-β fusion proteins was further determined in a cellular growth inhibition assay. The proliferation of Daudi cells (ATCC # CCL-123), a B lymphoblast line derived from a patient with Burkitt's lymphoma, is normally inhibited by IFN-β. Accordingly, the antiproliferative effects of fusion proteins huFc-IFN-β and huFc-IFN-$\beta^{sol}$ (C17S) on Daudi cells were compared relative to a commercial human standard (Calbiochem). To set up the assay for each of these proteins, a dilution series covering about a thousand fold concentration range was prepared in RPMI medium supplemented with 10% fetal bovine serum, and 100 μl samples were aliquoted in wells of a 96 well plate. Daudi cells in growth phase were washed and resuspended at $2\times10^5$ cells/ml in the RPMI medium supplemented with 10% fetal bovine serum, and 100 μl of the cells were aliquoted to each well containing the IFN-β dilutions. Further control wells contained either untreated cells or medium alone. After incubation for an additional 72 hours proliferation was measured by mitochondrial dehydrogenase activity, using the chromogenic enzyme substrate MTS (Promega # G5421) in the presence of the electron donor PMS (Sigma # P 5812). The ED50 values, determined from activity curves, were found to be around 3 ng/ml to 3.5 ng/ml for each of the fusion proteins as well as for the commercial IFN-β protein. It was therefore concluded that the IFN-β fusion proteins were as effective as the free IFN-β in inhibiting Daudi cell growth.

Example 8

Pharmacokinetics of huFc-IFN-β Proteins

The pharmacokinetics of huFc-IFN-β and huFc-IFN-$\beta^{sol}$ fusion proteins are determined in a group of 4 Balb/c mice, for each protein. Twenty-five milligrams of the fusion protein is injected into the tail vein of each mouse. Blood is obtained by retro-orbital bleeding immediately after injection (i.e., at t=0 min), and at 30 min, 1 hr, 2 hrs, 4 hrs, 8 hrs, and 24 hrs post-injection. Blood samples are collected in tubes containing heparin to prevent clotting. Cells are removed by centrifugation in an Eppendorf high-speed microcentrifuge for 4 min at 12,500 g. The concentration of either Fc-huIFN-β or huFc-IFN-$\beta^{sol}$ in the plasma is measured by anti-huFc ELISA and Western blot analysis using anti-huFc antibody. Alternatively, an IFN-β ELISA may be used. The integrity of the circulating fusion protein is ascertained by an immunoblot of the serum probed with an anti-huFc antibody or with an anti-IFN-β antibody. It is found that the circulating half-life of huFc-IFN-$\beta^{sol}$ is greater than that of huFc-IFN-β, and at least 5-fold that of the free IFN-β.

Furthermore, it is contemplated that the specific effects of Fc-IFN-$\beta^{sol}$ are more pronounced in treatment of conditions and diseases such as multiple sclerosis, where administration of IFN-β is known to alleviate the condition.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description. All changes which come within the meaning and range of equivalency of the claims are therefore intended to be embraced therein.

What is claimed is:

1. A method of stabilizing an Fc-interferon-β fusion protein comprising the step of making an Fc-interferon-β fusion protein, the Fc-interferon-β fusion protein comprising:

an immunoglobulin Fc region; and a human interferon-β protein linked by a peptide bond or a peptide linker sequence to the carboxy-terminus of the immunoglobulin Fc region, wherein the interferon-β protein has the amino acid substitutions:

C17S and F50H and H131A, and either H140T or H140A; or

C17S and L57A and H131A, and either H140T or H140A, wherein said substitutions correspond to positions in mature, full-length human interferon-β.

2. The method of claim 1, wherein the immunoglobulin Fc region comprises an immunoglobulin hinge region and an immunoglobulin heavy chain constant region.

3. The method of claim 1, wherein the immunoglobulin Fc region is derived from IgG4, IgG2, IgG1, or a combination thereof.

4. The method of claim 3, wherein the immunoglobulin Fc region comprises an immunoglobulin heavy chain constant region derived from IgG4 and an immunoglobulin hinge region derived from IgG1.

5. The method of claim 4, wherein a cysteine residue of the hinge region has been mutated.

6. The method of claim 3, wherein the immunoglobulin Fc region is derived from IgG1, and an alanine residue is substituted in place of a C-terminal lysine of the immunoglobulin Fc region.

7. The method of claim 3, wherein the immunoglobulin Fc region comprises an immunoglobulin heavy chain constant region derived from IgG2, and an immunoglobulin hinge region derived from IgG1.

8. The method of claim 7, wherein a cysteine residue of the hinge region has been mutated.

9. The method of claim 3, wherein the immunoglobulin Fc region is derived from IgG2, and an alanine residue is substituted in place of the C-terminal lysine of the immunoglobulin Fc region.

10. The method of claim 1, wherein the human interferon-β protein is linked to the carboxy-terminus of the immunoglobulin Fc region by a peptide linker having the amino acid sequence of SEQ ID NO: 1.

11. The method of claim 1, wherein the immunoglobulin Fc region comprises IgG1, IgG2, or IgG4.

12. The method of claim 1, wherein the immunoglobulin Fc region comprises IgG4 and at least a portion of a hinge of IgG1.

13. The method of claim 1, wherein said fusion protein comprises the amino acid sequence of SEQ ID NO: 8.

14. The method of claim 1, wherein stabilizing comprises:

(i) increasing the circulating half-life of the Fc-interferon-β fusion protein relative to an unaltered Fc-interferon-β fusion protein, or (ii) decreasing the aggregation of the Fc-interferon-β fusion protein relative to an unaltered Fc-interferon-β fusion protein, or (iii) increasing the biological activity of the Fc-interferon-β fusion protein relative to an unaltered Fc-interferon-β fusion protein.

* * * * *